United States Patent
Raguram et al.

(10) Patent No.: US 10,947,300 B2
(45) Date of Patent: *Mar. 16, 2021

(54) AGENTS FOR INFLUENZA NEUTRALIZATION

(71) Applicant: Massachusetts Institute of Technology, Cambridge, MA (US)

(72) Inventors: S. Raguram, Hillsborough, NJ (US); Viswanathan Sasisekharan, Cambridge, MA (US); Venkataramanan Soundararajan, Windham, NH (US); Ram Sasisekharan, Lexington, MA (US); Vidya Subramanian, Somerville, MA (US); Kannan Tharakaraman, Woburn, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/675,826

(22) Filed: Nov. 6, 2019

(65) Prior Publication Data
US 2020/0123234 A1    Apr. 23, 2020

Related U.S. Application Data

(60) Continuation of application No. 15/959,430, filed on Apr. 23, 2018, now Pat. No. 10,538,578, which is a continuation of application No. 15/595,407, filed on May 15, 2017, now Pat. No. 9,982,037, which is a division of application No. 13/829,675, filed on Mar. 14, 2013, now Pat. No. 9,683,030.

(60) Provisional application No. 61/645,453, filed on May 10, 2012.

(51) Int. Cl.
| | | |
|---|---|---|
| *C07K 16/10* | (2006.01) | |
| *A61P 31/16* | (2006.01) | |
| *A61K 39/00* | (2006.01) | |

(52) U.S. Cl.
CPC ......... *C07K 16/1018* (2013.01); *A61P 31/16* (2018.01); *A61K 2039/505* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,166,452 A | 9/1979 | Generales, Jr. |
| 4,270,537 A | 6/1981 | Romaine |
| 4,472,509 A | 9/1984 | Gansow et al. |
| 4,596,556 A | 6/1986 | Morrow et al. |
| 4,790,824 A | 12/1988 | Morrow et al. |
| 4,816,567 A | 3/1989 | Cabilly et al. |
| 4,886,499 A | 12/1989 | Cirelli et al. |
| 4,938,948 A | 7/1990 | Ring et al. |
| 4,940,460 A | 7/1990 | Casey et al. |
| 4,941,880 A | 7/1990 | Burns |
| 5,015,235 A | 5/1991 | Crossman |
| 5,021,236 A | 6/1991 | Gries et al. |
| 5,064,413 A | 11/1991 | McKinnon et al. |
| 5,141,496 A | 8/1992 | Dalto et al. |
| 5,190,521 A | 3/1993 | Hubbard et al. |
| 5,196,066 A | 3/1993 | Kusuda et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,500,161 A | 3/1996 | Andrianov et al. |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,741,957 A | 4/1998 | Deboer et al. |
| 5,750,172 A | 5/1998 | Meade et al. |
| 5,756,687 A | 5/1998 | Denman et al. |

(Continued)

FOREIGN PATENT DOCUMENTS

| | | |
|---|---|---|
| CN | 101553502 A | 10/2009 |
| CN | 101821290 A | 9/2010 |

(Continued)

OTHER PUBLICATIONS

Aich, U. et al., Glycomics-based analysis of chicken red blood cells provides insight into the selectivity of the viral agglutination assay, the FEBS Journal, 278(10):1699-1712 (2011).
Allison, The mode of action of immunological adjuvants, Dev. Biol. Stand., 92:3-11, (1998).
Altschul, et al., Basic local alignment search tool, J. Mol. Biol., 215(3): 403-410 (1990).
Altschul, et al., Gapped BLAST and PSI-BLAST: a new generation of protein database search programs, Nucleic Acids Res. 25:3389-3402, (1997).

(Continued)

*Primary Examiner* — Agnieszka Boesen
(74) *Attorney, Agent, or Firm* — Choate, Hall & Stewart LLP; Brenda Herschbach Jarrell

(57) ABSTRACT

The present invention provides antibodies (e.g., monoclonal antibodies, human antibodies, humanized antibodies, etc.), which bind to multiple influenza strains. Such antibodies are useful, for example, in the prophylaxis, treatment, diagnosis, and/or study of influenza.

18 Claims, 16 Drawing Sheets

Specification includes a Sequence Listing.

(56) References Cited

U.S. PATENT DOCUMENTS

| | | | |
|---|---|---|---|
| 5,827,690 | A | 10/1998 | Meade et al. |
| 5,893,397 | A | 4/1999 | Peterson et al. |
| 5,993,412 | A | 11/1999 | Deily et al. |
| 7,045,337 | B2 | 5/2006 | Schultz et al. |
| 7,118,915 | B2 | 10/2006 | Vogt et al. |
| 7,252,998 | B2 | 8/2007 | Skerra et al. |
| 7,255,859 | B1 | 8/2007 | Emrich et al. |
| 7,332,571 | B2 | 2/2008 | Miao et al. |
| 7,385,028 | B2 | 6/2008 | Miao et al. |
| 7,723,476 | B2 | 5/2010 | Skerra et al. |
| 7,959,929 | B2 | 6/2011 | Crawford et al. |
| 8,158,753 | B2 | 4/2012 | Skerra et al. |
| 8,637,456 | B2 | 1/2014 | Sasisekharan et al. |
| 8,680,022 | B2 | 3/2014 | Gregory et al. |
| 8,685,402 | B2 | 4/2014 | Lanzavecchia |
| 8,871,207 | B2 | 10/2014 | Lanzavecchia |
| 9,683,030 | B2 * | 6/2017 | Raguram ............. A61P 31/16 |
| 9,982,037 | B2 * | 5/2018 | Raguram ............. A61P 31/16 |
| 10,538,578 | B2 * | 1/2020 | Raguram ............. A61P 31/16 |
| 2005/0106660 | A1 | 5/2005 | Vogt et al. |
| 2006/0058510 | A1 | 3/2006 | Skerra et al. |
| 2006/0088908 | A1 | 4/2006 | Skerra et al. |
| 2008/0075736 | A1 | 3/2008 | Crawford et al. |
| 2008/0241918 | A1 | 10/2008 | Sasisekharan et al. |
| 2009/0081193 | A1 | 3/2009 | Sasisekharan et al. |
| 2009/0092620 | A1 | 4/2009 | Moste et al. |
| 2009/0269342 | A1 | 10/2009 | Sasisekharan et al. |
| 2010/0061990 | A1 | 3/2010 | Sasisekharan et al. |
| 2010/0285564 | A1 | 11/2010 | Skerra et al. |
| 2010/0317547 | A1 | 12/2010 | Gregory et al. |
| 2011/0201547 | A1 | 8/2011 | Sasisekharan et al. |
| 2011/0274702 | A1 | 11/2011 | Lanzavecchia |
| 2013/0302348 | A1 | 11/2013 | Raguram et al. |
| 2017/0306003 | A1 | 10/2017 | Raguram et al. |
| 2019/0062407 | A1 | 2/2019 | Raguram et al. |

FOREIGN PATENT DOCUMENTS

| | | |
|---|---|---|
| CN | 101848719 A | 9/2010 |
| CN | 102164613 A | 8/2011 |
| CN | 102216327 A | 10/2011 |
| EP | 0932625 A1 | 8/1999 |
| EP | 1167382 A1 | 1/2002 |
| EP | 1489101 A1 | 12/2004 |
| JP | H07-304799 A | 11/1995 |
| JP | 2011-528901 A | 12/2011 |
| JP | 6-247995 B2 | 12/2017 |
| KR | 10-20110047193 A | 5/2011 |
| WO | WO-91/11465 A1 | 8/1991 |
| WO | WO-1997/013537 A1 | 4/1997 |
| WO | WO-1997/037705 A1 | 10/1997 |
| WO | WO-99/34850 A1 | 7/1999 |
| WO | WO-00/59932 A1 | 10/2000 |
| WO | WO-03/074570 A1 | 9/2003 |
| WO | WO-03/080672 A1 | 10/2003 |
| WO | WO-2004/018698 A2 | 3/2004 |
| WO | WO-2006/051069 A3 | 5/2006 |
| WO | WO-2006/056464 A2 | 6/2006 |
| WO | WO-2007/0019094 A2 | 2/2007 |
| WO | WO-2008/073161 A2 | 6/2008 |
| WO | WO-2009/002516 A1 | 12/2008 |
| WO | WO-2009/079259 A2 | 6/2009 |
| WO | WO-2009/089121 A2 | 7/2009 |
| WO | WO-2010/010466 A2 | 1/2010 |
| WO | WO-2011/094445 A1 | 8/2011 |
| WO | WO-2011/137245 A2 | 11/2011 |
| WO | WO-2012/047941 A2 | 4/2012 |
| WO | WO-2013/169377 A1 | 11/2013 |

OTHER PUBLICATIONS

Altschul, et al., Local Alignment Statistics, Methods in Enzymology, 266(27):460-480 (1996).

Ausubel et al., eds, Current Protocols in Molecular Biology (1990).

Baxevanis, et al., Bioinformatics : A Practical Guide to the Analysis of Genes and Proteins, Wiley, (1998).

Baylor et al., Aluminum salts in vaccines—US perspective, Vaccine, 20:S18 (2002).

Belser, J.A. et al., Effect of D222G mutation in the hemagglutinin protein on receptor binding, pathogenesis and transmissibility of the 2009 pandemic H1N1 influenza virus, PLoS One, 6(9):e25091, 8 pages (2011).

Bresson et al., Safety and immunogenicity of an inactivated split-virion influenza A/Vietnam/1194/2004 (H5N1) vaccine: phase I randomized trial, Lancet, 367:1657 (2006).

Cao et al., Enhancement of the protective effect of inactivated influenza virus vaccine by cytokines, Vaccine, 10:238 (1992).

Chandrasekaran, et al., Glycan topology determines human adaptation of avian H5N1 virus hemagglutinin, Nature Biotechnology, 26(1):107-113 (2008).

Clementi, N. et al., A Human Monoclonal Antibody with Neutralizing Activity against highly Divergent Influenza Subtypes, PLoS One, 6(12): 1-10 (2011).

Collins et al., Crystal structures of oseltamivir-resistant influenza virus neuraminidase mutants, Nature 453(7199):1258-1261 (2008).

Connor et al., Receptor Specificity in Human, Avian, and Equine H2 and H3 Influenza Virus Isolates, Virology, 205:17, 1994.

Cooper et al., Safety and immunogenicity of CPG 7909 injection as an adjuvant to Fluarix influenza vaccine, Vaccine, 22:3136, 2004.

Corti, D. et al., A neutralizing antibody selected from plasma cells that binds to group 1 and group 2 influenza A hemagglutinins, Science, 333:850-856 (2011).

Cumber et al., Comparative Stabilities in vitro and in vivo of a recombinant mouse antibody FvCys fragment and a bisFvCys conjuigate, J Immunology 149(1):120-126, (1992).

Daniels, et al., The receptor-binding and membrane-fusion properties of influenza virus variants selected using anti-haemagglutinin monoclonal antibodies, the EMBO Journal, 6(5):1459 (1987).

Database Accession No. AJN42458, Dbfetch, EBI, Influenza A virus neutralizing antibody VL chain protein, SEQ:57, 1 page, retrieved May 24, 2016 <http://www.ebi.ac.uk/Tools/dbfetch/dbfetch?db=uspto_prt;id=AJN42458>.

Database Accession No. G1FM93, Uniprot, SubName: Full=Anti-Influenza A hemagglutinin heavy chain variable region, 5 pages, last modified Oct. 19, 2011, retrieved May 16, 2016 <http://www.uniprot.org/uniprot/G1FM93>.

Eisen et al., Binding of the influenza A Virus to Cell-Surface Receptors. Structures of Five Hemagglutinin-Sialyloligosaccharide Complexes Determined by X-Ray Crystallography, Virology, 232:19, 1997.

Ekiert et al., Antibody recognition of a highly conserved influenza virus epitope, Science 324(5924):246-251, 2009.

Ekiert, D.C. et al., A highly conserved neutralizing epitope on group 2 influenza A viruses, Science, 333(6044):843-50 (2011).

Enserink, Pandemic Vaccine Appears to Protect Only at High Doses, Science, 309:996, 2005.

Extended European Search Report for EP 13787149.7, 9 pages (dated Dec. 4, 2015).

Extended European Search Report for EP07870741.1, 10 pages (dated Oct. 27, 2010).

Extended European Search Report for EP09701014.4, 7 pages (dated Feb. 22, 2012).

Fishwild et al., High-avidity human IgG kappa monoclonal antibodies from a novel stain of minilocus transgenic mice, Nat. Biotechnol., 14(7):845-51, 1996.

Gamblin et al., "The Structure and Receptor Binding Properties of the 1918 Influenza Hemagglutinin" Science, 303:1838, 2004.

GenBank record No. AAD13567, hemagglutinin H5, influenza A virus A/chicken/Hong Kong/786/97 (2005).

GenBank record No. AAO46804, influenza A virus A/chicken/Hong Kong/YU822.2/01 (H5N1) (2003).

GenBank Record No. ABC66574.1 (GI:84797248), Influenza A virus (A/chicken/Bantul/BBVet-I/2005(H5N1)).

Ghockhikyan et al., "Prototype Alzheimer's disease epitope vaccine induced strong Th2-type anti-ß antibody response with Alum to Quil A adjuvant switch," Vaccine, 24:2275, 2006.

(56) References Cited

OTHER PUBLICATIONS

Glaser et al., A Single Amino Acid Substitution in 1918 Influenza Virus Hemagglutinin Changes Receptor Binding Specificity, J. Virol., 79:11533 (2005).
Glick et al., Ligand Recognition by Influenza Virus the Binding of Bivalent Sialosides, J. Biol. Chem., 266(35):23660-23669 (1991).
Ha et al., X-ray structure of the hemagglutinin of a potential H3 avian progenitor of the 1968 Hong Kong pandemic influenza virus, Virology, 309:209, 2003.
Ha, et al., X-ray structures of H5 avian and H9 swine influenza virus hemagglutinins bound to avian and human receptor analogs, Proceedings of the National Academy of Science, 98(20):11181-11186 (2001).
Hemagglutinin [Influenza A virus (A_Chicken_Hong Kong_YU822. 2_01 (H5N1) (2003))].
Hemagglutinin H5 [Influenza A virus (A_Chicken_Hong Kong_786_97 (H5N1) (2005))].
Hensley, S.E. et al., Hemagglutinin receptor binding avidity drives influenza A virus antigenic drift, Science, 326(5953):734-736 (2009).
Hoogenboom et al., "Construction and Expression of Antibody-tumor Necrosis Factor Fusion Proteins," Mol Immunol., 28(9):1027-37, 1991.
Imberty et al., An Unusual Carbohydrate Binding Site Revealed by the Structures of Two Maaxkia amurensis Lectins Complexed with Sialic Acid-containing Oligosaccharides, J. Biol. Chem, 275(23):17541, 2000.
International Search Report for PCT/US07/18160, dated Sep. 3, 2008.
International Search Report for PCT/US09/30058, dated Jun. 25, 2009.
International Search Report for PCT/US2013/031704, 5 pages (dated Aug. 30, 2013).
Jayaraman, A. et al., A single base-pair change in 2009 H1N1 hemagglutinin increases human receptor affinity and leads to efficient airborne viral transmission in ferrets, PLoS One, 6(3):e17616, 8 pages (2011).
Jayaraman, A. et al., Decoding the distribution of glycan receptors for human-adapted influenza A viruses in ferret respiratory tract, PLoS One, 7(2):e27517, 8 pages (2012).
Jayaraman, A. et al., Glycosylation at Asn91 of H1 N1 haemagglutinin affects binding to glycan receptors, the Biochemical Journal, 444(3):429-435 (2012).
Jayasena, S.D., "Aptamers: An Emerging Class of Molecules That Rival Antibodies in Diagnostics," Clin. Chem., 45:1628-1650, 1999.
Katz et al., "A nonionic block co-polymer adjuvant (CRL1005) enhances the immunogenicity and protective efficacy of inactivated influenza vaccine in young and aged mice," Vaccine, 18:2177, 2000.
Khanna, et al., Emerging influenza virus: A global threat, J. Biosci. 33(4):475-482 (2008).
Kohl et al., Designed to be stable: Crystal structure of a consensus ankryrin repeat protein, PNAS, 100(4):1700-1705, (2003).
Kreuter et al., "Long-Term Studies of Microencapsulated and Adsorbed Influenza Vaccine Nanoparticles," J. Pharm. Sci., 70:367, 1981.
Kumari, et al., Receptor binding specificity of recent human H3N2 influenza virus, Virology Journal, 4(1):42 (2007).
Liao, H-X. et al, Initial antibodies binding to HIV-1 gp41 in acutely infected subjects are polyreactive and highly mutated, J. Exp. Med., 208(11): 2237-2249 (2011).
Liu et al., Antibody like eptidomimetics as large scale immunodetection probes, Cell Mol Biol (Noisy-le-grand). 49(2):209-16, (2003).
Lonberg and Huszar, "Human antibodies from transgenic mice", Int. Rev. Immunol., 13(1): 65-93, 1995.
Lonberg et al., "Antigen-specific human antibodies from mice comprising four distinct genetic modifications", Nature 368(6474):856-9, 1994.
Losman et al., "Baboon Anti-Idiotype Antibodies Mimic a Carcinoembryonic Antigen Epitope," Int. J. Cancer, 46:310, 1990.

Maines, T.R. et al., Effect of receptor binding domain mutations on receptor binding and transmissibility of avian influenza H5N1 viruses, Virology, 413(1):139-147 (2011).
Maines, T.R., et al., Transmission and Pathogenesis of Swine-Origin 2009 A(H1 N1) Influenza Viruses in Ferrets and Mice, Science, 325(5939):484-487 (2009).
Marks et al., "By-passing immunization: building high affinity human antibodies by chain shuffling", Biotechnology (NY), 10(7):779-83, 1992.
Marks et al., "By-passing Immunization: Human Antibodies from V-gene Libraries Displayed on Phage," J Mol Biol., 222(3):581-97, 1991.
Mbwuike et al., "Enhancement of the protective efficacy of inactivated influenza a virus vaccine in aged mice by IL-2 liposomes," Vaccine, 8:347, 1990.
Milstein and Cuello, "Hybrid hybridomas and their use in immunohistochemistry," Nature 305(5934):537-40, 1983.
Misener, et al., Bioinformatics Methods and Protocols (Methods in Molecular Biology) 132, Humana Press, (1999).
Mostow et al., "Application of the Single Radial Diffusion Test for Assay of Antibody to Influenza Type A Viruses," J. Clin. Microbiol., 2:531, 1975.
NCBI website, protein Blast of GenBank Record No. ABW74701.1 (GI:158604860), Influenza A virus (A/Indonesia/TLL001/2006(H5N1)), (http://blast.ncbi.nlm.nih.gov/Blast.gi) (Oct. 28, 2011).
O'Shannessy et al., Site-directed immobilization of glycoproteins on hydrazide-containing solid supports, Biotechnol. Appl. Biochem. 9: 488-496 (1987).
Pack et al., Miniantibodies: Use of Amphipathic Helices to Produce Functional, Flexibly Linked Dimeric Fv Fragments with High Avidity in *Escherichia coli*, Biochemistry 31(6):1579-1584, (1992).
Pappas, C. et al., Receptor specificity and transmission of H2N2 subtype viruses isolated from the pandemic of 1957, PLoS One, 5(6):11158, 10 pages (2010).
Payne et al., "Poly[di(carboxylataphenoxy)phosphazene] (PCPP) is a potent immunoadjuvant for an influenza vaccine," Vaccine, 16:92, 1998.
Pearce, M.B. et al., Pathogenesis and transmission of swine origin A(H3N2)v influenza viruses in ferrets, Proceedings of the National Academy of Science, 109(10):3944-3949 (2012).
Phillips et al., Enhanced antibody response to lipsome-associated protein antigens: preferential stimulation of IgG2a/b production, Vaccine, 10(3):151-158, (1992).
Pielak et al., Mechanism of drug inhibition and drug resistance of influenza A M2 channel, PNAS, Dept of Biol Chem and Mol Pharm and Prog in Biol Biomed Sciences, 106(18):7379, (2009).
Reisfeld and Sell, "Human tumour-associated antigens: targets for monoclonal antibody-mediated cancer therapy," Cancer Surv., 4(1):271-90, 1985.
Restituyo, J.A. et al., Conversion of Aryl Azides to O-Alkyl Imidates via Modified Staudinger Ligation, Organic Letters, 5(23): 4357-4360 (2003).
Riechmann et al., "Reshaping human antibodies for therapy," Nature 332(6162):323-7, 1988.
Rogers & Paulson, "Receptor Determinants of Human and Animal Influenza Virus Isolates: Differences in Receptor Specificity of the H3 Hemagglutinin Based on Species of Origin," Virology, 127:361, 1983.
Rogers, et al., "Single amino acid substitutions in influenza haemagglutinin change receptor binding specificity," *Nature*, 304:76, (1983).
Rudikoff, S. et al., Single amino acid substitution altering antigen-binding specificity, Proc. Natl. Acad. Sci. USA, 79(6):1979-83 (1982).
Russell et al., "H1 and H7 influenza haemagglutinin structures extend a structural classification of haemagglutinin subtypes," *Virology*, 325:287, (2004).
Russell, et al., "Avian and human receptor binding by hemagglutinins of influenza A viruses," *Glycoconj J.*, 23:85, (2006).
Sauter et al., "Binding of Influenza Virus Hemagglutinin to Analogs of Its Cell-Surface Receptor, Sialic Acid: Analysis by Proton Nuclear Magnetic Resonance Spectroscopy and X-ray Crystallography," Biochemistry, 31:9609, 1992.

(56) References Cited

OTHER PUBLICATIONS

Schild et al., "Single-radial-haemolysis: a new method for the assay of antibody to influenza haemagglutinin," Bull. World Health Organ., 52:43-50 & 223-31, 1975.
Shriver et al., Design of a Broadly Neutralizing Antibody Targeting Influenza A, Visterra, Inc. (2012) [retrieved from the Internet Aug. 18, 2013: http://www.visterrainc.com/pdf/ICAAC-VIS410-Presentation-Final-10Sept2012.pdf ].
Shriver, Z., et al., Context-Specific Target Definition in Influenza A Virus Hemagglutinin-Glycan Receptor Interactions, Chemistry & Biology, 16:803-814 (2009).
Skehel & Wiley, "Receptor Binding and Membrane Fusion in Virus Entry: The Influenza Hemagglutinin," Annu Rev Biochem, 69:531, 2000.
Skerra A., Engineered protein scaffolds for molecular recognition, J. Mol. Recognit. 13:167-187, (2000).
Skerra A.,Anticalins: a new class of engineered ligand-binding proteins with antibody-like properties, Reviews in Molecular Biotechnology, 74(4):257-275, (2001).
Soundararajan et al., Extrapolating from sequence—the 2009 H1N1 'swine' influenza virus, Nature Biotechnology 27:510, (2009).
Soundararajan, V. et al., Networks link antigenic and receptor-binding; sites of influenza hemagglutinin: mechanistic insight into fitter strain; propagation, Scientific Reports, 1:200 (2011).
Srinivasan et al., Quantitative Description of Glycan-Receptor Binding of Influenza A Virus H7 Hemagglutinin, PLOS One, 8(2):e49597, 7 pages (2013).
Srinivasan, A. et al., Quantitative biochemical rationale for differences in transmissibility of 1918 pandemic influenza A viruses, PNAS, 105(8):2800-2805 (2008).
St-Amour, I. et al., Modulations of anti-D affinity following promiscuous binding of the heavy chain with naive light chains, Transfusion, 43:246-253 (2003).
Stevens et al., "Structure of the Uncleaved Human H1 Hemagglutinin from the Extinct 1918 Influenza Virus," Science, 303:1866, 2004.
Stevens, et al., "Structure and Receptor Specificity of the Hemagglutinin from an H5N1 Influenza Virus" *Science* 312:404, (2006).
Stevens, et al., Glycan Microarray Analysis of the Hemagglutinins from Modern and Pandemic Influenza Viruses Reveals Different Receptor Specificities, J. Mol. Biol. 355: 1143-1155 (2006).
Stouffer et al., Structural basis for the function and inhibition of an influenza virus proton channel, Nature, 451:596-599, (2008).
Sui, J. et al., Structural and Functional Bases for Broad-Spectrum Neutralization of Avian and Human Influenza A Viruses, Nat. Struct. Mol. Biol., 16(3):265-273 (2009).
Sui, J. et al., Wide prevalence of heterosubtypic broadly neutralizing; human anti-influenza A antibodies, Clinical Infectious Diseases, 52(8):1003-9 (2011).
Tan, G.S. et al., A pan-H1; anti-hemagglutinin monoclonal antibody with potent broad-spectrum efficacy in; vivo, Journal of Virology, 86(11):6179-88 (2012).
Tharakaraman, K. et al., Redesign of a cross-reactive antibody to dengue virus with broad-spectrum activity and increased in vivo potency, Proc. Natl. Acad. Sci. U S A., 110(17):E1555-64 (2013).
Treanor et al., "Safety and Immunogenicity of an Inactivated Subvirion Influenza A (H5N1) Vaccine," N. Eng J. Med., 354:1343, 2006.
Tuerk, C., and Gold, L., "Systematic Evolution of Ligands by Exponential Enrichment: RNA Ligands to Bacteriophage T4 DNA Polymerase," Science 249:505-510, 1990.
Tumpey et al., "Characterization of the Reconstructed 1918 Spanish Influenza Pandemic Virus," Science, 310:77, 2005.
Tumpey, et al., A Two-amino acid change in the hemagglutinin of the 1918 Influenza virus abolishes transmission, Science, 315:655-659 (2007).
Unkeless et al., Structure and function of human and murine receptors for IgG, Ann. Rev. Immunol., 6:251-281 (1988).
Van Hoeven, N. et al., Human HA and polymerase subunit PB2 proteins confer transmission of an avian influenza virus through the air, Proc. Natl. Acad. Sci. U S A., 106(9):3366-71 (2009).
Verhoeyen et al., "Reshaping Human Antibodies: Grafting an Antilysozyme Activity," Science, 239(4847):1534-6, 1988.
Viswanathan, et al., Glycans as receptors for influenza pathogenesis, Glycoconjugate Journal, 27(6):561-570 (2010).
Viswanathan, K. et al., Determinants of Glycan Receptor Specificity of H2N2 Influenza a Virus Hemagglutinin, PLoS One, 5(10):e13768, 9 pages (2010).
Vasquez, M. et al, Connecting the sequence dots: shedding light on the genesis of antibodies reported to be designed in silico, mAbs, DOI: 10.1080/19420862.2019.1611172, 1-6 (2019).
Wang et al., "Expression and purification of an influenza hemagglutinin—one step closer to a recombinant protein-based influenza vaccine," Vaccine, 24:2176, 2006.
Wang, T.T. et al., Broadly ; protective monoclonal antibodies against H3 influenza viruses following; sequential immunization with different hemagglutinins, PLoS Pathogens, 6(2):e1000796 (2010).
Wrammert, J. et al., Broadly cross-reactive antibodies dominate the human B cell response against 2009; pandemic H1N1 influenza virus infection, Journal of Experimental Medicine, 208(1):181-93 (2011), Erratum in: Journal Experimental Medicine, 208(2):411 (2011).
Written Opinion for PCT/US07/18160, dated Sep. 3, 2008.
Written Opinion for PCT/US09/30058, dated Jun. 25, 2009.
Written Opinion for PCT/US2013/031704, 5 pages (dated Aug. 30, 2013).
Yamada, et al., "Haemagglutinin mutations responsible for the binding of H5N1 influenza A viruses to human-type receptors," *Nature*, 444:378, (2006).
Yang, et al., Immunization by Avian H5 Influenza Hemagglutinin Mutants with Altered Receptor Binding Specify Science, 317:825 (2007).
Yoshida, R. et al., Cross-protective potential of a novel monoclonal antibody directed against antigenic site b of the hemagglutinin of influenza A viruses, PLoS Pathogens, 5(3):1-9 (2009).
Tamura, M. et. al., Structural Correlates of an Anticarcinoma Antibody: Identification of Specificity-Determining Residues (SDRs) and Development of a Minimally Immunogenic Antibody Variant by Retention of SDRs Only, the Journal of Immunology, 164(3):1432-41, (2000).

\* cited by examiner

Figure 3C

CDR Residues Are In Bold

Heavy chain sequences

```
VH1     EVQLLESGGGLVKPGQSLKLSCAASGFTFTSYGMHWVRQPPGKGLEWVAVISYDGSYKYY
VH2     EVQLLESGGGVVQPGRSLKLSCAASGFTFSSYGMHWVRQAPGKGLEWVAVISYDGSNKYY
VH3     EVQLLESGGGVVQPGRSLKLSCAASGFTFSSYGMHWVRQAPGKGLEWVAVVSYDGSNKYY
VH4     EVQLLESGGGVVQPGRSLKLSCAASGFTFSSYGMHWVRQAPGKGLEWVAVVSYDGSNKYY
VH5     EVQLLESGGGLVKPGQSLKLSCAASGFTFSSYGMHWVRQPPGKGLEWVAVVSYDGSNKYY
VH6     EVQLLESGGGLVKPGQSLKLSCAASGFTFSSYGMHWVRQPPGKGLEWVAVVSYDGSNKYY
VH7     EVQLLESGGGLVKPGQSLKLSCAASGFTFSSYGMHWVRQPPGKGLEWVAVVSYDGSNKYY
VH8     EVQLLESGGGLVKPGQSLKLSCAASGFTFSSYGMHWVRQPPGKGLEWVAVVSYDGSNKYY
VH9     EVQLLESGGGLVKPGQSLKLSCAASGFTFSSYGMHWVRQPPGKGLEWVAVVSYDGSNKYY
VH10    EVQLLESGGGLVKPGQSLKLSCAASGFTFSSYGMHWVRQPPGKGLEWVAVVSYDGSNKYY
VH11    EVQLLESGGGLVKPGQSLKLSCAASGFTFSSYGMHWVRQPPGKGLEWVAVVSYDGSYKYY
VH12    EVQLLESGGGLVKPGQSLKLSCAASGFTFTSYGMHWVRQPPGKGLEWVAVISYDGSYKYY
VH13    EVQLLESGGGLVKPGQSLKLSCAASGFTFTSYGMHWVRQPPGKGLEWVAVISYDGSYKYY
VH14    EVQLLESGGGLVKPGQSLKLSCAASGFTFTSYGMHWVRQPPGKGLEWVAVISYDGSYKYY
VH15    EVQLLESGGGLVKPGQSLKLSCAASGFTFTSYGMHWVRQPPGKGLEWVAVISYDGSYKYY
VH16    EVQLLESGGGLVKPGQSLKLSCAASGFTFTSYGMHWVRQPPGKGLEWVAVISYDGSYKYY

VH1     ADSVQGRFTISRDNSKNTLYLQMNSLRAEDTAVYYCAKDSELRSLLYFEWLSQGYFNPWG
VH2     ADSVEGRFTISRDNSKNTLYLQMNSLRAEDTAVYYCAKDGKLRSLLYFEWLSSGLLDYWG
VH3     ADSVEGRFTISRDNSKNTLYLQMNSLRAEDTAVYYCAKDGKLRSLLYFEWLSSGLLDYWG
VH4     APKFEGRFTISRDNSKNTLYLQMNSLRAEDTAVYYCAKDGKLRSLLYFEWLSSGLLDYWG
VH5     ADSVQGRFTISRDNSKNTLYLQMNSLRAEDTAVYYCAKDGKLRSLLYFEWLSSGLLDYWG
VH6     ADSVQGRFTISRDNSKNTLYLQMNSLRAEDTAVYYCGKDSQLRSLVYFEWLSSGLLDYWG
VH7     ADSVQGRFTISRDNSKNTLYLQMNSLRAEDTAVYYCAKDSQLRSLLYFEWLSSGLLDYWG
VH8     ADSVQGRFTISRDNSKNTLYLQMNSLRAEDTAVYYCAKDSKLRSLLYFEWLSSGLLDYWG
VH9     ADSVQGRFTISRDNSKNTLYLQMNSLRAEDTAVYYCAKDTQLRTIVYFEWLSQGFYDIWG
VH10    ADSVQGRFTISRDNSKNTLYLQMNSLRAEDTAVYYCAKDSQLRTIVYFEWLSQGYFDPWG
VH11    ADSVQGRFTISRDNSKNTLYLQMNSLRAEDTAVYYCAKDSQLRSLLYFEWLSSGLLDYWG
VH12    ADSVQGRFTISRDNSKNTLYLQMNSLRAEDTAVYYCGKDSQLRSLIYFEWLSNGYFDIWG
VH13    ADSVQGRFTISRDNSKNTLYLQMNSLRAEDTAVYYCAKDSQLRSLLYFEWLSNGFYDIWG
VH14    ADSVQGRFTISRDNSKNTLYLQMNSLRAEDTAVYYCAKDSNLRTIVYFEWLSSGLLDYWG
VH15    ADSVQGRFTISRDNSKNTLYLQMNSLRAEDTAVYYCAKDSQLRTIVYFEWLSQGYFDPWG
VH16    ADSVQGRFTISRDNSKNTLYLQMNSLRAEDTAVYYCAKDTQLRTIVYFEWLSQGFYDIWG

VH1     AGTTLTVSSASTK
VH2     QGAMVTVSSASTK
VH3     QGAMVTVSSASTK
VH4     QGAMVTVSSASTK
VH5     QGAMVTVSSASTK
VH6     QGAMVTVSSASTK
VH7     QGAMVTVSSASTK
VH8     QGAMVTVSSASTK
VH9     QGAMVTVSSASTK
VH10    QGAMVTVSSASTK
VH11    QGAMVTVSSASTK
VH12    AGTTLTVSSASTK
VH13    AGTTLTVSSASTK
VH14    AGTTLTVSSASTK
VH15    AGTTLTVSSASTK
VH16    AGTTLTVSSASTK
```

Figure 10A

CDR Residues Are in Bold

Light chain sequences

```
VL1   EIVMTQSPDSLAVSLGERATINCKSSQSVTYNYKNYLAWYQQKPGQPPKLLIYWASTR
VL2   DIQMTQSPSSLSASVGDRVTITCRASQDV---NTAVAWYQQKPGKAPKLLIYSASFL
VL3   DIQMTQSPSSLSASVGDRVTITCRASQDIPRSIGYVAWYQQKPGKAPKLLIYWGSYL
VL4   DIQMTQSPSSLSASVGDRVTITCRASQDIPFSYKGYVAWYQQKPGKAPKLLIYWGSYL
VL5   DIQMTQSPSSLSASVGDRVTITCRASQSITFDYKNYVAWYQQKPGKAPKLLIYWGSYL
VL6   DIQMTQSPSSLSASVGDRVTITCRASQSITFNYKNYVAWYQQKPGKAPKLLIYWGSYL
VL7   DIQMTQSPSSLSASVGDRVTITCRASQSITFSYKNYVAWYQQKPGKAPKLLIYWGSYL
VL8   DIQMTQSPSSLSASVGDRVTITCRASQDIPFSYKGYVAWYQQKPGKAPKVLIYWGSYL
VL9   DIQMTQSPSSLSASVGDRVTITCRASQSITFDYKNYVAWYQQKPGKAPKVLIYWGSYL
VL10  DIQMTQSPSSLSASVGDRVTITCRASQSITFNYKNYVAWYQQKPGKAPKVLIYWGSYL
VL11  DIQMTQSPSSLSASVGDRVTITCRASQSITFSYKNYVAWYQQKPGKAPKVLIYWGSYL

VL1   ESGVPDRFSGSGSGTDFTLTISSLQAEDVAVYYCQQYYRTPPTFGGGTKLDIKGS
VL2   YSGVPSRFSGSGSRSGTDFTLTISSLQPEDFATYYCQQHYTTPPTFGQGTKVEIKGS
VL3   YSGVPSRFSGSGSRSGTDFTLTISSLQPEDFATYYCQQHYTTPPTFGQGTKVEIKGS
VL4   ESGVPSRFSGSGSGTDFTLTISSLQPEDFATYYCQQHYTTPPTFGQGTKVEIKGS
VL5   E-GVPSRFSGSGSGTDFTLTISSLQPEDFATYYCQQHYTTPPTFGQGTKVEIKGS
VL6   ESGVPSRFSGSGSGTDFTLTISSLQPEDFATYYCQQHYTTPPTFGQGTKVEIKGS
VL7   ESGVPSRFSGSGSGTDFTLTISSLQPEDFATYYCQQHYTTPPTFGQGTKVEIKGS
VL8   ESGVPSRFSGSGSGTDFTLTISSLQPEDFATYYCQQHYTTPPTFGQGTKVEIKGS
VL9   ESGVPSRFSGSGSGTDFTLTISSLQPEDFATYYCQQHYTTPPTFGQGTKVEIKGS
VL10  ESGVPSRFSGSGSGTDFTLTISSLQPEDFATYYCQQHYTTPPTFGQGTKVEIKGS
VL11  ESGVPSRFSGSGSGTDFTLTISSLQPEDFATYYCQQHYTTPPTFGQGTKVEIKGS
```

Figure 10B

SEQUENCE LISTING

```
<160> NUMBER OF SEQ ID NOS: 60

<210> SEQ ID NO 1
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 1

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95
Ala Lys Asp Ser Glu Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
            115                 120                 125

Ser Ala Ser Thr Lys
            130

<210> SEQ ID NO 2
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 2

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
            115                 120                 125

Ser Ala Ser Thr Lys
            130

<210> SEQ ID NO 3
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 3

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Val Ser Tyr Asp Gly Ser Asn Lys Tyr Tyr Ala Asp Ser Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Leu Arg Ser Leu Leu Tyr Phe Glu Trp Leu Ser
            100                 105                 110
```

```
Ser Gly Leu Leu Asp Tyr Trp Gly Gln Gly Ala Met Val Thr Val Ser
            115                 120                 125

Ser Ala Ser Thr Lys
            130

<210> SEQ ID NO 4
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 4

Glu Val Gln Leu Leu Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Val Ser Tyr Asp Gly Ser Asn Lys Tyr Tyr Ala Pro Lys Phe
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
            115                 120                 125

Ser Ala Ser Thr Lys
            130

<210> SEQ ID NO 5
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 5

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
            115                 120                 125

Ser Ala Ser Thr Lys
            130
```

<210> SEQ ID NO 6
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 6

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Asp Ser Gln Leu Arg Ser Leu Val Tyr Phe Glu Trp Leu Ser
            100                 105                 110

Ser Gly Leu Leu Asp Tyr Trp Gly Gln Gly Ala Met Val Thr Val Ser
        115                 120                 125

Ser Ala Ser Thr Lys
    130

<210> SEQ ID NO 7
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 7

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser Ala Ser Thr Lys
    130

<210> SEQ ID NO 8
<211> LENGTH: 133
<212> TYPE: PRT

```
<213> ORGANISM: Artificial Sequence
<220> FEATURE:
<223> OTHER INFORMATION: Exemplary VH Chain

<400> SEQUENCE: 8

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser Ala Ser Thr Lys
        130

<210> SEQ ID NO 9
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 9

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Asp Thr Gln Leu Arg Thr Ile Val Tyr Phe Glu Trp Leu Ser
            100                 105                 110

Gln Gly Phe Tyr Asp Ile Trp Gly Gln Gly Ala Met Val Thr Val Ser
        115                 120                 125

Ser Ala Ser Thr Lys
        130

<210> SEQ ID NO 10
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 10
```

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Thr Ile Val Tyr Phe Glu Trp Leu Ser
            100                 105                 110

Gln Gly Tyr Phe Asp Pro Trp Gly Gln Gly Ala Met Val Thr Val Ser
        115                 120                 125

Ser Ala Ser Thr Lys
        130

<210> SEQ ID NO 11
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 11

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser Ala Ser Thr Lys
        130

<210> SEQ ID NO 12
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 12

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr

```
                    20                  25                  30

Gly Met His Trp Val Arg Gln Pro Pro Gly Lys Gly Leu Glu Trp Val
            35                  40                  45

Ala Val Ile Ser Tyr Asp Gly Ser Tyr Lys Tyr Tyr Ala Asp Ser Val
        50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Gly Lys Asp Ser Gln Leu Arg Ser Leu Ile Tyr Phe Glu Trp Leu Ser
            100                 105                 110

Asn Gly Tyr Phe Asp Ile Trp Gly Ala Gly Thr Thr Leu Thr Val Ser
        115                 120                 125

Ser Ala Ser Thr Lys
        130

<210> SEQ ID NO 13
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 13

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
            35                  40                  45

Ala Val Ile Ser Tyr Asp Gly Ser Tyr Lys Tyr Tyr Ala Asp Ser Val
        50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Asn Gly Phe Tyr Asp Ile Trp Gly Ala Gly Thr Thr Leu Thr Val Ser
        115                 120                 125

Ser Ala Ser Thr Lys
        130

<210> SEQ ID NO 14
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 14

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
            35                  40                  45
```

```
Ala Val Ile Ser Tyr Asp Gly Ser Tyr Lys Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Leu Arg Thr Ile Val Tyr Phe Glu Trp Leu Ser
            100                 105                 110

Ser Gly Leu Leu Asp Tyr Trp Gly Ala Gly Thr Thr Leu Thr Val Ser
        115                 120                 125

Ser Ala Ser Thr Lys
        130

<210> SEQ ID NO 15
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 15

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
                 20                  25                  30

Gly Met His Trp Val Arg Gln Pro Pro Gly Lys Gly Leu Glu Trp Val
             35                  40                  45

Ala Val Ile Ser Tyr Asp Gly Ser Tyr Lys Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Thr Ile Val Tyr Phe Glu Trp Leu Ser
            100                 105                 110

Gln Gly Tyr Phe Asp Pro Trp Gly Ala Gly Thr Thr Leu Thr Val Ser
        115                 120                 125

Ser Ala Ser Thr Lys
        130

<210> SEQ ID NO 16
<211> LENGTH: 133
<212> TYPE: PRT
<213> ORGANISM: Artificial Sequence
<220> FEATURE:
<223> OTHER INFORMATION: Exemplary VH Chain

<400> SEQUENCE: 16

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
                 20                  25                  30

Gly Met His Trp Val Arg Gln Pro Pro Gly Lys Gly Leu Glu Trp Val
             35                  40                  45

Ala Val Ile Ser Tyr Asp Gly Ser Tyr Lys Tyr Ala Asp Ser Val
 50                  55                  60

Gln Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Lys Asp Thr Gln Leu Arg Thr Ile Val Tyr Phe Glu Trp Leu Ser
            100                 105                 110

Gln Gly Phe Tyr Asp Ile Trp Gly Ala Gly Thr Thr Leu Thr Val Ser
        115                 120                 125

Ser Ala Ser Thr Lys
    130

<210> SEQ ID NO 17
<211> LENGTH: 7
<212> TYPE: PRT
<213> ORGANISM: Artificial Sequence
<220> FEATURE:
<223> OTHER INFORMATION: Exemplary VH Chain CDR 1

<400> SEQUENCE: 17

Gly Phe Thr Phe Thr Ser Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Exemplary VH Chain CDR 1

<400> SEQUENCE: 18

Gly Phe Thr Phe Ser Ser Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Exemplary VH Chain CDR 2

<400> SEQUENCE: 19

Ser Tyr Asp Gly Ser Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Exemplary VH Chain CDR 2

<400> SEQUENCE: 20

Ser Tyr Asp Gly Ser Asn
1               5

<210> SEQ ID NO 21
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 21

Asp Ser Glu Leu Arg Ser Leu Leu Tyr Phe Glu Trp Leu Ser Gln Gly
1               5                   10                  15

Tyr Phe Asn Pro

```
<210> SEQ ID NO 22
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 22

Asp Gly Lys Leu Arg Ser Leu Leu Tyr Phe Glu Trp Leu Ser Ser Gly
1               5                   10                  15

Leu Leu Asp Tyr
            20

<210> SEQ ID NO 23
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 23

Asp Ser Gln Leu Arg Ser Leu Val Tyr Phe Glu Trp Leu Ser Ser Gly
1               5                   10                  15

Leu Leu Asp Tyr
            20

<210> SEQ ID NO 24
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 24

Asp Ser Gln Leu Arg Ser Leu Leu Tyr Phe Glu Trp Leu Ser Ser Gly
1               5                   10                  15

Leu Leu Asp Tyr
            20

<210> SEQ ID NO 25
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 25

Asp Thr Gln Leu Arg Thr Ile Val Tyr Phe Glu Trp Leu Ser Gln Gly
1               5                   10                  15

Phe Tyr Asp Ile
            20

<210> SEQ ID NO 26
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 26

Asp Ser Gln Leu Arg Thr Ile Val Tyr Phe Glu Trp Leu Ser Gln Gly
1               5                   10                  15
```

```
Tyr Phe Asp Pro
            20

<210> SEQ ID NO 27
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 27

Asp Ser Gln Leu Arg Ser Leu Leu Tyr Phe Glu Trp Leu Ser Ser Gly
1               5                   10                  15

Leu Leu Asp Tyr
            20

<210> SEQ ID NO 28
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 28

Asp Ser Gln Leu Arg Ser Leu Ile Tyr Phe Glu Trp Leu Ser Asn Gly
1               5                   10                  15

Tyr Phe Asp Ile
            20

<210> SEQ ID NO 29
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 29

Asp Ser Gln Leu Arg Ser Leu Leu Tyr Phe Glu Trp Leu Ser Asn Gly
1               5                   10                  15

Phe Tyr Asp Ile
            20

<210> SEQ ID NO 30
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 30

Asp Ser Asn Leu Arg Thr Ile Val Tyr Phe Glu Trp Leu Ser Ser Gly
1               5                   10                  15

Leu Leu Asp Tyr
            20

<210> SEQ ID NO 31
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 31

Asp Ser Gln Leu Arg Thr Ile Val Tyr Phe Glu Trp Leu Ser Gln Gly
1               5                   10                  15
```

Tyr Phe Asp Pro
            20

<210> SEQ ID NO 32
<211> LENGTH: 20
<212> TYPE: PRT
<213> ORGANISM: Artificial Sequence
<220> FEATURE:
<223> OTHER INFORMATION: Exemplary VH Chain CDR 3

<400> SEQUENCE: 32

Asp Thr Gln Leu Arg Thr Ile Val Tyr Phe Glu Trp Leu Ser Gln Gly
1               5                   10                  15

Phe Tyr Asp Ile
            20

<210> SEQ ID NO 33
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 33

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
            100                 105                 110

Ser

<210> SEQ ID NO 34
<211> LENGTH: 109
<212> TYPE: PRT
<213> ORGANISM: Artificial Sequence
<220> FEATURE:
<223> OTHER INFORMATION: Exemplary VL Chain

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro

```
                     85                  90                  95

Thr Phe Gly Gln Gly Thr Lys Val Glu Ile Lys Gly Ser
            100                 105

<210> SEQ ID NO 35
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro Arg Ser
            20                  25                  30

Ile Ser Gly Tyr Val Ala Trp Tyr Gln Gln Lys Pro Gly Lys Ala Pro
        35                  40                  45

Lys Leu Leu Ile Tyr Trp Gly Ser Tyr Leu Tyr Ser Gly Val Pro Ser
    50                  55                  60

Arg Phe Ser Gly Ser Arg Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Gly
            100                 105                 110

Ser

<210> SEQ ID NO 36
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro Phe Ser
            20                  25                  30

Tyr Lys Gly Tyr Val Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Gly
            100                 105                 110

Ser

<210> SEQ ID NO 37
<211> LENGTH: 112
<212> TYPE: PRT
<213> ORGANISM: Artificial Sequence
<220> FEATURE:
<223> OTHER INFORMATION: Exemplary VL Chain
```

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Asp
            20                  25                  30

Tyr Lys Asn Tyr Val Ala Trp Tyr Gln Gln Lys Pro Gly Lys Ala Pro
        35                  40                  45

Lys Leu Leu Ile Tyr Trp Gly Ser Tyr Leu Glu Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Gly Ser
            100                 105                 110

<210> SEQ ID NO 38
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Asn
            20                  25                  30

Tyr Lys Asn Tyr Val Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Gly
            100                 105                 110

Ser

<210> SEQ ID NO 39
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Ser
            20                  25                  30

Tyr Lys Asn Tyr Val Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser

```
                65                  70                  75                  80
Ser Leu Gln Pro Glu Asp Phe Ala Thr Tyr Tyr Cys Gln Gln His Tyr
                    85                  90                  95

Thr Thr Pro Pro Thr Phe Gly Gln Gly Thr Lys Val Glu Ile Lys Gly
                100                 105                 110

Ser

<210> SEQ ID NO 40
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro Phe Ser
                20                  25                  30

Tyr Lys Gly Tyr Val Ala Trp Tyr Gln Gln Lys Pro Gly Lys Ala Pro
            35                  40                  45

Lys Val Leu Ile Tyr Trp Gly Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                    85                  90                  95

Thr Thr Pro Pro Thr Phe Gly Gln Gly Thr Lys Val Glu Ile Lys Gly
                100                 105                 110

Ser

<210> SEQ ID NO 41
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Asp
                20                  25                  30

Tyr Lys Asn Tyr Val Ala Trp Tyr Gln Gln Lys Pro Gly Lys Ala Pro
            35                  40                  45

Lys Val Leu Ile Tyr Trp Gly Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                    85                  90                  95

Thr Thr Pro Pro Thr Phe Gly Gln Gly Thr Lys Val Glu Ile Lys Gly
                100                 105                 110

Ser

<210> SEQ ID NO 42
<211> LENGTH: 113
```

<212> TYPE: PRT
<213> ORGANISM: Artificial Sequence
<220> FEATURE:
<223> OTHER INFORMATION: Exemplary VL Chain

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Asn
            20                  25                  30

Tyr Lys Asn Tyr Val Ala Trp Tyr Gln Gln Lys Pro Gly Lys Ala Pro
        35                  40                  45

Lys Val Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Gly
            100                 105                 110

Ser

<210> SEQ ID NO 43
<211> LENGTH: 113
<212> TYPE: PRT
<213> ORGANISM: Artificial Sequence
<220> FEATURE:
<223> OTHER INFORMATION: Exemplary VL Chain

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Phe Ser
            20                  25                  30

Tyr Lys Asn Tyr Val Ala Trp Tyr Gln Gln Lys Pro Gly Lys Ala Pro
        35                  40                  45

Lys Val Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Gly
            100                 105                 110

Ser

<210> SEQ ID NO 44
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 44

Lys Ser Ser Gln Ser Val Thr Tyr Asn Tyr Lys Asn Tyr Leu Ala
1               5                   10                  15

<210> SEQ ID NO 45
<211> LENGTH: 11

```
<212> TYPE: PRT
<213> ORGANISM: Artificial Sequence
<220> FEATURE:
<223> OTHER INFORMATION: Exemplary VL Chain CDR 1

<400> SEQUENCE: 45

Arg Ala Ser Gln Asp Val Asn Thr Ala Val Ala
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 46

Arg Ala Ser Gln Asp Ile Pro Arg Ser Ile Ser Gly Tyr Val Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 47

Arg Ala Ser Gln Asp Ile Pro Phe Ser Tyr Lys Gly Tyr Val Ala
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 48

Arg Ala Ser Gln Ser Ile Thr Phe Asp Tyr Lys Asn Tyr Val Ala
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 49

Arg Ala Ser Gln Ser Ile Thr Phe Asn Tyr Lys Asn Tyr Val Ala
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 50

Arg Ala Ser Gln Ser Ile Thr Phe Ser Tyr Lys Asn Tyr Val Ala
1               5                   10                  15

<210> SEQ ID NO 51
<211> LENGTH: 15
<212> TYPE: PRT
```

```
<213> ORGANISM: Artificial Sequence
<220> FEATURE:
<223> OTHER INFORMATION: Exemplary VL Chain CDR 1

<400> SEQUENCE: 51

Arg Ala Ser Gln Asp Ile Pro Phe Ser Tyr Lys Gly Tyr Val Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 52

Arg Ala Ser Gln Ser Ile Thr Phe Asp Tyr Lys Asn Tyr Val Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 53

Arg Ala Ser Gln Ser Ile Thr Phe Asn Tyr Lys Asn Tyr Val Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Exemplary VL Chain CDR 1

<400> SEQUENCE: 54

Arg Ala Ser Gln Ser Ile Thr Phe Ser Tyr Lys Asn Tyr Val Ala
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Exemplary VL Chain CDR 2

<400> SEQUENCE: 55

Trp Ala Ser Thr Arg Glu Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Exemplary VL Chain CDR 2

<400> SEQUENCE: 56

Ser Ala Ser Phe Leu Tyr Ser
1               5

<210> SEQ ID NO 57
<211> LENGTH: 7
<212> TYPE: PRT
<213> ORGANISM: Artificial Sequence
```

```
<220> FEATURE:
<223> OTHER INFORMATION: Exemplary VL Chain CDR 2

<400> SEQUENCE: 57

Trp Gly Ser Tyr Leu Tyr Ser
1               5

<210> SEQ ID NO 58
<211> LENGTH: 6
<212> TYPE: PRT
<213> ORGANISM: Artificial Sequence
<220> FEATURE:
<223> OTHER INFORMATION: Exemplary VL Chain CDR 2

<400> SEQUENCE: 58

Trp Gly Ser Tyr Leu Glu
1               5

<210> SEQ ID NO 59
<211> LENGTH: 9
<212> TYPE: PRT
<213> ORGANISM: Artificial Sequence
<220> FEATURE:
<223> OTHER INFORMATION: Exemplary VL Chain CDR 3

<400> SEQUENCE: 59

Gln Gln Tyr Tyr Arg Thr Pro Pro Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Exemplary VL Chain CDR 3

<400> SEQUENCE: 60

Gln Gln His Tyr Thr Thr Pro Pro Thr
1               5
```

AGENTS FOR INFLUENZA NEUTRALIZATION

CROSS-REFERENCE TO RELATED APPLICATIONS

This application is a continuation of U.S. application Ser. No. 15/959,430, filed Apr. 23, 2018, which is a continuation of U.S. application Ser. No. 15/595,407, filed May 15, 2017 (now U.S. Pat. No. 9,982,037), which is a divisional of U.S. application Ser. No. 13/829,675, filed Mar. 14, 2013 (now U.S. Pat. No. 9,683,030), which claims the benefit under 35 U.S.C. § 119(e) of U.S. Provisional Application No. 61/645,453, filed May 10, 2012, the contents of each of which are incorporated herein by reference in their entireties.

GOVERNMENT SUPPORT

This invention was made with government support under grant number R37 GM057073 awarded by the National Institutes of Health. The government has certain rights in the invention.

SEQUENCE LISTING

The present specification makes reference to a Sequence Listing (submitted electronically as a .txt file named "Sequence Listing.txt" on Mar. 14, 2013). The .txt file was generated on Mar. 8, 2013 and is 39.3 kb in size. The entire contents of the Sequence Listing are herein incorporated by reference.

BACKGROUND OF THE INVENTION

Influenza virus is a global health threat that is responsible for over 300,000 deaths annually. The virus evades immune recognition by engaging in a combination of accelerated antigenic drift, domain reassortment, genetic recombination, and glycosylation based masking of its surface glycoproteins. This rapid mutation capability of the virus is particularly exacerbated in the context of the growing threat from the present H1N1 'swine flu' pandemic as well as the alarming worldwide spate in recent infections with highly pathogenic avian H5N1 'bird flu' influenza strains. (Khanna et al., *Journal of Biosciences*., 33(4):475, 2008, Soundararajan et al., *Nature Biotechnology* 27:510, 2009). Furthermore, two of the major flu pandemics of the last century originated from avian flu viruses that changed their genetic makeup to allow for human infection.

There is a need for the development of effective anti-influenza prophylactics and therapeutics. Furthermore, given the high degree of unpredictability in evolution of these influenza viruses, there is a particular need for the development of cross-strain effective (e.g., "universal" or "broad spectrum") anti-influenza prophylactics and therapeutics. Such effective anti-influenza agents, and particularly such universal or broad spectrum anti-influenza agents could replace or augment vaccines designed to target specific 'seasonal' viral strains in circulation (Ekiert et al., *Science*, 324(5924):246, 2009 and Sui et al., *Nat Struct Mol Biol.* 16(3):265, 2009). Alternatively or additionally, there is a need for the development of effective anit-influenza prophylactis or therapeutics that can replace or augment current anti-viral therapy. The importance of such agents is highlighted by the emerging drug resistance to current antivirals Tamiflu/Relenza (NA-inhibitors) and Amantadine/Rimantadine (MP-2 inhibitors) (Collins et al., Nature 453:1258, Stouffer et al., Nature, 451:596, 2008, Pielak et al., *Proc. Natl. Acad. Sci. USA,* 106:7379, 2009). For instance, over 98% and 100% of H1N1 strains in the 2011/2012 flu season are resistant to Tamiflu and the adamantane derivatives (Amantadine/Rimantadine), respectively.

SUMMARY

The present invention provides new influenza binding agents. Among other things, the present invention provides influenza binding agents that bind to multiple influenza strains. The present invention specifically provides binding agents that bind to influenza hemagglutinin (HA). The present invention particularly provides certain antibodies that bind to influenza HA. In some embodiments, such antibodies are characterized by binding to a particular HA epitope and/or to HA from a group 1 virus, a group 2 virus or, in some embodiments, both. In some embodiments, provided antibodies bind to an HA selected from the group consisting of an HA polypeptide of subtype H1, H2, H3, H4, H5, H6, H7, H8, H9, H10, H11, H12, H13, H14, H15, H16, and combinations thereof. In some embodiments, provided antibodies are characterized by an ability to neutralize infection by a group 1 virus, a group 2, virus, or in some embodiments, both. In some such embodiments, such provided antibodies show a neutralization $IC_{50}$ (ug/ml) within a range as described and/or exemplified herein. In some embodiments, such provided antibodies show a neutralization $IC_{50}$ (ug/ml) whose lower bound is about 0.1 ug/ml and upper bound is about 10 ug/ml. In some embodiments, such provided antibodies show a neutralization $IC_{50}$ (ug/ml) whose lower bound is selected from the group consisting of 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0 or more ug/ml, and whose upper bound is higher than the lower bound and is selected from the group consisting of 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0 or more ug/ml.

In some embodiments, such provided antibodies show binding to influenza HA (e.g., group 1 and/or group 2 subtypes) with a $K_D$ (nM) less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, or less than 50 nM.

In some embodiments, such provided antibodies show binding to influenza HA with a $K_a$ ($M^{-1}s^{-1}$) whose lower bound is about $0.01 \times 10^5$ $M^{-1}s^{-1}$ and upper bound is about $1.0 \times 10^6$ $M^{-1}s^{-1}$. such provided antibodies show binding to influenza HA with a $K_a$ ($M^{-1}s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0 \times 10^5$, $1.2 \times 10^5$, $1.4 \times 10^5$, $1.6 \times 10^5$, $1.8 \times 10^5$, $2.0 \times 10^5$, or more $M^{-1}s^{-1}$, and whose upper bound is higher than the lower bound and is slected from the group consisting of $1.0 \times 10^5$, $1.5 \times 10^5$, $2.0 \times 10^5$, $2.5 \times 10^5$, $3.0 \times 10^5$, $3.5 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or more $M^{-1}s^{-1}$.

In some embodiments, such provided antibodies show binding to influenza HA with a $K_d$ ($s^{-1}$) whose lower bound is about $0.01 \times 10^5$ $s^{-1}$ and upper bound is about $1.0 \times 10^6$ $s^{-1}$. such provided antibodies show binding to influenza HA with a $K_a$ ($s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0\times10^5$, $1.2\times10^5$, $1.4\times10^5$, $1.6\times10^5$, $1.8\times10^5$, $2.0\times10^5$, or more $s^{-1}$, and whose upper bound is higher than the lower bound and is selected from the group consisting of $1.0\times10^5$, $1.5\times10^5$, $2.0\times10^5$, $2.5\times10^5$, $3.0\times10^5$, $3.5\times10^5$, $4.5\times10^5$, $5.0\times10^5$, $5.5\times10^5$, $6.0\times10^5$, $6.5\times10^5$, $7.0\times10^5$, $7.5\times10^5$, $8.0\times10^5$, $8.5\times10^5$, $9.0\times10^5$, $9.5\times10^5$, $1.0\times10^6$ $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, or more $s^{-1}$.

The present invention also defines structural features of certain provided antibodies that confer particular functional attributes (e.g., HA binding, neutralization, subtype specificity, etc). The present invention therefore provides binding agents that share such structural features, and in some embodiments therefore also functional attributes, of these provided antibodies. For example, in some embodiments, the present invention provides binding agents that share structural features, and functional attributes, of one or more of the certain provided antibodies having amino acid sequences as set forth in Tables 2 and/or 3 herein.

In some embodiments, such structural features of such certain provided antibodies include one or more CDRs or one or more FRs at least 80% identical in sequence to a corresponding CDR or FR from Tables 2 and 3 (SEQ ID NO: 1-60). In some embodiments, such structural features of such certain provided antibodies include one or more CDRs and/or one or more FRs that is identical in sequence to a corresponding CDR or FR from Tables 2 and 3 (SEQ ID NO: 1-60). In some embodiments, such structural features of such certain provided antibodies include CDRs and FRs that are identical in sequence to those set forth in Tables 2 and 3 (SEQ ID NO: 1-60).

In some embodiments, such structural features include CDR and FR sequence elements, each of which is identical to a reference CDR or FR sequence element set forth in Table 2 and/or Table 3 (SEQ ID NOs:1-60) except that it includes one or more amino acid substitutions with respect to that reference sequence element, where the included CDR and FR sequence elements together contain no more than 18, 17, 16, 15, 14, 13, 12, 11, 10, 9, 8, 7, 6, 5, 4, 3, 2, or 1 substitutions in CDR and FR sequences, as compared with the corresponding CDR and FR reference sequence elements from Tables 2 and 3 (SEQ ID NO: 1-60). In some embodiments, such structural features include CDR and FR sequence elements together contain no more than 18 substitutions as compared with the corresponding CDR and FR reference sequence elements from Tables 2 and 3 (SEQ ID NO: 1-60). In some embodiments, such structural features include CDR and FR sequence elements together contain no more than 15 substitutions as compared with the corresponding CDR and FR reference sequence elements from Tables 2 and 3 (SEQ ID NO: 1-60).

In some embodiments, such structural features includes a FR sequence element, which is identical to a reference FR sequence element set forth in Table 2 and/or Table 3 (SEQ ID NOs:1-60) except that it includes one or more amino acid substitutions with respect to that reference sequence element, where the included FR sequence element contains no more than 18, 17, 16, 15, 14, 13, 12, 11, 10, 9, 8, 7, 6, 5, 4, 3, 2, or 1 substitutions in FR sequence, as compared with the corresponding FR reference sequence elements from Tables 2 and 3 (SEQ ID NO: 1-60).

In some embodiments, such structural features includes a CDR sequence element, which is identical to a reference CDR sequence element set forth in Table 2 and/or Table 3 (SEQ ID NOs:1-60) except that it includes one or more amino acid substitutions with respect to that reference sequence element, where the included CDR sequence element contains no more than 18, 17, 16, 15, 14, 13, 12, 11, 10, 9, 8, 7, 6, 5, 4, 3, 2, or 1 substitutions in CDR sequence, as compared with the corresponding CDR reference sequence elements from Tables 2 and 3 (SEQ ID NO: 1-60).

In some embodiments, such structural features includes a VH sequence element, which is identical to a reference VH sequence element set forth in Table 2 and/or Table 3 (SEQ ID NOs:1-60) except that it includes one or more amino acid substitutions with respect to that reference sequence element, where the included VH sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof, as compared with the corresponding VH reference sequence elements from Tables 2 and 3 (SEQ ID NO: 1-60).

In some embodiments, such structural features includes a VL sequence element, which is identical to a reference VL sequence element set forth in Table 2 and/or Table 3 (SEQ ID NOs:1-60) except that it includes one or more amino acid substitutions with respect to that reference sequence element, where the included VL sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VL-1, VL-2, VL-3, VL-4, VL-5, VL-6, VL-7, VL-8, VL-9, VL-10, VL-11, or fragment thereof, as compared with the corresponding VL reference sequence elements from Tables 2 and 3 (SEQ ID NO: 1-60).

In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof combined with any one of VL-1, VL-2, VL-3, VL-4, VL-5, VL-6, VL-7, VL-8, VL-9, VL-10, VL-11, or fragment thereof. In some embodiments, VH-1 (SEQ ID NO:1) is combined with VL-1 (SEQ ID NO:33).

In some embodiments, such structural features include a complementarity determining region (CDR) 1 sequence element that shows at least 65%, more than 70%, more than 75%, more than 80%, more than 85%, more than 90%, more than 95%, or more than 99% identity with a reference CDR1 sequence element from Tables 2 and/or 3 (SEQ ID NOs:17-18 and/or SEQ ID NOs:44-54). In some embodiments, such structural features include a complementarity determining region (CDR) 1 sequence element that has two or more amino acid substitutions as compared to a reference CDR1 sequence element from Tables 2 and 3 (SEQ ID NOs:17-18 and/or SEQ ID NOs:44-54). In some embodiments, such structural features include a complementarity determining region (CDR) 1 sequence element that has one or more amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has at least two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has fewer than two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has an amino acid sequence that is identical to that of one of the reference CDR1 sequence elements from Tables 2 and 3 (SEQ ID NOs:17-18 and/or SEQ ID NOs:44-54).

In some embodiments, such structural features include a complementarity determining region (CDR) 2 sequence element that shows at least 65%, more than 70%, more than 75%, more than 80%, more than 85%, more than 90%, more than 95%, or more than 99% identity with a reference CDR2 sequence element from Tables 2 and/or 3 (SEQ ID NOs:17-18 and/or SEQ ID NOs:44-54). In some embodiments, such structural features include a complementarity determining region (CDR) 2 sequence element that has two or more amino acid substitutions as compared to a reference CDR2 sequence element from Tables 2 and 3 (SEQ ID NOs:17-18 and/or SEQ ID NOs:44-54). In some embodiments, such structural features include a complementarity determining region (CDR) 2 sequence element that has one or more amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has at least two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has fewer than two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has an amino acid sequence that is identical to that of one of the reference CDR2 sequence elements from Tables 2 and 3 (SEQ ID NOs:17-18 and/or SEQ ID NOs:44-54).

In some embodiments, such structural features include a complementarity determining region (CDR) 3 sequence element that shows at least 65%, more than 70%, more than 75%, more than 80%, more than 85%, more than 90%, more than 95%, or more than 99% identity with a reference CDR3 sequence element from Tables 2 and/or 3 (SEQ ID NOs:17-18 and/or SEQ ID NOs:44-54). In some embodiments, such structural features include a complementarity determining region (CDR) 3 sequence element that has two or more amino acid substitutions as compared to a reference CDR3 sequence element from Tables 2 and 3 (SEQ ID NOs:17-18 and/or SEQ ID NOs:44-54). In some embodiments, such structural features include a complementarity determining region (CDR) 3 sequence element that has one or more amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has at least two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has fewer than two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has an amino acid sequence that is identical to that of one of the reference CDR3 sequence elements from Tables 2 and 3 (SEQ ID NOs:17-18 and/or SEQ ID NOs:44-54).

In some embodiments, such structural features include a VH framework region sequence element that shows more than 65%, more than 70%, more than 75%, more than 80%, more than 85%, more than 90%, more than 95%, or more than 99% percent identity with a reference VH framework region sequence element from Table 2 (SEQ ID NOs:1-16).

In some embodiments, such structural features include a VL framework region sequence element that shows more than 65%, more than 70%, more than 75%, more than 80%, more than 85%, more than 90%, more than 95%, or more than 99% percent identity with a reference VL framework region sequence element from Table 3 (SEQ ID NOs:33-43).

In some embodiments, the present invention provides a binding agent that includes such structural features of such certain provided antibodies such that the provided binding agent shares with the certain provided antibodies the functional attribute that it binds to influenza HA selected from the group consisting of group 1 subtype, group 2 subtype, and combinations thereof.

In some embodiments, a provided binding agent shows an influenza neutralization $IC_{50}$ (ug/ml) within a range as set forth herein for a particular provided antibody. In some embodiments, a provided binding agent shows such an $IC_{50}$ (ug/ml) for an influenza virus of group 1 subtype, group 2 subtype, or both. In some embodiments, a provided binding agent is characterized by a functional attribute of an influenza neutralization $IC_{50}$ (ug/ml) within a range as described and/or exemplified herein. In some embodiments, such provided binding agent shows a neutralization $IC_{50}$ (ug/ml) whose lower bound is about 0.1 ug/ml and upper bound is about 10 ug/ml. In some embodiments, such provided binding agent shows a neutralization $IC_{50}$ (ug/ml) whose lower bound is selected from the group consisting of 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0 or more ug/ml, and whose upper bound is higher than the lower bound and is selected from the group consisting of 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0 or more ug/ml.

In some embodiments, such provided binding agent shows binding to influenza HA (e.g., group 1 and/or group 2 subtypes) with a $K_D$ (nM) less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, or less than 50 nM.

In some embodiments, such provided binding agent shows binding to influenza HA with a $K_a$ ($M^{-1}s^{-1}$) whose lower bound is about $0.01\times10^5$ $M^{-1}s^{-1}$ and upper bound is about $1.0\times10^6$ $M^{-1}s^{-1}$. such provided antibodies show binding to influenza HA with a $K_a$ ($M^{-1}s^{-1}$) whose lower bound is selected from the group consisting of $0.01\times10^5$, $0.02\times10^5$, $0.04\times10^5$, $0.04\times10^5$, $0.08\times10^5$, $0.1\times10^5$, $0.2\times10^5$, $0.4\times10^5$, $0.6\times10^5$, $0.8\times10^5$, $1.0\times10^5$, $1.2\times10^5$, $1.4\times10^5$, $1.6\times10^5$, $1.8\times10^5$, $2.0\times10^5$, or more $M^{-1}s^{-1}$, and whose upper bound is higher than the lower bound and is slected from the group consisting of $1.0\times10^5$, $1.5\times10^5$, $2.0\times10^5$, $2.5\times10^5$, $3.0\times10^5$, $3.5\times10^5$, $4.5\times10^5$, $5.0\times10^5$, $5.5\times10^5$, $6.0\times10^5$, $6.5\times10^5$, $7.0\times10^5$, $7.5\times10^5$, $8.0\times10^5$, $8.5\times10^5$, $9.0\times10^5$, $9.5\times10^5$, $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, or more $M^{-1}s^{-1}$.

In some embodiments, such provided binding agent shows binding to influenza HA with a $K_d$ ($s^{-1}$) whose lower bound is about $0.01 \times 10^5$ $s^{-1}$ and upper bound is about $1.0 \times 10^6$ $s^{-1}$. such provided antibodies show binding to influenza HA with a $K_a$ ($s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0 \times 10^5$, $1.2 \times 10^5$, $1.4 \times 10^5$, $1.6 \times 10^5$, $1.8 \times 10^5$, $2.0 \times 10^5$, or more $s^{-1}$, and whose upper bound is higher than the lower bound and is slected from the group consisting of $1.0 \times 10^5$, $1.5 \times 10^5$, $2.0 \times 10^5$, $2.5 \times 10^5$, $3.0 \times 10^5$, $3.5 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$ $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or more $s^{-1}$.

In some embodiments, the present invention provides a binding agent that includes such structural features of such certain provided antibodies such that the provided binding agent shares with the certain provided antibodies the functional attribute that it competes with one or more of the antibodies listed in Tables 2 and 3 (SEQ ID NO: 1-60) for binding to at least one HA polypeptide. In some embodiments, a provided binding agent such structural features that it competes with one or more of the antibodies listed in Tables 2 and 3 (SEQ ID NO: 1-60) for binding to a plurality of different HAs, which plurality of different HA polypeptides includes HA polypeptides proteins found in at least 2 different HA subtypes genotypes.

In some embodiments, a provided binding agent is characterized by a functional attribute of binding to one or more of HA polypeptides of subtype H1, H2, H3, H4, H5, H6, H7, H8, H9, H10, H11, H12, H13, H14, H15, and/or H16. In some embodiments, a provided binding agent binds to at least two HA polypeptides of subtype H1, H3, H5, H7, and H9.

In some embodiments, a provided binding agent in characterized by a functional attribute of binding to one or more epitopes in the MPER region of an HA polypeptide. In some embodiments, a provided binding agent is characterized by a functional attribute of binding to one or more epitopes in the MPER region of an HA polypeptide independent of its glycosylation. In some embodiments, a provided binding agent is characterized by a functional attribute of binding to one or more epitopes in the HA-1 (head) and/or HA-2 (stalk) domains of an HA polypeptide. In some embodiments, a provided binding agent is characterized by a functional attribute of binding to one or more epitopes located within the HA-1/HA-2 interface membrane proximal epitope region (MPER). In some embodiments, a provided binding agent is characterized by a functional attribute of binding to one or more epitopes located within the canonical α-helix and/or residues in its vicinity.

In some embodiments, a provided binding agent is or comprises a polypeptide. In some embodiments, a provided binding agent is or comprises an antibody or fragment thereof. In some embodiments, a provided binding agent is or comprises a monocolonal antibody or fragment thereof. In some embodiments, the binding agent is or comprises a "full length" antibody, in that it contains two heavy chains and two light chains, optionally associated by disulfide bonds as occurs with naturally-produced antibodies. In some embodiments, the binding agent is or comprises a fragment of a full-length antibody in that is contains some, but not all of the sequences found in a full-length antibody. For example, in some embodiments, the binding agent is or comprises antibody fragments which include, but are not limited to, Fab, Fab', F(ab')2, scFv, Fv, dsFv diabody, and Fd fragments. In some embodiments, a provided binding agent is or comprises an antibody that is a member of an antibody class selected from the group consisting of IgG, IgM, IgA, IgD, IgE or fragment thereof. In some embodiments, a provided binding agent is or comprises an antibody produced by chemical synthesis. In some embodiments, a provided binding agent is or comprises an antibody produced by a cell. In some embodiments, a provided binding agent is or comprises a chimeric antibody, for example from mouse, rat, horse, pig, or other species, bearing human constant and/or variable region domains.

In some embodiments, a provided binding agent is or comprises a polypeptide with antibody CDRs. In some embodiments, a provided binding agent is or comprises a scaffolding domain, such as protein A, lipoclins, ankryin consensus repeat domain, thioredoxin, adnectin, anticalins, centyrin, avimer domains, ubiquitin, zinc finger DNA-binding proteins (ZEPs), or IgNARs, which is used to displays one or more CDRs. In some embodiments, a provided binding agent is or comprises a cystine-knot miniprotein. In some embodiments, a provided binding agent is or comprises an avibody (diabody, tribody, tetrabody). In some embodiments, a provided binding agent is or comprises a Scopion, wherein the Scorpion structure comprises two binding moieties separated by an immunoglobulin Fc domain. In some embodiments, a provided binding agent is or comprises a VHH (i.e., an antigen-specific VHH) antibody that comprises only a heavy chain. In some embodiments the VHH is derived from a llama or other camelid antibody (e.g., a camelid IgG2 or IgG3, or a CDR-displaying frame from such camelid Ig). In some embodiments such a VHH is derived from a shark.

In some embodiments, a provided binding agent is or comprises one or more "mini-antibodies" or "minibodies", which are sFv polypeptie chains that include oligomerization domains at their C-termini, separated from the sFv by a hinge region. In some embodiments, the hinge region comprises a self-associating alpha-helix or leucine zipper, which may or may not be further stabilized by additional disulfide bonds. In some embodiments, a provided binding agent is or comprises a peptidomimetic. In some embodiments, a provided binding agent is or comprises a mimeotope.

In some embodiments, a provided binding agent is or comprises a conjugate, in which a binding agent moiety (comprises or consists of the binding agent or a functional portion thereof) with a conjugated moiety. In some embodiments such a conjugated moiety is an entity. In some embodiments, such an entity is a chemical class selected from the group consisting of polypeptides, carbohydrates, lipids, small organic molecule, organic polymer, inorganic polymer, metals, ions, isotopes or combinations thereof. In some embodiments such a conjugated moiety is or comprises a therapeutic or diagnostic payload. In some embodiments, such a conjugated moiety is or comprises a detectable payload. In some embodiments, such a conjugated moiety is or comprises a detectable entity. In some embodiments, such a conjugated moiety is or comprises an affinity agent. In some embodiments, such a conjugated moiety is or comprises a targeting agent. In some embodiments, such a conjugated moiety is or comprises a masking and/or stabilizing agent. In some embodiments, a provided conjugate comprises a single binding agent moiety and a plurality of conjugated moieties; in some embodiments such plurality of conjugated moieties comprises a plurality of the same conjugated moiety; in some embodiments such plurality of conjugated moieties includes two or more different conjugated moieties, optionally of different types (e.g., therapeutic payloads, detectable payload, targeting agent, affinity agent etc.).

In some embodiments, a provided binding agent is or comprises a nucleic acid, such as DNA or RNA. In some embodiments the nucleic acid is designed to mimic an epitope within a hemagglutinin (HA) polypeptide. In some embodiments the nucleic acid is designed to mimic a conserved epitope within one or more Influenza HA polypeptide subtypes. In some embodiments, a provided binding agent is or comprises one or more oligonucleotides. In some embodiments, a provided binding agent is or comprises one or more oligonucleotides comprising a secondary structure such as loop, hairpin, fold or combinations thereof. In some embodiments, a provided binding agent is or comprises one or more oligonucleotides comprising a higher ordered (tertiary or quaternary) structure. In some embodiments, a provided binding agent is or comprises an aptamer.

In some embodiments, the present invention provides a cell or cell line expressing a binding agent as described herein. In some embodiments, such a cell or cell line is a mammalian cell or cell line. In certain embodiments, such a cell or cell line is a hybridoma.

In some embodiments, the present invention provides a method of treating a patient, the method comprising steps of administering to a patient suffering from or susceptible to influenza infection a composition comprising a binding agent described herein, in an appropriate unit dosage form for delivery according to a regimen that correlates with reduction in incidence and/or severity, and/or with delay of onset of one or more manifestations or effects of influenza infection.

In some embodiments, the present invention provides a kit comprising at least one binding agent as described herein, formulated for administration via an administration device, together with such an administration device in a set comprising one or more containers. In some embodiments, an appropriate administration device is selected from the group consisting of a syringe, needle, applicator, and combinations thereof. In some embodiments, a provided kit includes instructions for use.

Provided binding agents, compositions, and methods are useful, for example, in research and/or in medicine. In some embodiments, provided binding agents, compositions, and methods are useful, for example, in prophylaxis, treatment, diagnosis, and/or study of influenza. For example, in some embodiments, provided binding agents or compositions are administered to subjects suffering from or susceptible to an influenza infection. In some embodiments, provided binding agents or compositions are admininstered prior to known exposure to influenza, or to particular influenza subtypes or strains. In some embodiments, provided binding agents are administered after known exposure to influenza, or to particular influenza subtypes or strains. In some embodiments, provided binding agents or compositions are administered prior to manifestation of effects or symptoms of influenza infection, or to one or more particular effects or symptoms of influenza infection, including of influenza infection with one or more particular influenza subtypes or strains. In some embodiments, provided bdbinding agents or compositions are administered prior to manifestation of effects or symptoms of influenza infection, or to one or more particular effects or symptoms of influenza infection, including influenza infection with one or more particular influenza subtypes or strains.

In some embodiments, provided binding agents or compositions are administered to a subject in combination with one or more other anti-influenza therapies and/or with one or more other therapies for an effect on symptom of influenza infection (e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat).

BRIEF DESCRIPTION OF THE DRAWING

The Figures described below, that together make up the Drawing, are for illustration purposes only, not for limitation.

FIG. 1A (top panel) demonstrates that the particular depicted antibody binds to both group 1 and group 2 subtypes of HA with differential binding affinity; and FIG. 1A (bottom panel) and FIG. 1B show that the antibody binds specifically to HA.

Figure 3C:
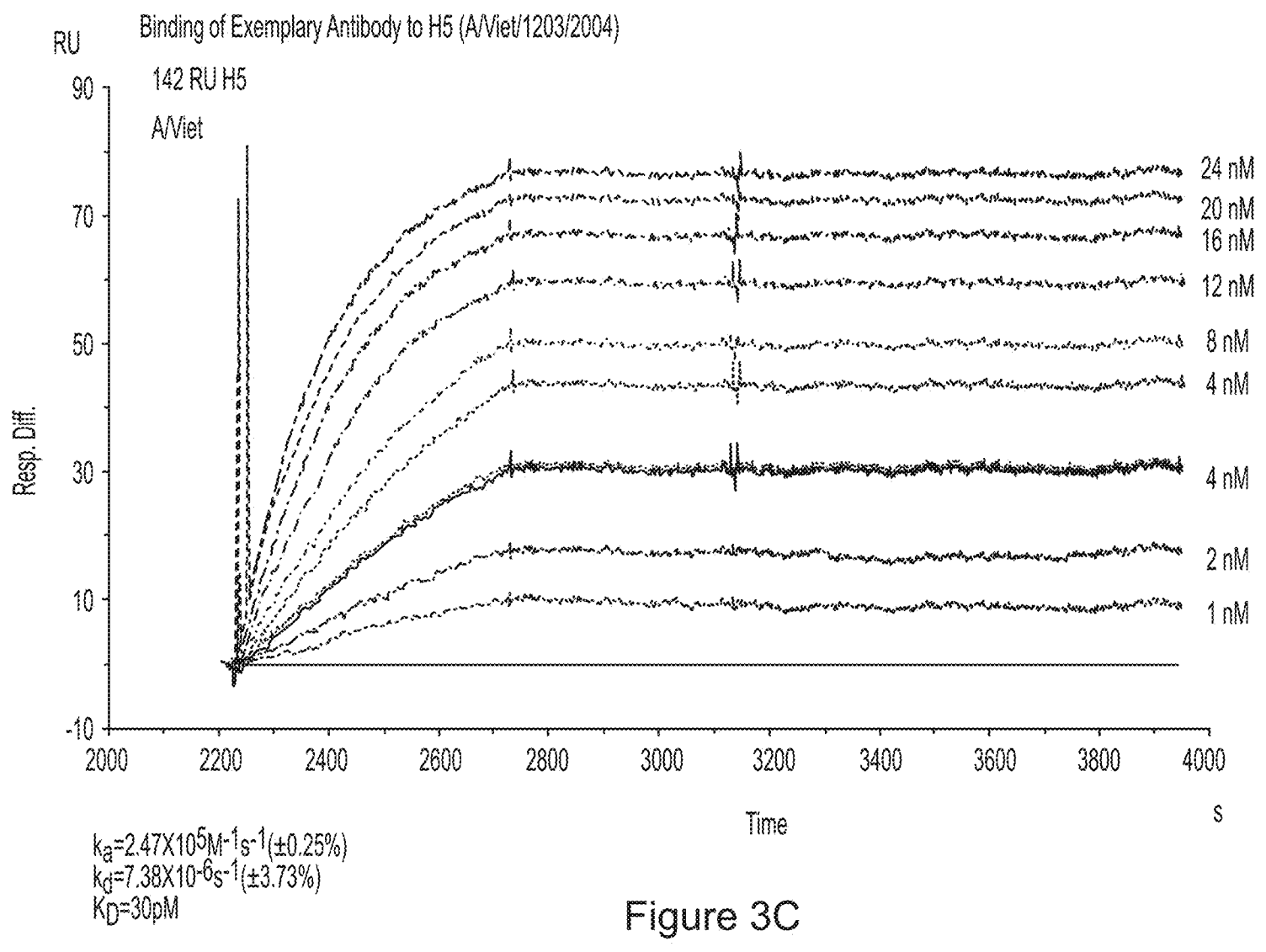

FIGS. 3A-E depicts HA binding affinity and kinetics for an exemplary antibody over a range of concentrations. The particular antibody binds to both group 1 and group 2 subtypes of HA with differential binding affinity and kinetics.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by influenza. In some embodiments, an animal may be a transgenic animal, genetically engineered animal, and/or a clone.

Figure 1:
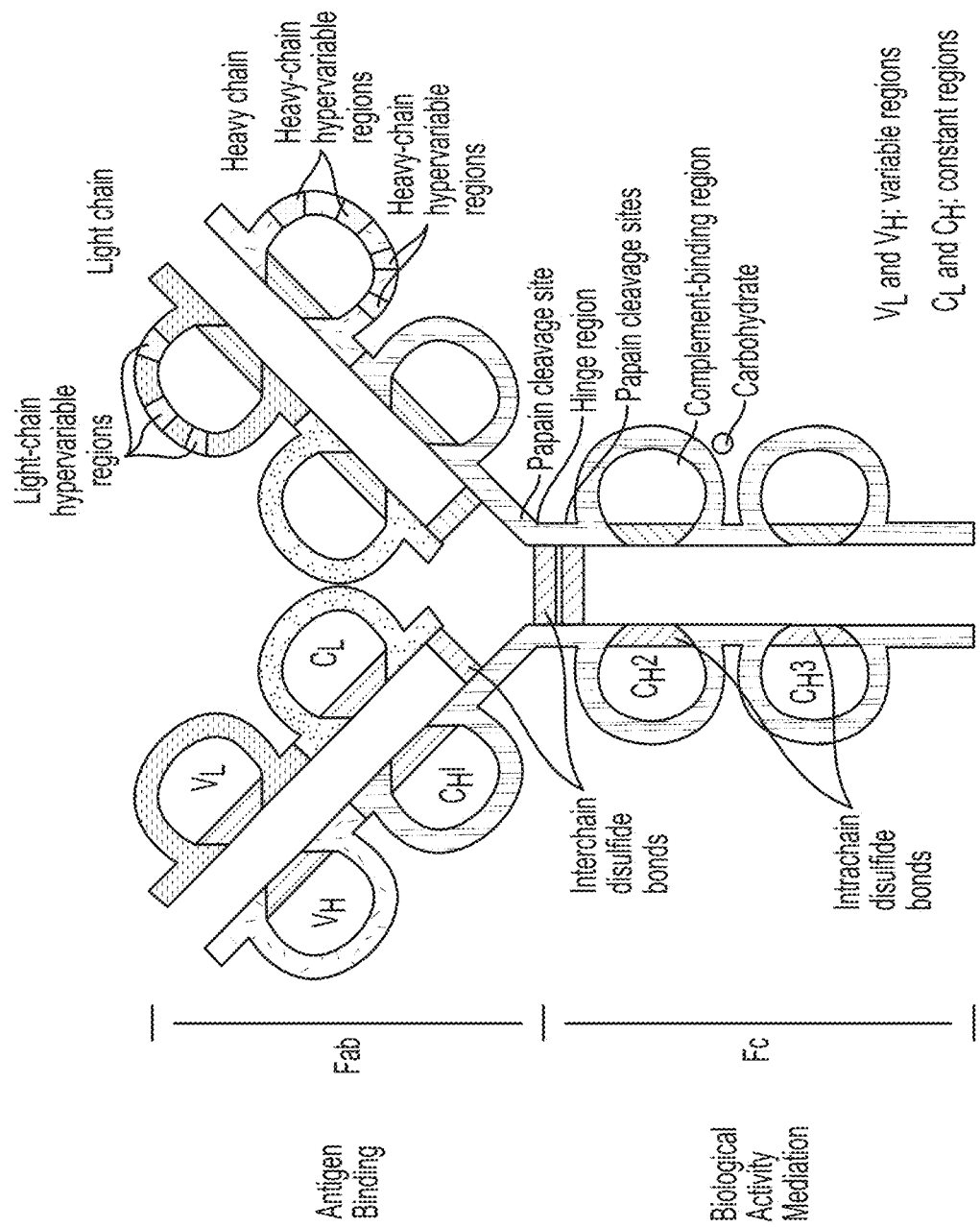
FIG. 1 depicts a structural representation of the various parts, regions and domains of a mammalian antibody.

Antibody: As used herein, the term "antibody" refers to a polypeptide having structural characteristics of an immunoglobulin, as those are understood in the art. As produced by mammalian cells in nature, an immunoglobulin has the structure depicted in FIG. 1. A typical immunoglobulin (antibody) structural unit is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is futher subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In many embodiments, an antibody is a polypeptide whose amino acid sequence includes one or more structural elements recognized by those skilled in the art are as a complementarity determining region (CDR). In some embodiments, an antibody is a polypeptide whose amino acid sequence includes structural elements recognized by those skilled in the art as an immunoglobulin variable domain. In some embodiments, an antibody is "full length" in that in contains two heavy chains and two light chains, optionally associated by disulfide bonds as occurs with naturally-produced antibodies. In some embodiments, an antibody is a fragment of a full-length antibody in that it contains some, but not all of the sequences found in a full-length antibody. For example, in some embodiments, Examples of antibody fragments include, but are not limited to, Fab, Fab', F(ab')2, scFv, Fv, dsFv diabody, and Fd fragments. In some embodiments, an antibody is a member an antibody class selected from the group consisting of IgG, IgM, IgA, IgD, and IgE. In some embodiments, an antibody is produced by chemical synthesis. In some embodiments, an antibody is a monoclonal antibody. In some embodiments, an antibody is a polyclonal antibody. In some embodiments, an antibody is produced by a cell. In some embodiments, an antibody is produced by chemical synthesis. In some embodiments, an antibody is derived from a mammal. In some embodiments, an antibody is derived from an animal such as, but not limited to, mouse, rat, horse, pig, or goat. In some embodiments, an antibody is produced using a recombinant cell culture system. In some embodiments an antibody is a chimeric antibody, for example, from mouse, rat, horse, pig, or other species, bearing human constant and/or variable regions domains. In some embodiments, an antibody is a derived from a human. In some embodiments, an antibody is a polyclonal antibody. In some embodiments, an antibody is a humanized antibody.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding agent: As used herein, the term "binding agent" refers to an agent that is capable of binding to an antigen or biological target. In some embodiments, a binding agent comprises a protein. In some embodiments, a binding agent is or comprises a naturally occurring protein. In some embodiments, a binding agent is derived from a cell or a virus. In some embodiments, a binding agent is a synthetic or chemically synthesized protein. In some embodiments, binding agents are comprised of natural amino acids. In other embodiments, a binding agent comprises one or more unnatural amino acids. In some embodiments, a binding agents is comprised of a combination of natural and unnatural amino acids. In some embodiments, a binding agent is comprised of one, two or more polypeptide chains that are covalently or non-covalently associated. In some embodiments, a binding agent may be linked to, or part of, a longer polypeptide chain, so long as the binding agent retains its three-dimensional structure and arrangement for interaction. In some embodiments, a binding agent may be appended to the N- or C-termini of another polypeptide sequence that is or is not a binding agent. In some embodiments, a binding agent may be incorporated into the sequence of another polypeptide that is or is not a binding agent, thereby separating the polypeptide sequence into two or more segments.

In some embodiments, a binding agent is a protein that functions similarly to an antibody and is able to bind to a specific antigent to form a complex and elicit a biological response (e.g., agonize or antagonize a particular biological activity.) In some embodiments, the binding agent is an antibody. In some embodiments, the binding agent is or comprises a "full length" antibody, in that it contains two heavy chains and two light chains, optionally associated by disulfide bonds as occurs with naturally-produced antibodies. In some embodiments, the binding agent is or comprises a fragment of a full-length antibody in that is contains some, but not all of the sequences found in a full-length antibody. For example, in some embodiments, the binding agent is or comprises antibody fragments which include, but are not limited to, Fab, Fab', F(ab')2, scFv, Fv, dsFv diabody, and Fd fragments. In some embodiments, a provided binding agent is or comprises a VHH (i.e., an antigen-specific VHH) antibody that comprises only a heavy chain. In some embodiments the VHH is derived from a llama or other camelid antibody (e.g., a camelid IgG2 or IgG3, or a CDR-displaying frame from such camelid Ig). In some embodiments a VHH is derived from a shark. In some embodiments, a provided binding agent is or comprises one or more "mini-antibodies" or "minibodies", which are sFv polypeptie chains that include oligomerization domains at their C-termini, separated from the sFv by a hinge region. In some embodiments, the hinge region comprises a self-associating alpha-helix or leucine zipper, which may or may not be further stabilized by additional disulfide bonds.

In some embodiments, a binding agent is a scaffold protein such as, but is not limited to, protein A, lipoclins, ankryin consensus repeat domain, thioredoxin, adnectin, anticalins, centyrin, avimer domains, ubiquitin, zinc finger DNA-binding proteins (ZEPs), or IgNARs. In some embodiments, a binding agent is a scaffold protein, in which the scaffold protein is engineered to display one or more CDRs. In some embodiments, a provided binding agent is or comprises a cystine-knot miniprotein. In some embodiments, a provided binding agent is or comprises an avibody (diabody, tribody, tetrabody). In some embodiments, a provided binding agent is or comprises a Scorpion, wherein the Scorpion structure comprises two binding moieties separated by an immunoglobulin Fc domain. In some embodiments, a provided binding agent is or comprises a peptidomimetic. In some embodiments, a provided binding agent is or comprises a stapled peptide.

In some embodiments a binding agent comprises an agent that is capable of binding to a selected binding site. In some embodiments, a binding agents is capable of binding to a selected binding site in a hemagglutinin (HA) polypeptide. In some specific embodiments, the binding agents is capable of binding to a selected binding site in the membrane proximal epitope region (MPER) of a HA polypeptide. In some specific embodiments, the binding agents is capable of binding to a selected binding site in the HA-1 (head) and/or HA-2 (stalk) domains of an HA polypeptide. In some specific embodiments, the binding agents is capable of binding to a selected binding site in the HA-1/HA-2 interface membrane proximal epitope region (MPER).

In some embodiments, a binding agent is an agent that is able to associate with a binding target by interaction with one or more target residues. In some embodiments, such target residues are amino acids, saccharides, or combinations thereof. In some specific embodiments a binding agent is able to bind to a modified HA polypeptide such as, but not limited to, N-linked glycans, sialylated glycans and/or combinations thereof.

In some embodiments, a binding agent is an agent that is able to compete with an influenza virus for binding to an HA polypeptide, such that binding between the influenza virus and the HA polypeptide is reduced by at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold. In some embodiments, a binding agent is an agent that is able to compete with an influenza virus for binding to glycans on HA receptors such that binding between the influenza virus and the glycans on the HA receptor is reduced by at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold.

In some embodiments, a binding agent is or comprises a nucleic acid, such as DNA or RNA. In some embodiments, a binding agent comprises one or more oligonuclotides. In some embodiments, a binding agent is or comprises one or more oligonuclotides comprising a secondary structure such as loop, hairpin, fold or combinations thereof. In some embodiments, a binding agent is or comprises one or more oligonuclotides comprising a higher ordered (tertiary or quaternary) structure. In some embodiments a binding agent is a nucleic acid the forms a structure designed to mimic an epitope found within a hemagglutinin (HA) polypeptide. In some embodiments a binding agent is a nucleic acid the forms a structure designed to mimic a conserved epitope found within one or more Influenza HA polypeptide subtypes. In some embodiments, a binding agent is or comprises an aptamer.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Broad spectrum: As used herein, the phrase "broad spectrum" refers to agents that bind a variety of HA polypeptides from different influenza virus strains. In some embodiments, broad spectrum agents bind to a plurality of different HA polypeptides. Exemplary such HA polypeptides include, H1, H2, H3, H4, H5, H6, H7, H8, H9, H10, H11, H12, H13, H14, H15, and/or H16 polypeptides, or combinations thereof. In some embodiments, provided agents are broad spectrum in that they bind to HA polypeptides from at least two different clades or clusters of virus. In some embodiments provided agents are broad spectrum in that they bind to HA polypeptides from all known clades of virus. In some embodiments, provided agents are broad spectrum in that they bind to HA polypeptides from group 1 and group 2 influenza viruses. In some embodiments, broad spectrum refers to agents that bind to some or all types of HA polypeptides that mediate infection of particular hosts, e.g., avian, camel, canine, cat, civet, equine, human, leopard, mink, mouse, seal, stone martin, swine, tiger, whale, etc.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Combination Therapy: The term "combination therapy", as used herein, refers to those situations in which two or more different agents are administered in overlapping regimens so that the subject is simultaneously exposed to both agents.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regiment, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (www.ncbi.nlm.nih.gov/genomes/FLU/FLU.html) that, as of the filing of the present application included 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HA polypeptides that mediate infection of particular hosts, e.g., avian, camel, canine, cat, civet, environment, equine, human, leopard, mink, mouse, seal, stone martin, swine, tiger, whale, etc.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Mimotope: As used herein, the term "mimotope" refers to a macromolecule which mimics the structure of an epitope. In some embodiments, a mimotope elicits an antibody response identical or similar to that elicited by its corresponding epitope. In some embodiments, an antibody that recognizes an epitope also recognizes a mimotope which mimics that epitope. In some embodiments, a mimotope is a peptide. In some embodiments, a mimotope is a small molecule, carbohydrate, lipid, or nucleic acid. In some embodiments, mimotopes are peptide or non-peptide mimotopes of conserved influenza epitopes. In some embodiments, by mimicking the structure of a defined viral epitope, a mimotope interferes with the ability of influenza virus particles to bind to its natural binding partners, e.g., by binding to the natural binding partner itself.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Reference Structural Element: As used herein, the term "reference structural element" is an element of chemical structure against which another element is compared. In some embodiments, a reference structural element is or comprises an arrangement of atoms or moieties with respect to one another and/or in three dimensional space. In some such embodiments, the relevant atoms or moieties are defined by chemical identity (e.g., a particular amino acid or chemical group or structure, etc) and/or by function (e.g., hydrogen-bond donor or acceptor, free radical, etc). In some particular embodiments, where a reference structural element is found in a reference polymer, the reference structural element may be or comprise a sequence of monomers present in the reference polymer. For example, in some such embodiments, a reference structural element may be or comprise a particular amino acid sequence element in a polypeptide, a particular nucleotide sequence element in a polynucleotide, and or a particular glycan structure in a polysaccharide.

Small Molecule: In general, a "small molecule" is a molecule that is less than about 5 kilodaltons (kD) in size. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids., and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., influenza) has been diagnosed with and/or exhibits one or more symptoms of the disease, disorder, or condition.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to influenza).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that has a therapeutic effect and/or elicits a desired biological and/or pharmacological effect, when administered to a subject.

Therapeutically effective amount: As used herein, the term "therapeutically effective amount" refers to an amount of a therapeutic agent (e.g., protein, and specifically e.g., antibody) which is statistically correlated with a particular therapeutic effect when administered to a population of subjects, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to reduce the incidence and/or severity of and/or to delay onset of one or more features, symptoms, or characteristics of a disease, disorder, or condition. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Universal anti-influenza agent: As used herein, the term "universal anti-influenza agent" refers to an agent that has broad-spectrum neutralization across influenza virus strains, groups, clades, and clusters.

Unnatural amino acid: As used herein, the term "unnatural amino acid" refers to any amino acid, modified amino acid, and/or amino acid analogue that is not one of the 20 naturally occurring amino acids. Refer to U.S. Pat. Nos. 7,045,337, 7,385,028, and 7,332,571, the entire disclosures of which are incorporated herein by reference. As used herein, "unnatural amino acid" also encompasses chemically modified amino acids, including but not limited to salts, amino acid derivatives (such as amides), and/or substitutions. Amino acids, including carboxy- and/or amino-terminal amino acids in peptides, can be modified by PEGyation, methylation, amidation, acetylation, and/or substitution with other chemical groups that do not adversely affect the activity of the binding agent. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION

As described herein, the present invention provides new influenza binding agents that bind to multiple influenza strains. The present invention particulary provides certain antibodies that bind to influenza HA, along with binding agents that share particular structural and/or functaional characteristis of the provided antibodies.

Influenza Antigens

Hemagglutinin (HA) Polypeptides

Influenza viruses are RNA viruses which are characterized by a lipid membrane envelope containing two glycoproteins, a hemagglutinin (HA) polypeptide and a neuraminidase (NA) polypeptide, embedded in the membrane of the virus particular. There are 16 known HA polypeptide subtypes (H1, H2, H3, H4, H5, H6, H7, H8, H9, H10, H11, H12, H13, H14, H15, and H16) and 9 NA polypeptide subtypes (N1, N2, N3, N4, N5, N6, N7, N8, and N9), and different influenza strains are named based on the number of the strain's HA polypeptide and NA polypeptide subtypes, wherein there are different combinations of one HA polypeptide subtype combined with one NA polypeptide subtype (for example, H1N1, H1N2, H1N3, H1N4, H1N5, etc.).

Based on comparisons of amino acid sequence identity and of crystal structures, the HA polypeptide subtypes have been divided into two main groups and four smaller clades, which is further divided into five clusters. The different HA polypeptide subtypes do not necessarily share strong amino acid sequence identity, but the overall 3D structures of the different HA polypeptide subtypes are similar to one another, with several subtle differences that can be used for classification purposes. For example, the particular orientation of the membrane-distal subdomains in relation to a central α-helix is one structural characteristic commonly used to determine HA polypeptide subtype (Russell et al., *Virology*, 325:287, 2004).

HA, as it occurs in nature, is a trimer of three identical monomers, each synthesizes as a precursor that is proteolytically processed into two di-sulfide bonded polypeptide chains. Mature HA polypeptides are comprised of two domains, (1) a core HA-1 domain known as the sialic acid-binding domain, and (2) the transmembrane stalk of HA, known as HA-2 domain. HA-1 contains the binding site for glycans and it is thought that HA-1 is responsible for mediating binding of HA to the HA-receptor. HA-2 is responsible for presenting the HA-1 domain. Typically, polar and non-polar interactions between the three long HA alpha-helices of the stem of HA monomers provide the main forces for stabilizing the HA trimer. It will be appreciated that HA polypeptides in accordance with the present invention may contain amino acid residues and/or sequences from any HA domain (e.g., core HA-1, transmembrane HA-2, and/or combinations thereof).

In some embodiments, an HA polypeptide in accordance with the present invention contains sequences that are conserved across more than one influenza subtype. For example, analysis of HA sequences from all influenza subtypes showed a set of amino acids in the interface of the HA-1 (head) and HA-2 (stalk) domains that are well conserved and accessible to prospective therapeutic molecules. Studies have also observed the excellent broad spectrum conservation of the HA-1/HA-2 interface membrane proximal epitope region (MPER) that includes the canonical α-helix and residues in its vicinity (Ekiert et al., Science., 324 (5924):246, 2009; Sui et al., *Nat Struct Mol Biol.* 16(3):265, 2009).

HA Receptors

HA polypeptides as described herein interact with the surface of cells by binding to a glycoprotein receptor, known as the HA receptor. Binding of an HA polypeptide to an HA receptor is predominantly mediated by N-linked glycans on the HA receptors. Specifically, HA polypeptides on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells.

Natural HA (and in many embodiments, HA polypeptides) exist in the viral membrane as a homotrimer of one of 16 subtypes, termed H1-H16. Only three of these subtypes (H1, H2, and H3) have thus far become adapted for human infection. One reported characteristic of HA polypeptides that have adapted to infect humans (e.g., of HA polypeptides from the pandemic H1N1 (1918) and H3N2 (1967-68) influenza subtypes) is their ability to preferentially bind to α2,6 sialylated glycans in comparison with their avian progenitors that preferentially bind to α2,3 sialylated glycans (Skehel & Wiley, *Annu Rev Biochem,* 69:531, 2000; Rogers, & Paulson, *Virology,* 127:361, 1983; Rogers et al., *Nature,* 304:76, 1983; Sauter et al., *Biochemistry,* 31:9609, 1992; Connor et al., *Virology,* 205:17, 1994; Tumpey et al., *Science,* 310:77, 2005).

Without wishing to be bound by any particular theory, it has been proposed that the ability to infect human hosts correlates less with binding to glycans of a particular linkage, and more with binding to glycans of a particular topology. We have specifically demonstrated that HA polypeptides that mediate infection of humans bind to umbrella topology glycans, often showing preference for umbrella topology glycans over cone topology glycans (even though cone-topology glycans may be a2,6 sialylated glycans) (See, for example, U.S. Ser. No. 12/348,266 filed Jan. 2, 2009, U.S. Ser. No. 12/301,126, filed Nov. 17, 2008, U.S. Ser. No. 61/018,783, filed Jan. 3, 2008, U.S. Ser. No. 11/969,040, filed Jan. 3, 2008, U.S. Ser. No. 11/893,171, filed Aug. 14, 2007, U.S. Ser. No. 60/837,868, filed on Aug. 14, 2006, U.S. Ser. No. 60/837,869, filed on August 14, and to PCT application PCT/US07/18160, filed Aug. 14, 2007, each of which is incorporated herein by reference).

Several crystal structures of HA polypeptides from H1 (human and swine), H3 (avian) and H5 (avian) subtypes bound to sialylated oligosaccharides (of both α2,3 and α2,6 linkages) are available and provide molecular insights into the specific amino acids that are involved in distinct interactions of the HA polypeptides with these glycans (Eisen et al., *Virology,* 232:19, 1997; Ha et al., *Proc Natl Acad Sci USA,* 98:11181, 2001; Ha et al., *Virology,* 309:209, 2003; Gamblin et al., *Science,* 303:1838, 2004; Stevens et al., *Science,* 303:1866, 2004; Russell et al., *Glycoconj J* 23:85, 2006; Stevens et al., *Science,* 312:404, 2006). Some crystal structures of exemplary HA-glycan interactions have been identified and are presented in Table 1 below.

TABLE 1

Crystal Structures of HA-Glycan Complexes

| Abbreviation (PDB ID) | Virus Strain | Glycan (with assigned coordinates) |
| --- | --- | --- |
| ADkALB76_H1_26 (2WRH) | A/duck/Alberta/76 (H1N1) | Neu5Ac |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| ASC18_H1_26 (2WRG) | A/South Carolina/1/18 (H1N1) | Neu5Acα6Galβ4GlcNAcβ3Gal |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ACkNY91_H2_23 (2WR2) | A/chicken/NY/29878/91 (H2N2) | Neu5Acα3Galβ4GlcNAc |
| AckNY91_H2_26 (2WR1) | A/chicken/NY/29878/91 (H2N2) | Neu5Acα6Galβ4GlcNAc |
| AdkON77_H2_23 (2WR3) | A/duck/Ontario/77 (H2N2) | Neu5Acα3Galβ4GlcNAc |
| AdkON77_H2_26 (2WR4) | A/duck/Ontario/77 (H2N2) | Neu5Acα6Galβ4GlcNAc |
| AckPD84_H2_26 (2WRF) | A/chicken/Potsdam/475/84 (H2N2) | Neu5Acα6Gal |
| ASING57_H2_23 (2WRB) | A/Singapore/1/57 (H2N2) | Neu5Ac |
| ASING57_H2_26 (2WR7) | A/Singapore/1/57 (H2N2) | Neu5Acα6Galβ4GlcNAcβ3Gal |
| AJAP57_H2_26(2WRE) | A/Japan/305/57 (H2N2) | Neu5Acα6Gal |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet1203_04_H5 (2FK0) | A/Vietnam/1203/2004 (H5N1) | |
| Viet1194_04_H5 (2IBX) | A/Vietnam/1194/2004 (H5N1) | |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/l/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

HA—α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2-6 sialylated glycans are published (Eisen et al, 1997, Virology, 232:19; incorporated herein by reference), their coordinates were not available in the Protein Data Bank. The SARF2 program was used to obtain the structural alignment of the different HA1 subunits for superimposition.

For example, crystal structures of H5 (A/duck/Singapore/3/97) alone or bound to an α2,3 or an α2,6 sialylated oligosaccharide identifies certain amino acids that interact directly with bound glycans, and also amino acids that are one or more degree of separation removed (Stevens et al., Proc Natl Acad Sci USA 98:11181, 2001). In some cases, conformation of these residues is different in bound versus unbound states. For instance, Glu190, Lys193 and Gln226 all participate in direct-binding interactions and have different conformations in the bound versus the unbound state. The conformation of Asn186, which is proximal to Glu190, is also significantly different in the bound versus the unbound state.

Without wishing to be bound by any particular theory, it is thought that the HA receptors are modified by either α2,3 or α2,6 sialylated glycans near the receptor's HA polypeptide-binding site, and the type of linkage of the receptor-bound glycan can affect the conformation of the receptor's HA polypeptide-binding site, thus affecting the receptor's specificity for different HA polypeptides. For example, the glycan binding pocket of avian HA receptor is narrow. Without wishing to be bound by any particular theory, it has been proposed that this pocket binds to the trans conformation of α2,3 sialylated glycans, and/or to cone-topology glycans, whether α2,3 or α2,6 linked.

HA receptors in avian tissues, and also in human deep lung and gastrointestinal (GI) tract tissues are characterized by α2,3 sialylated glycan linkages, and furthermore are characterized by glycans, including α2,3 sialylated and/or α2,6 sialylated glycans, which predominantly adopt cone topologies. HA receptors having such cone-topology glycans may be referred to herein as CTHArs.

By contrast, human HA receptors in the bronchus and trachea of the upper respiratory tract are modified by α2,6 sialylated glycans. Unlike the α2,3 motif, the α2,6 motif has an additional degree of conformational freedom due to the C6-C5 bond (Russell et al., Glycoconj J23:85, 2006). HA polypeptides that bind to such α2,6 sialylated glycans have a more open binding pocket to accommodate the diversity of structures arising from this conformational freedom. Moreover, according to the present invention, HA polypeptides may need to bind to glycans (e.g., α2,6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild type avian HA polypeptides (e.g., avian H5). Specifically, because the portions of the human respiratory tract that are most likely to encounter virus (i.e., the trachea and bronchi) lack receptors with cone glycans (e.g., α2,3 sialylated glycans, and/or short glycans) and wild type avian HA polypeptides typically bind primarily or exclusively to receptors associated with cone glycans (e.g., α2,3 sialylated glycans, and/or short glycans), humans rarely become infected with avian viruses. Only when in sufficiently close contact with virus that it can access the deep lung and/or gastrointestinal tract receptors having umbrella glycans (e.g., long α2,6 sialylated glycans) do humans become infected.

Symptoms and Effects of Influenza Infection

Influenza infection or "flu" is a viral infection predominantly of the nose, throat and bronchial tubes of the human body. As described above, given the presence of several different influenza strains and subtypes, severity of the symptoms associate with influenza infection can vary depending on the type of infection. Symptoms can also become life threatening in those individuals with chronic underlying illnesses (such as cancer, emphysema or diabetes) or those who are immunocompromised. While the severity of the symptoms may vary, there are several hallmark symptoms of an influenza infection such as, but not limited to, inflammation, fever, nausea, weight loss, loss of appetite, rapid breathing, increase heart rate, high blood pressure, body aches, muscle pain, eye pain, fatigue, malaise, dry cough, runny nose, and/or sore throat. As a result, in some embodiments, the manifestation of symptoms within a patient can be used as a prognostic or diagnositc to determine the presence of an influenza infection. In some embodients, the severity and/or change of symptoms may be used to determined the dosing regiment for an influenza treatment, such as administration of a binding agent. In some embodiments, the onset, severity and/or change of symptoms displayed by the patient, may be used to indicte the need for prophylactic treatment of a patient with a binding agent. In some embodiments, the severity, change and/or ameliortion of symptoms may be used to evaluate a patient's response to a specific type or method of influenza treatment.

Antibodies

As described herein, the present invention provides antibodies (e.g., monoclonal antibodies, human antibodies, humanized antibodies, etc.) that bind to HA polypeptides, and in some embodmients bind to multiple influenza strains. In some embodiments, such antibodies are useful in the prophylaxis, treatment, diagnosis, and/or study of influenza.

As used herein, an antibody refers to a polypeptide having structural characteristics of an immunoglobulin, as those are understood in the art. In many embodiments, an antibody is a polypeptide whose amino acid sequence includes one or more structural elements recognized by those skilled in the are as a complimentarity determining region (CDR). In some embodiments, an antibody is a polypeptide whose amino acid sequence includes structural elements recognized by those skilled in the art as an immunoglobulin variable domain. In some embodiments, an antibody is "full length" in that in contains two heavy chains and two light chains, optionally associated by disulfide bonds as occurs with naturally-produced antibodies. In some embodiments, an antibody is a fragment of a full-length antibody in that it contains some, but not all of the sequences found in a full-length antibody. For example, in some embodiments, Examples of antibody fragments include, but are not limited to, Fab, Fab', F(ab')2, scFv, Fv, dsFv diabody, and Fd fragments. In some embodiments, an antibody may comprise a single chain antibody fragment. In some embodiments, an antibody may comprise multiple chains which are linked together, for example by disulfide linkages. In some embodiments, an antibody may comprise a multimolecular complex. In some embodiments, an antibody may comprises at least about 50 amino acids and more typically comprises at least about 200 amino acids.

In some embodiments, an antibody is a member an antibody class selected from the group consisting of IgG, IgM, IgA, IgD, and IgE. In some embodiments, an antibody is produced by a cell. In some embodiments, an antibody is produced using a recombinant cell culture system. In some embodiments, an antibody is produced by chemical synthesis. In some embodiments, an antibody is a monoclonal antibody. In some embodiments, an antibody is a polyclonal antibody. In some embodiments, an antibody is produced by chemical synthesis. In some embodiments, an antibody is derived from a mammal. In some embodiments, an antibody is produced by an animal such as, but not limited to, mouse, rat, horse, pig, or goat. In some embodiments, an antibody is a derived from a human. In some embodiments an antibody is a chimeric antibody, for example, from mouse, rat, horse, pig, or other species, bearing human constant and/or variable regions domains. In some embodiments, an antibody is a humanized antibody. As used herein, the term "humanized" antibody refers to an immunoglobulin comprising a human framework region and one or more CDR's from a non-human (e.g., mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

Antibody Modification

In some embodiments, one or more sequences in a provided antibody has been engineered (e.g., by affinity maturation or other optimization approach) to improve one or more characteristics or activities (e.g., to increase stability, decrease aggregation, decrease immunogenicity, etc) as is known in the art. In some embodiments, an antibody is modified by PEGylation, methylation, sialylation, amination or sulfation. In some embodiments, an antibody is conjugated to an amphiphilic core/shell to produce a polymeric micelle. In some embodiments, an antibody is conjugated to a hyperbranched macromolecule (i.e. dendrimer). In some embodiments, an antibody is conjugated to a natural polymer selected from the group consisting of albumin, chitosan, heparin, paclitaxel, poly-(L-glutamate), N-(2-hydroxypropyl)methacrylamide (HPMA), poly-(L-lactide) (PLA), poly (amidoamine) (PAMAM), folate and/or combinations thereof. In some embodiments, an antibody comprises one or more long unstructured tails of hydrophilic amino acids (rPEG). In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology may exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987).

Provided anti-HA Antibodies

The present disclosure provides certain antibodies that bind to influenza HA. The present invention particularly provides certain antibodies which are characterized by binding to a particular HA eptitope and/or to a HA from one or more influenza groups. In some embodiments, such antibodies are characterized by binding to a particular HA eptitope and/or to an HA from a group 1 virus. In some embodiments, such antibodies are characterized by binding to a particular HA eptitope and/or to an HA from a group 2 virus. In some embodiments, such antibodies are characterized by binding to a particular HA eptitope and/or to an HA from a group 1 virus and a group 2 virus. In some embodiments, such antibodies bind to a HA polypeptides of subtype H1, H2, H3, H4, H5, H6, H7, H8, H9, H10, H11, H12, H13, H14, H15, and/or H16. Specifically, in some embodiments, such antibodies bind to HA polypeptides that have sequence elements characteristic of one or more of H1, H2, H3, H4, H5, H6, H7, H8, H9, H10, H11, H12, H13, H14, H15 and H16 HA polypeptides. In some embodiments, such antibodies bind to one or more of H1, H2, H3, H4, H5, H6, H7, H8, H9, H10, H11, H12, H13, H14, H15 and H16 HA polypeptides with an affinity that is at least 5%, 10%, 15%, 20%, 25%, 30%, 35%, 40%, 45%, 50%, 55%, 60%, 65%, 70%, 75%, 80%, 85%, 90% or more of its affinity for one or more of a different H1, H2, H3, H4, H5, H6, H7, H8, H9, H10, H11, H12, H13, H14, H15 and H16 HA polypeptides. In some embodiments such antibodies show binding affinities for different HA polypeptides (e.g., HA polypeptides from different groups, clades, or clusters and/or from different strains) that are within 5 fold binding affinity of one another. In some embodiments such antibodies show binding affinities for different HA polypeptides that are within 2 fold of one another. In some embodiments such antibodies show binding affinities for different HA polypeptides (e.g., HA polypeptides from different groups, clades, or clusters and/or from different strains) that are within 150 fold (e.g., within 100 fold, within 50 fold, within 25 fold, within 10 fold, or within 5 fold) binding affinity of one another.

In some embodiments, such antibodies bind to at least two of H1, H3, H5, H7, and/or H9 HA polypeptides. In some embodiments, such antibodies bind to at least three, four or five of the H1, H3, H5, H7, and/or H9 HA polypeptides.

In some embodiments, such antibodies bind to HA polypeptides of at least one of subtypes H1, H2, H3, H4, H5, H6, H7, H8, H9, H10, H11, H12, H13, H14, H15, and/or H16, and do not bind to at least one HA polypeptide of subtypes H1, H2, H3, H4, H5, H6, H7, H8, H9, H10, H11, H12, H13, H14, H15, and/or H16. In some embodiments, such antibodies bind to HA polypeptides of subtype H1. In some embodiments, such antibodies bind to HA polypeptides of subtype H1 with an affinity at least 100%, at least 125%, at least 150%, at least 200% or more of that with which it binds to HA polypeptides of at least one subtype H2, H3, H4, H5, H6, H7, H8, H9, H10, H11, H12, H13, H14, H15, and/or H16. In some embodiments, such antibodies bind to HA polypeptides of subtype H3. In some embodiments, such antibodies bind to HA polypeptides of subtype H3 with an affinity at least 100%, at least 125%, at least 150%, at least 200% or more of that with which it binds to HA polypeptides of at least one subtype H1, H2, H4, H5, H6, H7, H8, H9, H10, H11, H12, H13, H14, H15, and/or H16.

In some embodiments, such antibodies show a neutralization IC50 (ug/ml) within a range as described and/or exemplified herein. In some embodiments, such provided antibodies show a neutralization IC50 (ug/ml) whose lower bound is about 0.1 ug/ml and upper bound is about 10 ug/ml. In some embodiments, such provided antibodies show a neutralization $IC_{50}$ (ug/ml) whose lower bound is selected from the group consisting of 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0 or more ug/ml, and whose upper bound is higher than the lower bound and is selected from the group consisting of 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0 or more ug/ml.

In some embodiments, such provided antibodies show binding to influenza HA (e.g., group 1 and/or group 2 subtypes) with a $K_D$ (nM) less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, or less than 50 nM.

In some embodiments, such provided antibodies show binding to influenza HA with a $K_a$ ($M^{-1}s^{-1}$) whose lower bound is about $0.01 \times 10^5$ $M^{-1}s^{-1}$ and upper bound is about $1.0 \times 10^6$ $M^{-1}s^{-1}$. such provided antibodies show binding to influenza HA with a $K_a$ ($M^{-1}s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0 \times 10^5$, $1.2 \times 10^5$, $1.4 \times 10^5$, $1.6 \times 10^5$, $1.8 \times 10^5$, $2.0 \times 10^5$, or more $M^{-1}s^{-1}$, and whose upper bound is higher than the lower bound and is slected from the group consisting of $1.0 \times 10^5$, $1.5 \times 10^5$, $2.0 \times 10^5$, $2.5 \times 10^5$, $3.0 \times 10^5$, $3.5 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or more $M^{-1}s^{-1}$.

In some embodiments, such provided antibodies show binding to influenza HA with a $K_d$ ($s^{-1}$) whose lower bound is about $0.01 \times 10^5$ $s^{-1}$ and upper bound is about $1.0 \times 10^6$ $s^{-1}$. such provided antibodies show binding to influenza HA with a $K_a$ ($s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0 \times 10^5$, $1.2 \times 10^5$, $1.4 \times 10^5$, $1.6 \times 10^5$, $1.8 \times 10^5$, $2.0 \times 10^5$, or more $s^{-1}$, and whose upper bound is higher than the lower bound and is slected from the group consisting of $1.0 \times 10^5$, $1.5 \times 10^5$, $2.0 \times 10^5$, $2.5 \times 10^5$, $3.0 \times 10^5$, $3.5 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$ $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or more $s^{-1}$.

In some embodiments, such provided antibodies are characterized by a specific structural feature. In some embodiments, such structural features of such certain provided antibodies include one or more CDRs or one or more FRs at least 65, 70, 75, 80, 85, 86, 87, 88, 89, 90, 91, 92, 93, 94, 95, 96, 97, 98 or 99% identical in sequence to a corresponding CDR or FR from Tables 2 and 3 (SEQ ID NO: 1-60). In some embodiments, such structural features of such certain provided antibodies include one or more CDRs or one or more FRs comprising at least 65, 70, 75, 80, 85, 86, 87, 88, 89, 90, 91, 92, 93, 94, 95, 96, 97, 98 or 99% homology to a corresponding CDR or FR from Tables 2 and 3 (SEQ ID NO: 1-60). In some embodiments, such structural features of such certain provided antibodies include one or more CDRs and/or one or more FRs that is identical in sequence to a corresponding CDR or FR from Tables 2 and 3 (SEQ ID NO: 1-60). In some embodiments, such structural features of such certain provided antibodies include CDRs and FRs that are identical in sequence to those set forth in Tables 2 and 3 (SEQ ID NO: 1-60).

TABLE 2

Exemplary Amino Acid Sequence of VH Chain (CDR Sequences in bold)

| VH Framework | Exemplary Amino Acid Sequence (CDR Sequences in bold) | CDR 1 | CDR 2 | CDR 3 |
|---|---|---|---|---|
| 1 | EVQLLESGGGLVKPGQSLKLSCAASGFTFTSYGMHWVRQPPGKGLEWVAVISYDGSYKYYADSVQGRFTISRDNSKNTLYLQMNSLRAEDTAVYYCAKDSELRSLLYFEWLSQGYFNPWGAGTTLTVSSASTK (SEQ ID NO: 1) | GFTFTSY (SEQ ID NO: 17) | SYDGSY (SEQ ID NO: 19) | DSELRSLLYFEWLSQGYFNP (SEQ ID NO: 21) |
| 2 | EVQLLESGGGVVQPGRSLKLSCAASGFTFSSYGMHWVRQAPGKGLEWVAVISYDGSNKYYADSVEGRFTISRDNSKNTLYLQMNSLRAEDTAVYYCAKDGKLRSLLYFEWLSSGLLDYWGQGAMVTVSSASTK (SEQ ID NO: 2) | GFTFSSY (SEQ ID NO: 18) | SYDGSN (SEQ ID NO: 20) | DGKLRSLLYFEWLSSGLLDY (SEQ ID NO: 22) |
| 3 | EVQLLESGGGVVQPGRSLKLSCAASGFTFSSYGMHWVRQAPGKGLEWVAVSYDGSNKYYADSVEGRFTISRDNSKNTLYLQMNSLRAEDTAVYYCAKDGKLRSLLYFEWLSSGLLDYWGQGAMVTVSSASTK (SEQ ID NO: 3) | GFTFSSY (SEQ ID NO: 18) | SYDGSN (SEQ ID NO: 20) | DGKLRSLLYFEWLSSGLLDY (SEQ ID NO: 22) |
| 4 | EVQLLESGGGVVQPGRSLKLSCAASGFTFSSYGMHWVRQAPGKGLEWVAVSYDGSNKYYAPKFEGRFTISRDNSKNTLYLQMNSLRAEDTAVYYCAKDGKLRSLLYFEWLSSGLLDYWGQGAMVTVSSASTK (SEQ ID NO: 4) | GFTFSSY (SEQ ID NO: 18) | SYDGSN (SEQ ID NO: 20) | DGKLRSLLYFEWLSSGLLDY (SEQ ID NO: 22) |
| 5 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCAKDGKLRSLLYFEWLSSGLLDYWGQGAMVTVSSASTK (SEQ ID NO: 5) | GFTFSSY (SEQ ID NO: 18) | SYDGSN (SEQ ID NO: 20) | DGKLRSLLYFEWLSSGLLDY (SEQ ID NO: 22) |
| 6 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCGKDSQLRSLVYFEWLSSGLLDYWGQGAMVTVSSASTK (SEQ ID NO: 6) | GFTFSSY (SEQ ID NO: 18) | SYDGSN (SEQ ID NO: 20) | DSQLRSLVYFEWLSSGLLDY (SEQ ID NO: 23) |
| 7 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCAKDSQLRSLLYFEWLSSGLLDYWGQGAMVTVSSASTK (SEQ ID NO: 7) | GFTFSSY (SEQ ID NO: 18) | SYDGSN (SEQ ID NO: 20) | DSQLRSLLYFEWLSSGLLDY (SEQ ID NO: 24) |
| 8 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCAKDSKLRSLLYFEWLSSGLLDYWGQGAMVTVSSASTK (SEQ ID NO: 8) | GFTFSSY (SEQ ID NO: 18) | SYDGSN (SEQ ID NO: 20) | DSKLRSLLYFEWLSSGLLDY (SEQ ID NO: 22) |
| 9 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCAKDTQLRTIVYFEWLSQGFYDIWGQGAMVTVSSASTK (SEQ ID NO: 9) | GFTFSSY (SEQ ID NO: 18) | SYDGSN (SEQ ID NO: 20) | DTQLRTIVYFEWLSQGFYDI (SEQ ID NO: 25) |
| 10 | EVQLLESGGGLVKPGQSLKLSCAASGFTFSSYGMHWVRQPPGKGLEWVAVSYDGSNKYYADSVQGRFTISRDNSKNTLYLQMNSLRAEDTAVYYCAKDSQLRTIVYFEWLSQGYFDPWGQGAMVTVSSASTK (SEQ ID NO: 10) | GFTFSSY (SEQ ID NO: 18) | SYDGSN (SEQ ID NO: 20) | DSQLRTIVYFEWLSQGYFDP (SEQ ID NO: 26) |
| 11 | EVQLLESGGGLVKPGQSLKLSCAASGFTFSSYGMHWVRQPPGKGLEWVAVSYDGSYKYYADSVQGRFTISRDNSKNTLYLQMNSLRAEDTAVYYCAKDS | GFTFSSY (SEQ ID NO: 18) | SYDGSY (SEQ ID NO: 19) | DSQLRSLLYFEWLSSGLLDY (SEQ ID NO: 27) |

TABLE 2-continued

Exemplary Amino Acid Sequence of VH Chain (CDR Sequences in bold)

| VH Frame-work | Exemplary Amino Acid Sequence(CDR Sequences in bold) | CDR 1 | CDR 2 | CDR 3 |
|---|---|---|---|---|
| | QLRSLLYFEWLSSGLLDYWGQGAMV TVSSASTK (SEQ ID NO: 11) | | | |
| 12 | EVQLLESGGGLVKPGQSLKLSCAAS GFTFTSYGMHWVRQPPGKGLEWVAV ISYDGSYKYYADSVQGRFTISRDNS KNTLYLQMNSLRAEDTAVYYCGKDS QLRSLIYFEWLSNGYFDIWGAGTTL TVSSASTK (SEQ ID NO: 12) | GFTFTSY (SEQ ID NO: 17) | SYDGSY (SEQ ID NO: 19) | DSQLRSLIYFEWLSNGYFDI (SEQ ID NO: 28) |
| 13 | EVQLLESGGGLVKPGQSLKLSCAAS GFTFTSYGMHWVRQPPGKGLEWVAV ISYDGSYKYYADSVQGRFTISRDNS KNTLYLQMNSLRAEDTAVYYCAKDS QLRSLLYFEWLSNGFYDIWGAGTTL TVSSASTK (SEQ ID NO: 13) | GFTFTSY (SEQ ID NO: 17) | SYDGSY (SEQ ID NO: 19) | DSQLRSLLYFEWLSNGFYDI (SEQ ID NO: 29) |
| 14 | EVQLLESGGGLVKPGQSLKLSCAAS GFTFTSYGMHWVRQPPGKGLEWVAV ISYDGSYKYYADSVQGRFTISRDNS KNTLYLQMNSLRAEDTAVYYCAKDS NLRTIVYFEWLSSGLLDYWGAGTTL TVSSASTK (SEQ ID NO: 14) | GFTFTSY (SEQ ID NO: 17) | SYDGSY (SEQ ID NO: 19) | DSNLRTIVYFEWLSSGLLDY (SEQ ID NO: 30) |
| 15 | EVQLLESGGGLVKPGQSLKLSCAAS GFTFTSYGMHWVRQPPGKGLEWVAV ISYDGSYKYYADSVQGRFTISRDNS KNTLYLQMNSLRAEDTAVYYCAKDS QLRTIVYFEWLSQGYFDPWGAGTTL TVSSASTK (SEQ ID NO: 15) | GFTFTSY (SEQ ID NO: 17) | SYDGSY (SEQ ID NO: 19) | DSQLRTIVYFEWLSQGYFDP (SEQ ID NO: 31) |
| 16 | EVQLLESGGGLVKPGQSLKLSCAAS GFTFTSYGMHWVRQPPGKGLEWVAV ISYDGSYKYYADSVQGRFTISRDNS KNTLYLQMNSLRAEDTAVYYCAKDT QLRTIVYFEWLSQGFYDIWGAGTTL TVSSASTK (SEQ ID NO: 16) | GFTFTSY (SEQ ID NO: 17) | SYDGSY (SEQ ID NO: 19) | DTQLRTIVYFEWLSQGFYDI (SEQ ID NO: 32) |

TABLE 3

Exemplary Amino Acid Sequence of VL Chain (CDR Sequences in bold)

| VL Frame-work | Exemplary Amino Acid Sequence(CDR Sequences in bold) | CDR1 | CDR2 | CDR3 |
|---|---|---|---|---|
| 1 | EIVMTQSPDSLAVSLGERATINC KSSQSVTYNYKNYLAWYQQKPGQ PPKLLIYWASTRESGVPDRFSGS GSGTDFTLTISSLQAEDVAVYYC QQYYRTPPTFGGGTKLDIKGS (SEQ ID NO: 33) | KSSQSVTYNYKNYLA (SEQ ID NO: 44) | WASTRES (SEQ ID NO: 55) | QQYYRTPPT (SEQ ID NO: 59) |
| 2 | DIQMTQSPSSLSASVGDRVTITC RASQDVNTAVAWYQQKPGKAPKL LIYSASFLYSGVPSRFSGSRSGT DFTLTISSLQPEDFATYYCQQHY TTPPTFGQGTKVEIKGS(SEQ ID NO: 34) | RASQDVNTAVA (SEQ ID NO: 45) | SASFLYS (SEQ ID NO: 56) | QQHYTTPPT (SEQ ID NO: 60) |
| 3 | DIQMTQSPSSLSASVGDRVTITC RASQDIPRSISGYVAWYQQKPGK APKLLIYWGSYLYSGVPSRFSGS RSGTDFTLTISSLQPEDFATYYC QQHYTTPPTFGQGTKVEIKGS (SEQ ID NO: 35) | RASQDIPRSISGYVA (SEQ ID NO: 46) | WGSYLYS (SEQ ID NO: 57) | QQHYTTPPT (SEQ ID NO: 60) |
| 4 | DIQMTQSPSSLSASVGDRVTITC RASQDIPFSYKGYVAWYQQKPGK APKLLIYWGSYLESGVPSRFSGS GSGTDFTLTISSLQPEDFATYYC | RASQDIPFSYKGYVA (SEQ ID NO: 47) Exemplary VL Chain | WGSYLES (SEQ ID NO: 57) | QQHYTTPPT (SEQ ID NO: 60) |

TABLE 3-continued

Exemplary Amino Acid Sequence of VL Chain (CDR Sequences in bold)

| VL Frame-work | Exemplary Amino Acid Sequence (CDR Sequences in bold) | CDR1 | CDR2 | CDR3 |
|---|---|---|---|---|
|  | QQHYTTPPTFGQGTKVEIKGS (SEQ ID NO: 36) |  |  |  |
| 5 | DIQMTQSPSSLSASVGDRVTITCRASQSITFDYKNYVAWYQQKPGKAPKLLIYWGSYLEGVPSRFSGSGSGTDFTLTISSLQPEDFATYYCQQHYTTPPTFGQGTKVEIKGS (SEQ ID NO: 37) | RASQSITFDYKNYVA (SEQ ID NO: 48) | WGSYLE (SEQ ID NO: 58) | QQHYTTPPT (SEQ ID NO: 60) |
| 6 | DIQMTQSPSSLSASVGDRVTITCRASQSITFNYKNYVAWYQQKPGKAPKLLIYWGSYLESGVPSRFSGSGSGTDFTLTISSLQPEDFATYYCQQHYTTPPTFGQGTKVEIKGS (SEQ ID NO: 38) | RASQSITFNYKNYVA (SEQ ID NO: 49) | WGSYLES (SEQ ID NO: 57) | QQHYTTPPT (SEQ ID NO: 60) |
| 7 | DIQMTQSPSSLSASVGDRVTITCRASQSITFSYKNYVAWYQQKPGKAPKLLIYWGSYLESGVPSRFSGSGSGTDFTLTISSLQPEDFATYYCQQHYTTPPTFGQGTKVEIKGS (SEQ ID NO: 39) | RASQSITFSYKNYVA (SEQ ID NO: 50) | WGSYLES (SEQ ID NO: 57) | QQHYTTPPT (SEQ ID NO: 60) |
| 8 | DIQMTQSPSSLSASVGDRVTITCRASQDIPFSYKGYVAWYQQKPGKAPKVLIYWGSYLESGVPSRFSGSGSGTDFTLTISSLQPEDFATYYCQQHYTTPPTFGQGTKVEIKGS (SEQ ID NO: 40) | RASQDIPFSYKGYVA (SEQ ID NO: 51) | WGSYLES (SEQ ID NO: 57) | QQHYTTPPT (SEQ ID NO: 60) |
| 9 | DIQMTQSPSSLSASVGDRVTITCRASQSITFDYKNYVAWYQQKPGKAPKVLIYWGSYLESGVPSRFSGSGSGTDFTLTISSLQPEDFATYYCQQHYTTPPTFGQGTKVEIKGS (SEQ ID NO: 41) | RASQSITFDYKNYVA (SEQ ID NO: 52) | WGSYLES (SEQ ID NO: 57) | QQHYTTPPT (SEQ ID NO: 60) |
| 10 | DIQMTQSPSSLSASVGDRVTITCRASQSITFNYKNYVAWYQQKPGKAPKVLIYWGSYLESGVPSRFSGSGSGTDFTLTISSLQPEDFATYYCQQHYTTPPTFGQGTKVEIKGS (SEQ ID NO: 42) | RASQSITFNYKNYVA (SEQ ID NO: 53) | WGSYLES (SEQ ID NO: 57) | QQHYTTPPT (SEQ ID NO: 60) |
| 11 | DIQMTQSPSSLSASVGDRVTITCRASQSITFSYKNYVAWYQQKPGKAPKVLIYWGSYLESGVPSRFSGSGSGTDFTLTISSLQPEDFATYYCQQHYTTPPTFGQGTKVEIKGS (SEQ ID NO: 43) | RASQSITFSYKNYVA (SEQ ID NO: 54) | WGSYLES (SEQ ID NO: 57) | QQHYTTPPT (SEQ ID NO: 60) |

In some embodiments, such structural features include CDR and FR sequence elements, each of which is identical to a reference CDR or FR sequence element set forth in Table 2 and/or Table 3 (SEQ ID NOs:1-60) except that it includes one or more amino acid substitutions with respect to that reference sequence element, where the included CDR and FR sequence elements together contain no more than 18, 17, 16, 15, 14, 13, 12, 11, 10, 9, 8, 7, 6, 5, 4, 3, 2, or 1 substitutions in CDR and FR sequences, as compared with the corresponding CDR and FR reference sequence elements from Tables 2 and 3 (SEQ ID NO: 1-60). In some embodiments, such structural features include CDR and FR sequence elements together contain no more than 18 substitutions as compared with the corresponding CDR and FR reference sequence elements from Tables 2 and 3 (SEQ ID NO: 1-60). In some embodiments, such structural features include CDR and FR sequence elements together contain no more than 15 substitutions as compared with the corresponding CDR and FR reference sequence elements from Tables 2 and 3 (SEQ ID NO: 1-60).

In some embodiments, such structural features include a FR sequence element, which is identical to a reference FR sequence element set forth in Table 2 and/or Table 3 (SEQ ID NOs:1-60) except that it includes one or more amino acid substitutions with respect to that reference sequence element, where the included FR sequence element contains no more than 18, 17, 16, 15, 14, 13, 12, 11, 10, 9, 8, 7, 6, 5, 4, 3, 2, or 1 substitutions in FR sequence, as compared with the corresponding FR reference sequence elements from Tables 2 and 3 (SEQ ID NO: 1-60).

In some embodiments, such structural features include a CDR sequence element, which is identical to a reference CDR sequence element set forth in Table 2 and/or Table 3 (SEQ ID NOs:1-60) except that it includes one or more amino acid substitutions with respect to that reference sequence element, where the included CDR sequence element contains no more than 18, 17, 16, 15, 14, 13, 12, 11, 10, 9, 8, 7, 6, 5, 4, 3, 2, or 1 substitutions in CDR sequence, as compared with the corresponding CDR reference sequence elements from Tables 2 and 3 (SEQ ID NO: 1-60).

In some embodiments, such structural features include a VH sequence element, which is identical to a reference VH sequence element set forth in Table 2 and/or Table 3 (SEQ ID NOs:1-60) except that it includes one or more amino acid substitutions with respect to that reference sequence element, where the included VH sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof, as compared with the corresponding VH reference sequence elements from Tables 2 and 3 (SEQ ID NO: 1-60).

In some embodiments, such structural features include a VL sequence element, which is identical to a reference VL sequence element set forth in Table 2 and/or Table 3 (SEQ ID NOs:1-60) except that it includes one or more amino acid substitutions with respect to that reference sequence element, where the included VL sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VL-1, VL-2, VL-3, VL-4, VL-5, VL-6, VL-7, VL-8, VL-9, VL-10, VL-11, or fragment thereof, as compared with the corresponding VL reference sequence elements from Tables 2 and 3 (SEQ ID NO: 1-60).

In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof combined with any one of VL-1, VL-2, VL-3, VL-4, VL-5, VL-6, VL-7, VL-8, VL-9, VL-10, VL-11, or fragment thereof. In some embodiments, VH-1 (SEQ ID NO:1) is combined with VL-1 (SEQ ID NO:33).

In some embodiments, such structural features include a complementarity determining region (CDR) 1 sequence element that shows at least 65%, more than 70%, more than 75%, more than 80%, more than 85%, more than 90%, more than 95%, or more than 99% identity with a reference CDR1 sequence element from Tables 2 and/or 3 (SEQ ID NOs:17-18 and/or SEQ ID NOs:44-54). In some embodiments, such structural features include a complementarity determining region (CDR) 1 sequence element that has two or more amino acid substitutions as compared to a reference CDR1 sequence element from Tables 2 and 3 (SEQ ID NOs:17-18 and/or SEQ ID NOs:44-54). In some embodiments, such structural features include a complementarity determining region (CDR) 1 sequence element that has one or more amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has at least two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has fewer than two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has an amino acid sequence that is identical to that of one of the reference CDR1 sequence elements from Tables 2 and 3 (SEQ ID NOs:17-18 and/or SEQ ID NOs:44-54).

In some embodiments, such structural features include a complementarity determining region (CDR) 2 sequence element that shows at least 65%, more than 70%, more than 75%, more than 80%, more than 85%, more than 90%, more than 95%, or more than 99% identity with a reference CDR2 sequence element from Tables 2 and/or 3 (SEQ ID NOs:17-18 and/or SEQ ID NOs:44-54). In some embodiments, such structural features include a complementarity determining region (CDR) 2 sequence element that has two or more amino acid substitutions as compared to a reference CDR2 sequence element from Tables 2 and 3 (SEQ ID NOs:17-18 and/or SEQ ID NOs:44-54). In some embodiments, such structural features include a complementarity determining region (CDR) 2 sequence element that has one or more amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has at least two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has fewer than two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has an amino acid sequence that is identical to that of one of the reference CDR2 sequence elements from Tables 2 and 3 (SEQ ID NOs:17-18 and/or SEQ ID NOs:44-54).

In some embodiments, such structural features include a complementarity determining region (CDR) 3 sequence element that shows at least 65%, more than 70%, more than 75%, more than 80%, more than 85%, more than 90%, more than 95%, or more than 99% identity with a reference CDR3 sequence element from Tables 2 and/or 3 (SEQ ID NOs:17-18 and/or SEQ ID NOs:44-54). In some embodiments, such structural features include a complementarity determining region (CDR) 3 sequence element that has two or more amino acid substitutions as compared to a reference CDR3 sequence element from Tables 2 and 3 (SEQ ID NOs:17-18 and/or SEQ ID NOs:44-54). In some embodiments, such structural features include a complementarity determining region (CDR) 3 sequence element that has one or more amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has at least two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has fewer than two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has an amino acid sequence that is identical to that of one of the reference CDR3 sequence elements from Tables 2 and 3 (SEQ ID NOs:17-18 and/or SEQ ID NOs:44-54).

In some embodiments, such structural features include a VH framework region sequence element that shows more than 65%, more than 70%, more than 75%, more than 80%, more than 85%, more than 90%, more than 95%, or more than 99% percent identity with a reference VH framework region sequence element from Table 2 (SEQ ID NOs:1-16).

In some embodiments, such structural features include a VL framework region sequence element that shows more than 65%, more than 70%, more than 75%, more than 80%, more than 85%, more than 90%, more than 95%, or more than 99% percent identity with a reference VL framework region sequence element from Table 3 (SEQ ID NOs:33-43).

Binding Agents
Structures and Features

The present disclosure provides influenza binding agents. The present invention particularly provides binding agents that include such structural features of such certain provided antibodies such that the provided binding agent shares with the certain provided influenza antibodies the functional attribute that it binds to a particular HA eptitope and/or to a HA from a specific influenza group. In some embodiments, such binding agent is characterized by a functional attribute of binding to a particular HA eptitope and/or to a HA from a group 1 virus. In some embodiments, such binding agent is characterized by a functional attribute of binding to a particular HA eptitope and/or to a HA from a group 2 virus. In some embodiments, such binding agent is characterized by a functional attribute of binding to a particular HA eptitope and/or to a HA from a group 1 virus and a group 2 virus. In some embodiments, such binding agent is characterized by a functional attribute of binding to an HA polypeptides of subtype H1, H2, H3, H4, H5, H6, H7, H8, H9, H10, H11, H12, H13, H14, H15, and/or H16. Specifically, in some embodiments, such binding agent is characterized by a functional attribute of binding to HA polypeptides that have sequence elements characteristic of one or more of H1, H2, H3, H4, H5, H6, H7, H8, H9, H10, H11, H12, H13, H14, H15 and H16 HA polypeptides. In some embodiments, such binding agent is characterized by a functional attribute of binding to one or more of H1, H2, H3, H4, H5, H6, H7, H8, H9, H10, H11, H12, H13, H14, H15 and H16 HA polypeptides with an affinity that is at least 5%, 10%, 15%, 20%, 25%, 30%, 35%, 40%, 45%, 50%, 55%, 60%, 65%, 70%, 75%, 80%, 85%, 90% or more of its affinity for one or more of a different H1, H2, H3, H4, H5, H6, H7, H8, H9, H10, H11, H12, H13, H14, H15 and H16 HA polypeptides.

In some embodiments such binding agents show binding affinities for different HA polypeptides (e.g., HA polypeptides from different groups, clades, or clusters and/or from different strains) that are within 5 fold binding affinity of one another. In some embodiments such binding agents show binding affinities for different HA polypeptides that are within 2 fold of one another. In some embodiments such binding agents show binding affinities for different HA polypeptides (e.g., HA polypeptides from different groups, clades, or clusters and/or from different strains) that are within 150 fold (e.g., within 100 fold, within 50 fold, within 25 fold, within 10 fold, or within 5 fold) binding affinity of one another.

In some embodiments, such binding agents are characterized by a functional attribute of binding to at least two of H1, H3, H5, H7, and/or H9 HA polypeptides. In some embodiments, such binding agents are characterized by a functional attribute of binding to at least three, four or five of the H1, H3, H5, H7, and/or H9 HA polypeptides.

In some embodiments, such binding agents are characterized by a functional attribute of binding to at least one of subtypes H1, H2, H3, H4, H5, H6, H7, H8, H9, H10, H11, H12, H13, H14, H15, and/or H16, and do not bind to at least one HA polypeptide of subtypes H1, H2, H3, H4, H5, H6, H7, H8, H9, H10, H11, H12, H13, H14, H15, and/or H16. In some embodiments, such binding agents bind to HA polypeptides of subtype H1. In some embodiments, such binding agents bind to HA polypeptides of subtype H1 with an affinity at least 100%, at least 125%, at least 150%, at least 200% or more of that with which it binds to HA polypeptides of at least one subtype H2, H3, H4, H5, H6, H7, H8, H9, H10, H11, H12, H13, H14, H15, and/or H16. In some embodiments, such binding agents bind to HA polypeptides of subtype H3. In some embodiments, such binding agents bind to HA polypeptides of subtype H3 with an affinity at least 100%, at least 125%, at least 150%, at least 200% or more of that with which it binds to HA polypeptides of at least one subtype H1, H2, H4, H5, H6, H7, H8, H9, H10, H11, H12, H13, H14, H15, and/or H16.

In some embodiments, such binding agents are characterized by a functional attribute of showing a neutralization IC50 (ug/ml) within a range as described and/or exemplified herein. In some embodiments, such binding agents show a neutralization $IC_{50}$ (ug/ml) whose lower bound is about 0.1 ug/ml and upper bound is about 10 ug/ml. In some embodiments, such binding agents show a neutralization $IC_{50}$ (ug/ml) whose lower bound is selected from the group consisting of 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0 or more ug/ml, and whose upper bound is higher than the lower bound and is selected from the group consisting of 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0 or more ug/ml.

In some embodiments, such provided binding agent shows binding to influenza HA (e.g., group 1 and/or group 2 subtypes) with a $K_D$ (nM) less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, or less than 50 nM.

In some embodiments, such provided binding agent shows binding to influenza HA with a $K_a$ ($M^{-1}s^{-1}$) whose lower bound is about $0.01 \times 10^5$ $M^{-1}s^{-1}$ and upper bound is about $1.0 \times 10^6$ $M^{-1}s^{-1}$. such provided antibodies show binding to influenza HA with a $K_a$ ($M^{-1}s^{-1}$) whose lower bound is selected from the group consisting of $0.01 \times 10^5$, $0.02 \times 10^5$, $0.04 \times 10^5$, $0.04 \times 10^5$, $0.08 \times 10^5$, $0.1 \times 10^5$, $0.2 \times 10^5$, $0.4 \times 10^5$, $0.6 \times 10^5$, $0.8 \times 10^5$, $1.0 \times 10^5$, $1.2 \times 10^5$, $1.4 \times 10^5$, $1.6 \times 10^5$, $1.8 \times 10^5$, $2.0 \times 10^5$, or more $M^{-1}s^{-1}$, and whose upper bound is higher than the lower bound and is slected from the group consisting of $1.0 \times 10^5$, $1.5 \times 10^5$, $2.0 \times 10^5$, $2.5 \times 10^5$, $3.0 \times 10^5$, $3.5 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $1.0 \times 10^6$ $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, or more $M^{-1}s^{-1}$.

In some embodiments, such provided binding agent shows binding to influenza HA with a $K_d$ ($s^{-1}$) whose lower bound is about $0.01 \times 10^5$ $s^{-1}$ and upper bound is about $1.0 \times 10^6$ $s^{-1}$. such provided antibodies show binding to influenza HA with a $K_a$ (s$^{-1}$) whose lower bound is selected from the group consisting of 0.01×10$^5$, 0.02×10$^5$, 0.04×10$^5$, 0.04×10$^5$, 0.08×10$^5$, 0.1×10$^5$, 0.2×10$^5$, 0.4×10$^5$, 0.6×10$^5$, 0.8×10$^5$, 1.0×10$^5$, 1.2×10$^5$, 1.4×10$^5$, 1.6×10$^5$, 1.8×10$^5$, 2.0× 10$^5$, or more s$^{-1}$, and whose upper bound is higher than the lower bound and is slected from the group consisting of 1.0×10$^5$, 1.5×10$^5$, 2.0×10$^5$, 2.5×10$^5$, 3.0×10$^5$, 3.5×10$^5$, 4.5× 10$^5$, 5.0×10$^5$, 5.5×10$^5$, 6.0×10$^5$, 6.5×10$^5$, 7.0×10$^5$, 7.5×10$^5$, 8.0×10$^5$, 8.5×10$^5$, 9.0×10$^5$, 9.5×10$^5$, 1.0×10$^6$ 1.1×10$^6$, 1.2× 10$^6$, 1.3×10$^6$, 1.4×10$^6$, 1.5×10$^6$, 1.6×10$^6$, 1.7×10$^6$, 1.8×10$^6$, 1.9×10$^6$, or more s$^{-1}$.

In some embodiments, such structural features of such certain binding agents include one or more CDRs or one or more FRs at least 65, 70, 75, 80, 85, 86, 87, 88, 89, 90, 91, 92, 93, 94, 95, 96, 97, 98 or 99% identical in sequence to a corresponding CDR or FR from Tables 2 and 3 (SEQ ID NO: 1-60). In some embodiments, such structural features of such binding agents include one or more CDRs or one or more FRs comprising at least 65, 70, 75, 80, 85, 86, 87, 88, 89, 90, 91, 92, 93, 94, 95, 96, 97, 98 or 99% homology to a corresponding CDR or FR from Tables 2 and 3 (SEQ ID NO: 1-60). In some embodiments, such structural features of such binding agents include one or more CDRs and/or one or more FRs that is identical in sequence to a corresponding CDR or FR from Tables 2 and 3 (SEQ ID NO: 1-60). In some embodiments, such structural features of such binding agents include CDRs and FRs that are identical in sequence to those set forth in Tables 2 and 3 (SEQ ID NO: 1-60).

In some embodiments, such structural features include CDR and FR sequence elements, each of which is identical to a reference CDR or FR sequence element set forth in Table 2 and/or Table 3 (SEQ ID NOs:1-60) except that it includes one or more amino acid substitutions with respect to that reference sequence element, where the included CDR and FR sequence elements together contain no more than 18, 17, 16, 15, 14, 13, 12, 11, 10, 9, 8, 7, 6, 5, 4, 3, 2, or 1 substitutions in CDR and FR sequences, as compared with the corresponding CDR and FR reference sequence elements from Tables 2 and 3 (SEQ ID NO: 1-60). In some embodiments, such structural features include CDR and FR sequence elements together contain no more than 18 substitutions as compared with the corresponding CDR and FR reference sequence elements from Tables 2 and 3 (SEQ ID NO: 1-60). In some embodiments, such structural features include CDR and FR sequence elements together contain no more than 15 substitutions as compared with the corresponding CDR and FR reference sequence elements from Tables 2 and 3 (SEQ ID NO: 1-60).

In some embodiments, such structural features includes a FR sequence element, which is identical to a reference FR sequence element set forth in Table 2 and/or Table 3 (SEQ ID NOs:1-60) except that it includes one or more amino acid substitutions with respect to that reference sequence element, where the included FR sequence element contains no more than 18, 17, 16, 15, 14, 13, 12, 11, 10, 9, 8, 7, 6, 5, 4, 3, 2, or 1 substitutions in FR sequence, as compared with the corresponding FR reference sequence elements from Tables 2 and 3 (SEQ ID NO: 1-60).

In some embodiments, such structural features includes a CDR sequence element, which is identical to a reference CDR sequence element set forth in Table 2 and/or Table 3 (SEQ ID NOs:1-60) except that it includes one or more amino acid substitutions with respect to that reference sequence element, where the included CDR sequence element contains no more than 18, 17, 16, 15, 14, 13, 12, 11, 10, 9, 8, 7, 6, 5, 4, 3, 2, or 1 substitutions in CDR sequence, as compared with the corresponding CDR reference sequence elements from Tables 2 and 3 (SEQ ID NO: 1-60).

In some embodiments, such structural features include a VH sequence element, which is identical to a reference VH sequence element set forth in Table 2 and/or Table 3 (SEQ ID NOs:1-60) except that it includes one or more amino acid substitutions with respect to that reference sequence element, where the included VH sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof, as compared with the corresponding VH reference sequence elements from Tables 2 and 3 (SEQ ID NO: 1-60).

In some embodiments, such structural features include a VL sequence element, which is identical to a reference VL sequence element set forth in Table 2 and/or Table 3 (SEQ ID NOs:1-60) except that it includes one or more amino acid substitutions with respect to that reference sequence element, where the included VL sequence element contains no more than 18, 17, 16, 15, 14, 13, 12, 11, 10, 9, 8, 7, 6, 5, 4, 3, 2, or 1 substitutions in CDR sequence, as compared with the corresponding VH reference sequence elements from Tables 2 and 3 (SEQ ID NO: 1-60). In some embodiments, such structural features include a structural element corresponding to any one of VL-1, VL-2, VL-3, VL-4, VL-5, VL-6, VL-7, VL-8, VL-9, VL-10, VL-11, or fragment thereof, as compared with the corresponding VL reference sequence elements from Tables 2 and 3 (SEQ ID NO: 1-60).

In some embodiments, such structural features include a structural element corresponding to any one of VH-1, VH-2, VH-3, VH-4, VH-5, VH-6, VH-7, VH-8, VH-9, VH-10, VH-11, VH-12, VH-13, VH-14, VH-15, VH-16 or fragment thereof combined with any one of VL-1, VL-2, VL-3, VL-4, VL-5, VL-6, VL-7, VL-8, VL-9, VL-10, VL-11, or fragment thereof. In some embodiments, VH-1 (SEQ ID NO:1) is combined with VL-1 (SEQ ID NO:33).

In some embodiments, such structural features include a complementarity determining region (CDR) 1 sequence element that shows at least 65%, more than 70%, more than 75%, more than 80%, more than 85%, more than 90%, more than 95%, or more than 99% identity with a reference CDR1 sequence element from Tables 2 and/or 3 (SEQ ID NOs:17-18 and/or SEQ ID NOs:44-54). In some embodiments, such structural features include a complementarity determining region (CDR) 1 sequence element that has two or more amino acid substitutions as compared to a reference CDR1 sequence element from Tables 2 and 3 (SEQ ID NOs:17-18 and/or SEQ ID NOs:44-54). In some embodiments, such structural features include a complementarity determining region (CDR) 1 sequence element that has one or more amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has at least two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has fewer than two amino acid substitutions as compared to reference CDR1 sequence element from Tables 2 and 3 (SEQ ID NOs:17-18 and/or SEQ ID NOs:44-54). In some embodiments, such structural features include a complementarity determining region (CDR) 1 sequence element that has an amino acid sequence that is identical to that of one of the reference CDR1 sequence elements from Tables 2 and 3 (SEQ ID NOs:17-18 and/or SEQ ID NOs:44-54).

In some embodiments, such structural features include a complementarity determining region (CDR) 2 sequence element that shows at least 65%, more than 70%, more than 75%, more than 80%, more than 85%, more than 90%, more than 95%, or more than 99% identity with a reference CDR2 sequence element from Tables 2 and/or 3 (SEQ ID NOs:17-18 and/or SEQ ID NOs:44-54). In some embodiments, such structural features include a complementarity determining region (CDR) 2 sequence element that has two or more amino acid substitutions as compared to a reference CDR2 sequence element from Tables 2 and 3 (SEQ ID NOs:17-18 and/or SEQ ID NOs:44-54). In some embodiments, such structural features include a complementarity determining region (CDR) 2 sequence element that has one or more amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has at least two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has fewer than two amino acid substitutions as compared to reference CDR2 sequence element from Tables 2 and 3 (SEQ ID NOs:17-18 and/or SEQ ID NOs:44-54). In some embodiments, such structural features include a complementarity determining region (CDR) 2 sequence element that has an amino acid sequence that is identical to that of one of the reference CDR2 sequence elements from Tables 2 and 3 (SEQ ID NOs:17-18 and/or SEQ ID NOs:44-54).

In some embodiments, such structural features include a complementarity determining region (CDR) 3 sequence element that shows at least 65%, more than 70%, more than 75%, more than 80%, more than 85%, more than 90%, more than 95%, or more than 99% identity with a reference CDR3 sequence element from Tables 2 and/or 3 (SEQ ID NOs:17-18 and/or SEQ ID NOs:44-54). In some embodiments, such structural features include a complementarity determining region (CDR) 3 sequence element that has two or more amino acid substitutions as compared to a reference CDR3 sequence element from Tables 2 and 3 (SEQ ID NOs:17-18 and/or SEQ ID NOs:44-54). In some embodiments, such structural features include a complementarity determining region (CDR) 3 sequence element that has one or more amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has at least two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has fewer than two amino acid substitutions as compared to reference CDR3 sequence element from Tables 2 and 3 (SEQ ID NOs:17-18 and/or SEQ ID NOs:44-54). In some embodiments, such structural features include a complementarity determining region (CDR) 3 sequence element that has an amino acid sequence that is identical to that of one of the reference CDR3 sequence elements from Tables 2 and 3 (SEQ ID NOs:17-18 and/or SEQ ID NOs:44-54).

In some embodiments, such structural features include a VH framework region sequence element that shows more than 65%, more than 70%, more than 75%, more than 80%, more than 85%, more than 90%, more than 95%, or more than 99% percent identity with a reference VH framework region sequence element from Table 2 (SEQ ID NOs:1-16).

In some embodiments, such structural features include a VL framework region sequence element that shows more than 65%, more than 70%, more than 75%, more than 80%, more than 85%, more than 90%, more than 95%, or more than 99% percent identity with a reference VL framework region sequence element from Table 3 (SEQ ID NOs:33-43).

Exemplary Binding Agents
Antibody and/or Antibody Fragment

As used herein, a binding agent refers to an agent that is capable of binding to an antigen or biological target. In some embodiments, a provided binding agent is or comprises a polypeptide. In some embodiments, a provided binding agent is or comprises an antibody or fragment thereof In some embodiments, a provided binding agent is or comprises a monocolonal antibody or fragment thereof. In some embodiments, a provided binding agent is or comprises a polyclonal antibody or fragment thereof. In some embodiments, the binding agent is or comprises a "full length" antibody, in that it contains two heavy chains and two light chains, optionally associated by disulfide bonds as occurs with naturally-produced antibodies. In some embodiments, the binding agent is or comprises a fragment of a full-length antibody in that is contains some, but not all of the sequences found in a full-length antibody. For example, in some embodiments, the binding agent is or comprises antibody fragments which include, but are not limited to, Fab, Fab', F(ab')2, scFv, Fv, dsFv diabody, and Fd fragments. In some embodiments, a provided binding agent is or comprises an antibody that is a member of an antibody class selected from the group consisting of IgG, IgM, IgA, IgD, IgE or fragment thereof. In some embodiments, a provided binding agent is or comprises an antibody produced by chemical synthesis. In some embodiments, a provided binding agent is or comprises an antibody produced by a cell. In some embodiments, a provided binding agent is or comprises an antibody produced using a recombinant cell culture system. In some embodiments, a provided binding agent is or comprises a chimeric antibody, for example from mouse, rat, horse, pig, or other species, bearing human constant and/or variable region domains.

In some embodiments, a binding agent includes one or more antibody fragments, including, but not limited to Fab', Fab, F(ab')2, single domain antibodies (DABs), Fv, scFv (single chain Fv), polypeptides with antibody CDRs, scaffolding domains that display the CDRs (e.g., anticalins) or nanobodies. For example, a provided antibody may be a VHH (i.e., an antigen-specific VHH) antibody that comprises only a heavy chain. Such antibody molecules can be derived from a llama or other camelid antibody (e.g., a camelid IgG2 or IgG3, or a CDR-displaying frame from such camelid Ig) or from a shark antibody. In some embodiments the binding agent is or comprises an avibody (diabody, tribody, tetrabody). Techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

In some embodiments, provided binding agents include one or more "Mini-antibodies" or "minibodies". Minibodies are sFv polypeptide chains which include oligomerization domains at their C-termini, separated from the sFv by a hinge region. Pack et al. (1992) *Biochem* 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) *J Immunology* 149B: 120-126.

Peptidomimetic

In some embodiments, provided binding agents include one or more antibody-like binding peptidomimetics. Liu et al. *Cell Mol Biol* (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using the such peptides are provided in U.S. Patent Publn. No. 20100317547, incorporated herein by reference.

Scaffold Protein

In some embodiments, provided binding agents include one or more antibody-like binding scaffold proteins. For example, in some embodiments, one or more CDRs arising from an antibody may be grafted onto a protein scaffold. In general, protein scaffolds may meet the greatest number of the following criteria: (Skerra A., *J. Mol. Recogn.*, 2000, 13:167-187): good phylogenetic conservation; known three-dimensional structure (as, for example, by crystallography, NMR spectroscopy or any other technique known to a person skilled in the art); small size; few or no post-transcriptional modifications; and/or easy to produce, express and purify. The origin of such protein scaffolds can be, but is not limited to, fibronectin (e.g., fibronectin type III domain 10), lipocalin, anticalin (Skerra A., *J. Biotechnol.*, 2001, 74(4):257-75), protein Z arising from domain B of protein A of *Staphylococcus aureus*, thioredoxin A or proteins with a repeated motif such as the "ankyrin repeat" (Kohl et al., *PNAS,* 2003, vol. 100, No. 4, 1700-1705), the "armadillo repeat", the "leucine-rich repeat" and the "tetratricopeptide repeat". For example, anticalins or lipocalin derivatives are described in US Patent Publication Nos. 20100285564, 20060058510, 20060088908, 20050106660, and PCT Publication No. WO2006/056464, incorporated herein by reference. Scaffolds derived from toxins such as, for example, toxins from scorpions, insects, plants, mollusks, etc., and the protein inhibitors of neuronal NO synthase (PIN) may also be used in accordance with the present invention.

Mimotope

In some embodiments, provided binding agents include a mimotope, which can be used to disrupt the interaction between an influenza virus and the HA polypeptide receptor. In some embodiment, the mimotope is used to elicit an antibody response identical or similar to the that elicited by its corresponding target epitope. In some embodiments, the target epitope is a sequence that is conserved across more than one influenza subtype. In some embodiment, the conserved epitope is a sequence that is conserved across influenza types 1 and 2. For example, an HA sequences from all influenza subtypes located within the HA-1 (head) and HA-2 (stalk) domains. In some embodiments, the epitope is a conserved sequence located within the HA-1/HA-2 interface membrane proximal epitope region (MPER). In some embodiments, the epitope is a conserved sequence located within the canonical α-helix and/or residues in its vicinity. In some embodiments, a mimotope is a peptide. In some embodiments, a mimotope is a small molecule, carbohydrate, lipid, or nucleic acid. In some embodiments, mimotopes are peptide or non-peptide mimotopes of conserved influenza epitopes. In some embodiments, by mimicking the structure of a defined viral epitope, a mimotope interferes with the ability of influenza virus particles to bind to its natural binding partners, e.g., by binding to the natural binding partner itself.

Stapled Peptide

In some embodiments, the provided binding agent is a stapled peptide. In some embodiments, the stapled peptide comprises an amino acid sequences encoding one or more CDRs and/or FRs comprising at least greater than 65, 70, 75, 80, 85, 86, 87, 88, 89, 90, 91, 92, 93, 94, 95, 96, 97, 98 or 99% homology and/or identity with the corresponding CDRs and/or FRs of anti-HA antibodies from Tables 2 and 3 as discussed below. In some embodiments, the stapled peptide comprises an amino acid sequence encoding one or more VH and/or VL chain sequence comprising at least greater than 65, 70, 75, 80, 85, 86, 87, 88, 89, 90, 91, 92, 93, 94, 95, 96, 97, 98 or 99% homology and/or identity with the corresponding VH and VL chains of anti-HA antibodies from Tables 2 and 3 as discussed below.

Nucleic Acid

In certain embodiments, a binding agent is or comprise a nucleic acid, such as DNA or RNA. In certain embodiments, nucleic acids can be DNA or RNA, and can be single stranded or double-stranded. In some embodiments, nucleic acids may include one or more non-natural nucleotides; In some embodiments, nucleic acids include only natural nucleotides. In some embodiments the nucleic acid is designed to mimic an epitope within a hemagglutinin (HA) polypeptide. In some embodiments the nucleic acid is designed to mimic a conserved epitope within one or more Influenza HA polypeptide subtypes. In some embodiments, a provided binding agent is or comprises one or more oligonucleotides. In some embodiments, a provided binding agent is or comprises one or more oligonucleotides comprising a secondary structure such as loop, hairpin, fold or combinations thereof. In some embodiments, a provided binding agent is or comprises one or more oligonuclotides comprising a higher ordered (tertiary or quaternary) structure. In some embodiments, a provided binding agent is or comprises an aptamer.

Targeted Binding

In some embodiments a binding agent is or comprises an agent that binds to a selected binding site. In some embodiments, such a binding agent is an engineered or designed polypeptide. In some embodiments, such a selected binding site is within a hemagglutinin (HA) polypeptide. In some embodiments, such a selected binding site is within the MPER region of an HA polypeptide. In some embodiments, such a selected binding agent is capable of binding to a selected binding site within an HA polypeptide MPER region independent of its glycosylation. For example, in some embodiments, binding agents are designed to be of appropriate size that their binding to an MPER region is not prevented by its glycosylation. In some embodiments, a binding agent binds to a glycosylated MPER region with an affinity that is at least 5%, 10%, 15%, 20%, 25%, 30%, 35%, 40%, 45%, 50%, 55%, 60%, 65%, 70%, 75%, 80%, 85%, 90% or more of its affinity for an otherwise identical non-glycosylated MPER region. In some embodiments, the binding agents bind to an HA polypeptide sequence located within the HA-1 (head) and/or HA-2 (stalk) domains. In some embodiments, the binding agents bind to an HA polypeptide sequence located within the HA-1/HA-2 interface membrane proximal epitope region (MPER). In some embodiment, the binding agents bind to an HA polypeptide sequence located within the canonical α-helix and/or residues in its vicinity.

In some embodiments, binding agents bind to their selected binding sites by interaction with one or more target residues. In some embodiments, such target residues are amino acids, saccharides, lipids or combinations thereof. In some embodiments the present invention provides binding agents that bind to an HA polypeptide, N-linked glycans on an HA polypeptide, an HA receptor, sialylated glycans on an HA receptor or various combinations thereof. In some embodiments, a binding agent that binds to an HA receptor interacts with one or more glycans on the HA receptor. In some embodiments, binding agents bind sialylated glycans. In some embodiments, binding agents compete with influenza virus for binding to HA receptors. In some embodiments, binding agents compete with influenza virus for binding such that binding between the influenza virus and the HA receptor is reduced at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold. In some embodiments, binding agents compete with influenza virus for binding to glycans on HA receptors.

In many embodiments, binding agents have a length that is less than about 1000 amino acids. In some embodiments, binding agents have a length that is less than a maximum length of about 1000, 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 240, 230, 220, 210, 200, 190, 180, 170, 160, 150, 140, 130, 125, 120, 115, 110, 105, 100, 95, 90, 85, 80, 75, 70, 65, 60, 55, 50, 45, 40, 35, 30, 25, or 20 amino acids in length. In some embodiments, binding agents have a length that is greater than a minimum length of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or more amino acids in length. In some embodiments, binding agents have a length between any one of such minimum lengths and any one of such maximum lengths, so long as the maximum length is longer than the minimum length. In some particular embodiments, a binding agent has a length between about 20 and 500, or between 30 and 400, or between 40 and 300, or between 80 and 250 amino acids. In some embodiments, a binding agent has a length of about 84, 88, 93, 95, 98, 104, 106, 110, 111, 116, 119, 123, 124, 132, 212, 215, 244, or 245.

Binding Agent Modification

In some embodiments, binding agents are comprised of natural amino acids. In other embodiments, binding agents comprise one or more unnatural amino acids. In some embodiments, binding agents are comprised of combinations of natural and unnatural amino acids. In some embodiments, a binding agent is comprised of one, two or more polypeptide chains that are covalently or non-covalently associated. In some embodiments, a binding agent may be linked to, or part of, a longer polypeptide chain, so long as the binding agent retains its three-dimensional structure and arrangement for interaction. In some embodiments, binding agents may be appended to the N- or C-termini of another polypeptide sequence that is or is not a binding agent. In some embodiments, binding agents are incorporated into the sequence of another polypeptide that is or is not a binding agent, thereby separating the polypeptide sequence into two or more segments.

In some embodiments, appending the binding agent to the N or C termini or within the sequence of another polypeptide that is or is not a binding may allow for at least one or more of the following: a decrease in immunogenicity, increased circulation lifetime, slower in vivo degradation, inciting local immune response, interaction with the immune system molecules, an increase in volume, an increase in affinity for the binding agent target(s), an increase in specificity for the binding target(s), or the use of other commonly used therapeutic/prophylactic delivery protocols. In some embodiments, appending a binding agent to the N or C termini or within the sequence of another polypeptide that is or is not a binding agent does not have a direct effect on binding of a binding agent to a target (e.g., an HA polypeptide, the MPER region of an HA polypeptide, N-glycans on an HA polypeptide, HA receptors or sialylated glycans on HA receptors).

Binding Agent Conjugates

In some embodiments, a provided binding agent is or comprises a conjugate, in which a binding agent moiety (comprises or consists of the binding agent or a functional portion thereof) with a conjugated moiety. In some particular embodiments, binding agents as described herein are provided and/or utilized in association with one or more active agents or "payloads", such as a therapeutic or detection agent. In some such embodiments, association between the binding agent and the active agent and/or payload comprises at least one covalent interaction so that a binding-agent conjugate is provided.

In some embodiments, a therapeutic payload agent is an effector entity having a desired activity, e.g., anti-viral activity, anti-inflammatory activity, cytotoxic activity, etc. Therapeutic agents can be or comprise any class of chemical entity including, for example, proteins, carbohydrates, lipids, nucleic acids, small organic molecules, non-biological polymers, metals, ions, radioisotopes, etc. In some embodiments, therapeutic agents for use in accordance with the present invention may have a biological activity relevant to the treatment of one or more symptoms or causes of influenza infection (e.g., for example, anti-viral, pain-relief, anti-inflammatory, immunomodulatory, sleep-inducing activities, etc). In some embodiments, therapeutic agents for use in accordance with the present invention have one or more other activities.

In some embodiments, a payload detection agent is or comprises any moiety which may be detected using an assay, for example due to its specific functional properties and/or chemical characteristics. Non-limiting examples of such agents include enzymes, radiolabel s, haptens, fluorescent labels, phosphorescent molecules, chemiluminescent molecules, chromophores, luminescent molecules, photoaffinity molecules, colored particles or ligands, such as biotin.

Many appropriate payload detection agents are known in the art, as are systems for their attachment to binding agents (see, for e.g., U.S. Pat. Nos. 5,021,236; 4,938,948; and 4,472,509, each incorporated herein by reference).

Exemples of such payload detection agents include paramagnetic ions, radioactive isotopes, fluorochromes, NMR-detectable substances, X-ray imaging agents, among others. For exaple, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

In some embodiments, a radioactive isotope is one or more of astatine211, 14carbon, 51chromium, 36chlorine, 57cobalt, 58cobalt, copper67, 152Eu, gallium67, 3hydrogen, iodine123, iodine125, iodine131, indium111, 59iron, 32phosphorus, radium223, rhenium186, rhenium188, 75selenium, 35sulphur, technicium99m, thorium227 and/or yttrium90. Radioactively labeled antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Provided binding agents may be labeled with technetium99m by ligand exchange process, for example, by reducing pertechnate with stannous solution, chelating the reduced technetium onto a Sephadex column and applying the antibody to this column. In some embodiments, provided binding agent are labeled using direct labeling techniques, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

In some embodiments, a fluorescent label is or comprises one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Several methods are known in the art for the attachment or conjugation of a binding agent to a payload. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Provided binding agents may also be reacted with an enzyme in the presence of a coupling agent such as glutaraldehyde or periodate. Conjugates with fluorescein markers are prepared in the presence of these coupling agents or by reaction with an isothiocyanate.

Production of Anti-Influenza Antibodies

Provided antibodies, and/or characteristic portions thereof, or nucleic acids encoding them, may be produced by any available means. Methods for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

Provided antibodies (or characteristic portions) may be produced, for example, by utilizing a host cell system engineered to express an inventive antibody-encoding nucleic acid. Alternatively or additionally, provided antibodies may be partially or fully prepared by chemical synthesis (e.g., using an automated peptide synthesizer).

Exemplary sources for antibody preparations suitable for the invention include, but are not limited to, conditioned culture medium derived from culturing a recombinant cell line that expresses a protein of interest, or from a cell extract of, e.g., antibody-producing cells, bacteria, fungal cells, insect cells, transgenic plants or plant cells, transgenic animals or animal cells, or serum of animals, ascites fluid, hybridoma or myeloma supernatants. Suitable bacterial cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Suitable fungal host cells that can be used include, but are not limited to, *Saccharomyces cerevisiae, Pichia pastoris* and *Aspergillus* cells. Suitable insect cells include, but are not limited to, S2 Schneider cells, D. Mel-2 cells, SF9, SF21, High-5™, Mimic™-SF9, MG1 and KC1 cells. Suitable exemplary recombinant cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TRI cells, MRC 5 cells, FS4 cells, and human hepatoma line (Hep G2).

Antibodies of interest can be expressed using various vectors (e.g., viral vectors) known in the art and cells can be cultured under various conditions known in the art (e.g., fed-batch). Various methods of genetically engineering cells to produce antibodies are well known in the art. See e.g. Ausabel et al., eds. (1990), Current Protocols in Molecular Biology (Wiley, N.Y.).

Provided antibodies may be purified, if desired, using filtration, centrifugation and/or various chromatographic methods such as HPLC or affinity chromatography. In some embodiments, fragments of provided antibodies are obtained by methods which include digestion with enzymes, such as pepsin or papain, and/or by cleavage of disulfide bonds by chemical reduction.

Also, it will be appreciated by those of ordinary skill in the art that polypeptides, and particularly antibodies as described herein, may be generated, identified, isolated, and/or produced by culturing cells or organisms that produce antibodies (whether alone or as part of a complex, including as part of a virus particle or virus), under conditions that allow ready screening and/or selection of polypeptides capable of binding to influenza antigens (e.g., influenza HA). To give but one example, in some embodiments, it may be useful to produce and/or study a collection of antibodies under conditions that reveal and/or favor those variants that bind to HA polypeptides (e.g., with particular specificity and/or affinity). In some embodiments, such a collection of antibodies results from evolution in nature. In some embodiments, such a collection of antibodies results from engineering. In some embodiments, such a collection of antibodies results from a combination of engineering and natural evolution.

It will be appreciated that provided antibodies may be engineered, produced, and/or purified in such a way as to improve characteristics and/or activity of the antibody. For example, improved characteristics of provided antibodies include, but are not limited to, increased stability, improved binding affinity and/or avidity, increased binding specificity, increased production, decreased aggregation, decreased nonspecific binding, among others.

Nucleic Acids

In certain embodiments, the present invention provides nucleic acids which encode an antibody or a characteristic or biologically active portion of an antibody. In some embodiments, the invention provides nucleic acids which are complementary to nucleic acids which encode an antibody or a characteristic or biologically active portion of an antibody.

In some embodiments, the invention provides nucleic acid molecules which hybridize to nucleic acids encoding an antibody or a characteristic or biologically active portion of an antibody. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In certain embodiments, nucleic acids can be DNA or RNA, and can be single stranded or double-stranded. In some embodiments, nucleic acids may include one or more non-natural nucleotides; In some embodiments, nucleic acids include only natural nucleotides.

Systems for Identifying and/or Characterizing Binding Agents

The present invention provides a variety of systems for testing, characterizing, and/or identifying influenza binding agents (e.g., anti-HA antibodies). In some embodiments, provided binding agents are used to identify and/or to characterize other influenza agents (e.g., antibodies, polypeptides, small molecules, etc.).

In some embodiments, provided binding agents are characterized by such systems and methods that involve contacting the binding agent with one or more candidate substrates, such as regions of HA polypeptides, N-glycans on HA polypeptides, HA receptors, sialylated HA receptors, glycans on sialylated HA receptors and/or umbrella topology glycans on sialylated HA receptors.

In some embodiments, an agent and/or candidate substrate may be free in solution, fixed to a support, and/or expressed in and/or on the surface of a cell. The candidate substrate and/or agents may be labeled, thereby permitting detection of binding. Either the agent or the candidate substrate is the labeled species. Competitive binding formats may be performed in which one of the substances is labeled, and one may measure the amount of free label versus bound label to determine the effect on binding.

In some embodiments, binding assays involve, for example, exposing a candidate substrate to an agent and detecting binding between the candidate substrate and the agent. A binding assay may be conducted in vitro (e.g., in a candidate tube, comprising substantially only the components mentioned; in cell-free extracts; and/or in substantially purified components). Alternatively or additionally, binding assays may be conducted in cyto and/or in vivo (e.g., within a cell, tissue, organ, and/or organism; described in further detail below).

In certain embodiments, at least one agent is contacted with at least one candidate substrate and an effect detected. In some embodiments, for example, an agent is contacted with a candidate substrate, and binding between the two entities is monitored. In some embodiments, an assay may involve contacting a candidate substrate with a characteristic portion of an agent. Binding of the agent to the candidate substrate is detected. It will be appreciated that fragments, portions, homologs, variants, and/or derivatives of agents may be employed, provided that they comprise the ability to bind one or more candidate substrates.

Binding of an agent to the candidate substrate may be determined by a variety of methods well-known in the art. The present invention provides assays involving solid phase-bound agents and detecting their interactions with one or more candidate substrates. Thus, an agent may comprise a detectable marker, such as a radioactive, fluorescent, and/or luminescent label. Furthermore, candidate substrate can be coupled to substances which permit indirect detection (e.g. by means of employing an enzyme which uses a chromogenic substrate and/or by means of binding a detectable antibody). Changes in the conformation of agents as the result of an interaction with a candidate substrate may be detected, for example, by the change in the emission of the detectable marker. Alternatively or additionally, solid phase-bound protein complexes may be analyzed by means of mass spectrometry.

In some embodiments, the agent can be non-immobilized. In some embodiments, the non-immobilized component may be labeled (with for example, a radioactive label, an epitope tag, an enzyme-antibody conjugate, etc.). Alternatively or additionally, binding may be determined by immunological detection techniques. For example, the reaction mixture may be subjected to Western blotting and the blot probed with an antibody that detects the non-immobilized component. Alternatively or additionally, enzyme linked immunosorbent assay (ELISA) may be utilized to assay for binding.

In certain embodiments, cells may be directly assayed for binding between agents and candidate substrates. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of in cyto assays for measuring the ability of agents to bind to candidate substrates.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

In some embodiments, a binding assays described herein may be performed using a range of concentrations of agents and/or candidate substrates. In some embodiments, the binding assays described herein are used to assess the ability of a candidate substrate to bind to an agent over range of antibody concentrations (e.g. greater than about 100 µg/ml, about 100 µg/ml, about 50 µg/ml, about 40 µg/ml, about 30 µg/ml, about 20 µg/ml, about 10 µg/ml, about 5 µg/ml, about 4 µg/ml, about 3 µg/ml, about 2 µg/ml, about 1.75 µg/ml, about 1.5 µg/ml, about 1.25 µg/ml, about 1.0 µg/ml, about 0.9 µg/ml, about 0.8 µg/ml, about 0.7 µg/ml, about 0.6 µg/ml, about 0.5 µg/ml, about 0.4 µg/ml, about 0.3 µg/ml, about 0.2 µg/ml, about 0.1 µg/ml, about 0.05 µg/ml, about 0.01 µg/ml, and/or less than about 0.01 µg/ml).

In some embodiments, any of the binding studies described herein can be executed in a high throughput fashion. Using high throughput assays, it is possible to screen up to several thousand agents in a single day. In some embodiments, each well of a microtiter plate can be used to run a separate assay against a selected candidate substrate, or, if concentration and/or incubation time effects are to be observed, every 5-10 wells can test a single candidate substrate. Thus, a single standard microtiter plate can assay up to 96 binding interactions between agents and candidate substrates; if 1536 well plates are used, then a single plate can assay up to 1536 binding interactions between agents and candidate substrates; and so forth. It is possible to assay many plates per day. For example, up to about 6,000, about 20,000, about 50,000, or more than about 100,000 assay screens can be performed on binding interactions between antibodies and candidate substrates using high throughput systems in accordance with the present invention.

In some embodiments, such methods utilize an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naive to viral exposure or infection prior to administration of an agent (optionally in an inventive composition). In some embodiments, the animal host is inoculated with, infected with, or otherwise exposed to virus prior to or concurrent with administration of an agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or α2,6 glycans vs. α 2,3 glycans to the distribution found in the human respiratory tract. For example, it is contemplated that a ferret as an animal host may be more representative than a mouse when used as model of disease caused by influenza viruses in humans (Tumpey, et al. Science (2007) 315; 655-659). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naive animals is known in the art (Tumpey, et al. Science (2007) 315; 655-659). Virus transmission studies may be used to test agents. For example, agents may be administered to a suitable animal host before, during or after virus transmission studies in order to determine the efficacy of said agent in blocking virus binding and/or infectivity in the animal host. Using information gathered from virus transmission studies in an animal host, one may predict the efficacy of an agent in blocking virus binding and/or infectivity in a human host.

Pharmaceutical Compositions

The present invention provides compositions comprising one or more provided binding agents. In some embodiments the present invention provides at least one binding agent and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of influenza infection or of negative ramifications and/or symptoms associated or correlated with influenza infection. In some embodiments, provided pharmaceutical compositions are useful in therapeutic applications, for example in individuals suffering from or susceptible to influenza infection. In some embodiments, pharmaceutical compositions are formulated for administration to humans.

For example, pharmaceutical compositions provided here may be provided in a sterile injectible form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Vaccines

In some embodiments, the present invention provides vaccine compositions for use, and/or for exam in passive immunization (i.e., immunization wherein a binding agent is administered to a subject) of a subject who is suffering from or susceptible to influenza infection. In some embodiments, passive immunization occurs when antibodies are transferred from mother to fetus during pregnancy. In some embodiments, passive immunization includes administration of antibodies directly to an individual (e.g., by injection, orally, nasally, etc.).

In some embodiments, prophylactic applications may include administering vaccines. In some embodiments, vaccination is tailored to the individual patient. For example, as described below, serum may be collected from a patient and tested for presence of influenza, and in some embodiments for one or more particular influenza subtypes. In some embodiments, appropriate recipients of provided vaccines are individuals suffering from or susceptible to infection with one or more influenza subtypes bound and/or neutralized by a provided antibody.

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on their website. See also Allison (1998, Dev. Biol. Stand., 92:3-11; incorporated herein by reference), Unkeless et al. (1998, Annu. Rev. Immunol., 6:251-281; incorporated herein by reference), and Phillips et al. (1992, Vaccine, 10:151-158; incorporated herein by reference). Hundreds of different adjuvants are known in the art and could be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, E. coli heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc. Pharmaceutically acceptable excipients have been previously described in further detail in the above section entitled "Pharmaceutical Compositions."

Combination Therapy

Pharmaceutical compositions of the present invention may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans.

In some embodiments, pharmaceutical compositions of the present invention may be administered in combination with one or more other agents. In some embodiments pharmaceutical compositions of the present invention may be administered in combination with one or more other pharmaceutical agents (e.g., anti-influenza vaccine, anti-viral agent, pain relievers, anti-inflammatories, antibiotics, steroidal agents, antibodies, sialydase, etc). In some embodiments, pharmaceutical compositions of the present invention and/or agents (e.g., antibodies) may be administered in combination with an adjuvant.

In some embodiments, pharmaceutical compositions of the present invention are administered in combination with one or more anti-viral agents. In some embodiments, such anti-viral agents include, but are not limited to, acyclovir, ribavirin, amantadine, remantidine, zanamivir (Relenza), oseltamivir (Tamiflu), amantadine, rimantadine and/or combinations thereof.

In some embodiments, pharmaceutical compositions of the present invention are administered in combination one or more vaccines. In some embodiments, the vaccine is a anti-viral vaccine. In some embodiments, the vaccine is an anti-influenza vaccine. In some embodiments, the anti-influenza vaccine is to treat seasonal influenza (e.g., commonly referred to as the "flu"). In some embodiments, the anti-influenza vaccine is the flu shot and/or FluMist. In some embodiments, the anti-influenza vaccine is targeted to a specific combination of one or more HA polypeptides (e.g., H1, H2, H3, H4, H5, H6, H7, H8, H9, H10, H11, H12, H13, H14, H15, or H16 polypeptides). In some embodiments, the anti-influenza vaccine is specific for one or more combinations of H1N1, H2N2, H3N2, H5N1, H7N7, H1N2, H9N2, H7N2, H7N3, or H10N7 viruses. In some embodiments, the anti-influenza vaccine is specific to H1N1 viruses. In some embodiments, the anti-influenza vaccine is specific to H3N2 viruses. In some embodiments, the anti-influenza vaccine is specific to H1N1 and H3N2 viruses.

In some embodiments pharmaceutical compositions may be administered in combination with one or more other pharmaceutical agents used to treat the symptoms associated with influenza virus infection. In some embodiments, pharmaceutical agents used to treat the symptoms associated with influenza infection are pain relievers, anti-inflammatories, antibiotics and/or combinations thereof. In some embodiments, pharmaceutical agents used to treat the inflammation symptoms associated with influenza infection is selected from the group consisting of NSAID, Steroid, Glucocorticoid, and/or combinations thereof. In some embodiments, NSAID pharmaceutical agents used to treat the influenza symptoms associated with influenza infection is selected from the group consisting of acetaminophen, ibuprofen, aspirin, naproxen and/or combinations thereof.

Methods of Administration

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc.

At present the oral or nasal spray or aerosol route (e.g., by inhalation) is most commonly used to deliver therapeutic agents directly to the lungs and respiratory system. However, the invention encompasses the delivery of the inventive pharmaceutical composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, inventive compositions are administered as drops to the nasal or buccal cavity. In some embodiments, a dose may comprise a plurality of drops (e.g., 1-100, 1-50, 1-20, 1-10, 1-5, etc.)

In some embodiments, inventive compositions are administered using a device that delivers a metered dosage of composition.

Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662. Intradermal compositions may also be administered by devices which limit the effective penetration length of a needle into the skin, such as those described in WO99/34850, incorporated herein by reference, and functional equivalents thereof. Also suitable are jet injection devices which deliver liquid compositions to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Also suitable are ballistic powder/particle delivery devices which use compressed gas to accelerate compositions in powder form through the outer layers of the skin to the dermis. Additionally, conventional syringes may be used in the classical mantoux method of intradermal administration.

Diagnostics Applications

In some embodiments, influenza binding agents in accordance with the invention are used for diagnostic applications. For example, by virtue of the variety of binding profiles of binding agents, diagnostic assays may be employed which will detect a plurality of influenza genotypes and/or subtypes, so as to provide a pan-influenza binding agent (i.e., a pan-influenza antibody), while at the same time being able to dissect individual genotypes and/or subtypes by subtractive analysis.

For diagnostic purposes, binding agents may be used in a wide variety of formats for detecting HA protein, discerning influenza genotypes and/or subtypes, detecting virions and antibodies. For diagnostic purposes, a wide variety of labels may be employed, which for the most part have been mentioned previously. These include, but are not limited to, fluorophores, chemiluminescent moieties, radioisotopes, enzymes, particles (e.g., colloidal carbon particles, gold particles, latex particles, etc.) ligands for which there are high affinity receptors, and prolabels, which can be activated to provide a detectable signal.

In some embodiments, a surface is coated with a protein, which can bind to influenza antigens as free protein (e.g., circulating proteins) or as part of an intact or partially intact virion. One may use provided binding agents of the invention which bind to multiple influenza genotypes and/or subtypes. In some embodiments, binding agents in accordance with the invention bind to at least one, two, three, four, five, or more than five different genotypes and/or subtypes.

In some embodiments, assays may involve contacting a surface with a medium, which may contain free or influenza-associated protein(s), where the medium may be the sample or a solution of known HA of one or more genotypes and/or subtypes. After incubation and washing to remove non-specifically bound protein, the assay may proceed in various manners depending upon what is being assayed. Where a blood sample suspected of being seropositive is being assayed, the sample may be applied to the layer of HA protein, incubated, and washed, and the presence of human antibodies bound to the protein layer determined. One may use labeled α-human antibodies (other than against the isotype of the subject antibodies, where the subject antibodies have been initially used). In assays for antibodies in seropositive subjects, subject antibodies may be used as controls with the same reagent used to detect any human anti-influenza antibodies in the sera of such subjects. The specificity of the antibodies in the sample can be confirmed by using the subject antibodies, which are differentially labeled from the anti-human antibodies and determine whether they are blocked by the antibodies in the sample.

Where the sample is assayed for influenza HA protein, detection employs labeled subject antibodies, the selection depending upon whether one is interested in genotyping or detection of HA protein. After washing away non-specifically bound antibody, the presence of labeled antibodies is determined by detecting the presence of the label in accordance with known techniques. Alternatively or additionally, where the subject antibodies are bound to a surface, a labeled lectin for HA may be employed to detect the presence of HA protein.

Binding agents in accordance with the invention can be used to measure the reactivity of other binding agents, including antibodies in sera, monoclonal antibodies, antibodies expressed as a result of genetic engineering, etc. In some embodiments, intact virions are used. In some embodiments, conformationally conserved envelope proteins are used.

Labeled subject antibodies may be used in assaying for the presence of influenza from biopsy material. Labeled antibody may be incubated with immobilized biopsy material, such as a lung slice, with a solution of one or more of the subject labeled antibodies. After washing away non-specifically bound antibodies, the presence of the antibodies bound to the cells of the biopsied tissue may be detected in accordance with the nature of the label.

In some embodiments, influenza binding agents in accordance with the invention can be used to identify influenza receptors. Those skilled in the art will appreciate the multitude of ways this can be accomplished (Sambrook J., Fritsch E. and Maniatis T. Molecular Cloning: A Laboratory Manual. Cold Spring Harbor Press, Cold Spring Harbor, N.Y., 1989; and Ausubel et al., eds., Current Protocols in Molecular Biology, 1987; both of which are incorporated herein by reference). Typically, protein and peptide receptors can be identified by determining whether a binding agent able to bind HA can inhibit attachment of influenza virions to a cell susceptible to influenza infection. Thus, receptors for influenza HA proteins and peptides can be identified in this manner. A susceptible cell can be incubated in the presence of influenza and anti-influenza HA binding agent, and a cell-binding assay can be utilized to determine whether attachment is decreased in the presence of the binding agent.

Cells expressing putative receptors for influenza and/or libraries of putative receptors for influenza may be screened for their abilities to bind influenza. For example, cells expressing a putative influenza receptor (e.g., a receptor for influenza HA) can be contacted with an influenza protein or peptide in the presence of an antibody for a time and under conditions sufficient to allow binding of the influenza protein or peptide to putative receptor on the surface of the cell. Alternatively or additionally, influenza proteins, peptides, or virions can be pre-incubated with antibody prior to contacting the putative receptor on the cell surface. Binding can be detected by any means known in the art, e.g., flow cytometry etc. (see Ausubel et al. or Sambrook et al., supra). A decrease in binding to the surface of the cell in the presence of antibody compared to binding in the absence of the cell in the absence of the antibody indicates the identification of an influenza receptor.

In some embodiments, methods of identifying influenza receptors (e.g., such as HA receptors) include the use of solid supports, such as beads, columns, and the like. For example, receptors for influenza proteins and peptides (e.g., HA proteins and/or fragments thereof) and/or influenza virions can be identified by attaching an influenza antibody to a solid support and then contacting the antibody with an influenza protein or peptide for a time sufficient for the influenza protein or peptide to bind to the antibody. This provides an influenza protein ligand for putative influenza receptors that can be contacted with the antibody:ligand complex on the solid support for a time and under conditions sufficient to allow binding of a receptor to the influenza protein or peptide. Proteins can be expressed from a library or provided as a cell extract or purified protein preparation from natural or recombinant cells. Once specific binding complexes between the influenza protein peptide are formed, unbound influenza proteins or peptides, e.g., library proteins or peptide that did not bind specifically to the influenza proteins or peptides, are removed, e.g., by standard washing steps. Bound proteins are then eluted and identified, e.g., by gel electrophoresis.

Kits

The invention provides a variety of kits for conveniently and/or effectively carrying out methods in accordance with the present invention. Kits typically comprise one or more influenza binding agents in accordance with the invention. In some embodiments, kits comprise a collection of different influenza binding agents to be used for different purposes (e.g., diagnostics, treatment, and/or prophylaxis). Typically kits will comprise sufficient amounts of influenza binding agents to allow a user to perform multiple administrations to a subject(s) and/or to perform multiple experiments. In some embodiments, kits are supplied with or include one or more influenza antibodies that have been specified by the purchaser.

In certain embodiments, kits for use in accordance with the present invention may include one or more reference samples; instructions (e.g., for processing samples, for performing tests, for interpreting results, for solubilizing influenza binding agents); buffers; and/or other reagents necessary for performing tests. In certain embodiments kits can comprise panels of antibodies. Other components of kits may include cells, cell culture media, tissue, and/or tissue culture media.

Kits may comprise instructions for use. For example, instructions may inform the user of the proper procedure by which to prepare a pharmaceutical composition comprising influenza binding agents and/or the proper procedure for administering pharmaceutical compositions to a subject.

In some embodiments, kits include a number of unit dosages of a pharmaceutical composition comprising influenza binding agents. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as Styrofoam, etc., may be enclosed.

In some embodiments, kits are used in the treatment, diagnosis, and/or prophylaxis of a subject suffering from and/or susceptible to influenza. In some embodiments, inventive kits comprise at least one component of a delivery device, e.g., a syringe, needle, applicator, inhaler, etc. In some such embodiments, the invention provides a kit comprising at least one component of a delivery device, e.g., an inhaler and/or syringe and a dose of an of an agent. In some embodiments, kits comprise (i) at least one influenza binding agent; (ii) a syringe, needle, applicator, inhaler, etc. for administration of the at least one influenza binding agent to a subject; and (iii) instructions for use.

In some embodiments, kits are used in the treatment, diagnosis, and/or prophylaxis of a subject suffering from and/or susceptible to influenza. In some embodiments, such kits comprise (i) at least one influenza binding agent (i.e., a pan-influenza antibody) provided as a lyophilized powder; and (ii) a diluent for reconstituting the lyophilized powder. Such kits may optionally comprise a syringe, needle, applicator, etc. for administration of the at least one influenza binding agent to a subject; and/or instructions for use.

The present invention provides kits containing reagents for the generation of vaccines comprising at least one influenza binding agent. In some embodiments, such kits may include (i) cells expressing influenza binding agents, characteristic portions thereof, and/or biologically active portions thereof; (ii) media for growing the cells; and (iii) columns, resin, buffers, tubes, and other tools useful for antibody purification. In some embodiments, such kits may include (i) plasmids containing nucleotides encoding influenza binding agents, characteristic portions thereof, and/or biologically active portions thereof; (ii) cells capable of being transformed with the plasmids, such as mammalian cell lines, including but not limited to, Vero and MDCK cell lines; (iii) media for growing the cells; (iv) expression plasmids containing no nucleotides encoding influenza binding agents as negative controls; (v) columns, resin, buffers, tubes, and other tools useful for antibody purification; and (vi) instructions for use.

In some embodiments, kits are used to detect the presence of influenza in one or more samples. Such samples may be pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Such samples may be environmental samples, including, but not limited to, soil, water, and flora. Other samples that have not been listed may also be applicable. In some embodiments, such kits comprise (i) at least one influenza binding agent; (ii) a sample known to contain influenza, as a positive control; and (iii) a sample known not to contain influenza, as a negative control; and (iv) instructions for use.

In some embodiments, kits are used to neutralize influenza in one or more samples. Such kits may provide materials needed to treat an influenza-containing sample with at least one influenza binding agent and to test the ability of the treated sample to infect cultured cells relative to untreated sample. Such kits may include (i) at least one influenza binding agent; (ii) cells capable of being cultured and infected with influenza; (iii) binding agent that is incapable of binding to and neutralizing influenza, as a negative control; (iv) a binding agent that is capable of binding to and neutralizing influenza, as a positive control; (v) a sample known not to contain influenza, as a negative control; (vi) a sample known to contain influenza, as a positive control; and (vii) instructions for use.

These and other aspects of the present invention will be further appreciated upon consideration of the following Examples, which are intended to illustrate certain particular embodiments of the invention but are not intended to limit its scope, as defined by the claims.

EXEMPLIFICATION

Example 1

Identification and Characterization of Influenza Antibodies

The present Example describes production and/or testing of various antibodies provided in accordance with the present invention.

Anti-HA monoclonal antibodies were generated and framework (FR) sequences were determined. Table 2 depicts exemplary amino acid sequences of VH domains of anti-HA antibodies. Table 3 depicts exemplary amino acid sequences of VL domains of anti-HA antibodies. Complementarity Determining Regions (CDRs) of each of the heavy and light chains are depicted in bold and listed in CDR1, CDR2, and CDR3 columns in the Tables 2 and 3.

An exemplary antibody was characterized for binding to HA from different subtypes of influenza. Sequences of the exemplary antibody framework and complement determining regions are indicated in Table 4 below. The exemplary antibody binds to both group 1 and group 2 subtypes of HA with differential binding affinity.

TABLE 4

Amino Acid Sequence of VH and VL Chains of Exemplary Antibody

| Framework | Exemplary Amino Acid Sequence (CDR Sequences in bold) | CDR1 | CDR2 | CDR3 |
|---|---|---|---|---|
| VH | EVQLLESGGGLVKPGQSLKLSCAASGFTFTSYGMHWVRQPPGKGLEWVAVISYDGSYKYYADSVQGRFTISRDNSKNTLYLQMNSLRAEDTAVYYCAKDSELRSLLYFEWLSQGYFNPWGAGTTLTVSSASTK (SEQ ID NO: 1) | GFTFTSY (SEQ ID NO: 17) | SYDGSY (SEQ ID NO: 19) | DSELRSLLYFEWLSQGYFNP (SEQ ID NO: 21) |

TABLE 4-continued

Amino Acid Sequence of VH and VL Chains of Exemplary Antibody

| Frame-work | Exemplary Amino Acid Sequence (CDR Sequences in bold) | CDR1 | CDR2 | CDR3 |
|---|---|---|---|---|
| VL | EIVMTQSPDSLAVSLGERATINCKSSQSVTYNYKNYLAWYQQKPGQPPKLLIYWASTRESGVPDRFSGSGSGTDFTLTISSLQAEDVAVYYCQQYYRTPPTFGGGTKLDIKGS (SEQ ID NO: 33) | KSSQSVTYNYKNYLA (SEQ ID NO: 44) | WASTRES (SEQ ID NO: 55) | QQYYRTPPT (SEQ ID NO: 59) |

The exemplary antibody was tested for binding to HA polypeptides in an in vitro binding assay. Maxisorp 96-well plate wells were coated with 0.2 μg an HA polypeptide of different subtypes (H1, H3, H5, H7 and H9) and left overnight at 4° C. The HA polypeptide coated plates were washed thrice with PBS and blocked with 1% BSA in PB ST. Different concentrations of the exemplary antibody along with C179 antibody (control) were added to HA polypeptide coated wells and the plate was incubated at RT for 2 hrs. The plate was washed thrice with PBST and the wells containing agents were incubated with mouse-anti-6× His antibody (1:1000 dilution) for 1 hr at RT. The plates were washed thrice with PBST and all wells were incubated with goat-anti-mouse HRP antibody for 1 hr at RT. Post-incubation the wells were washes with PBST and the bound HRP was measured using TMB substrate. TMB substrate was added to the wells, incubated for 3 minutes, followed by addition of 1 N sulfuric acid. Absorbance was measured at 450 nm.

Figure 2A:
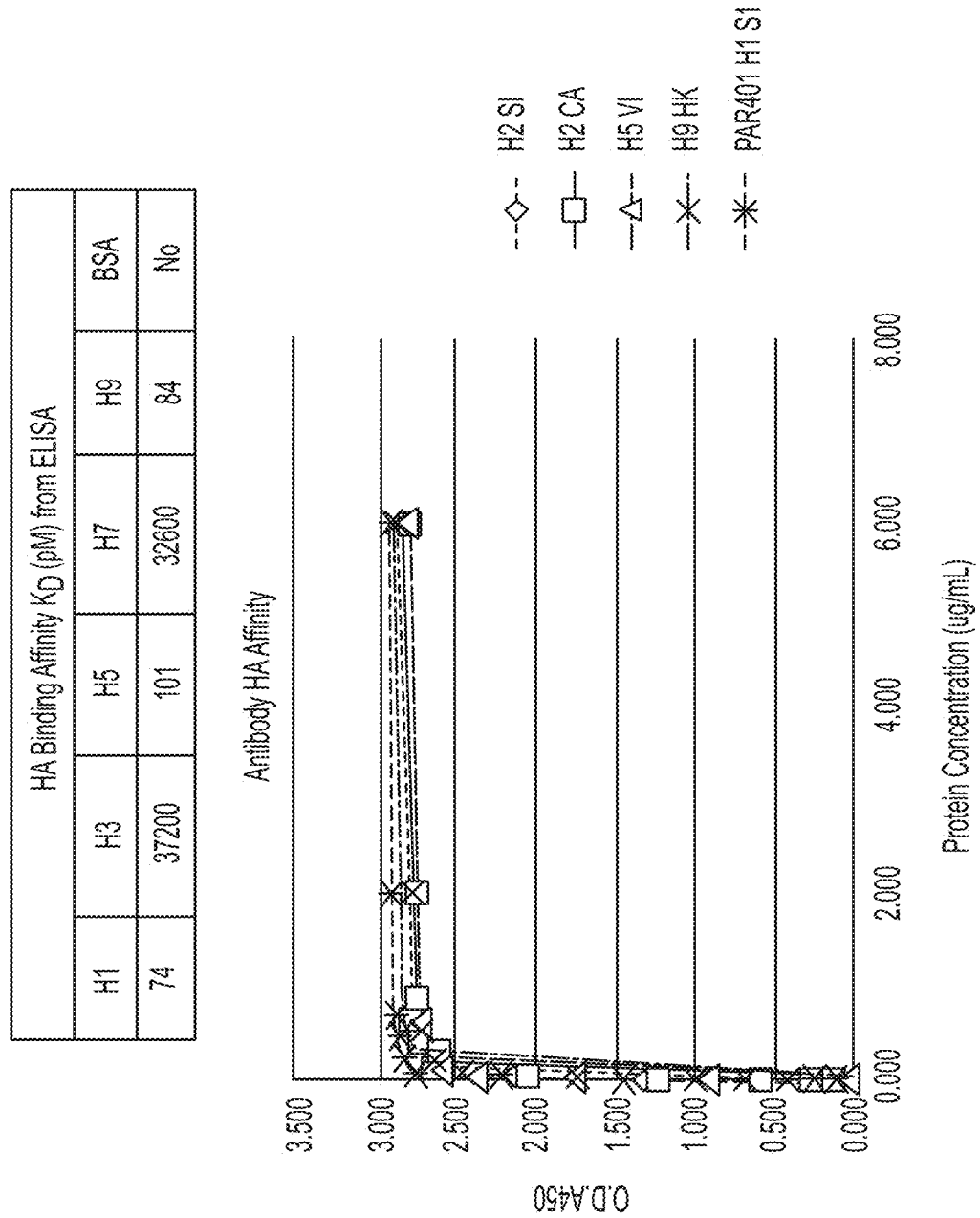
FIGS. 2A and B depicts HA binding affinity for an exemplary antibody.
Figure 2B:
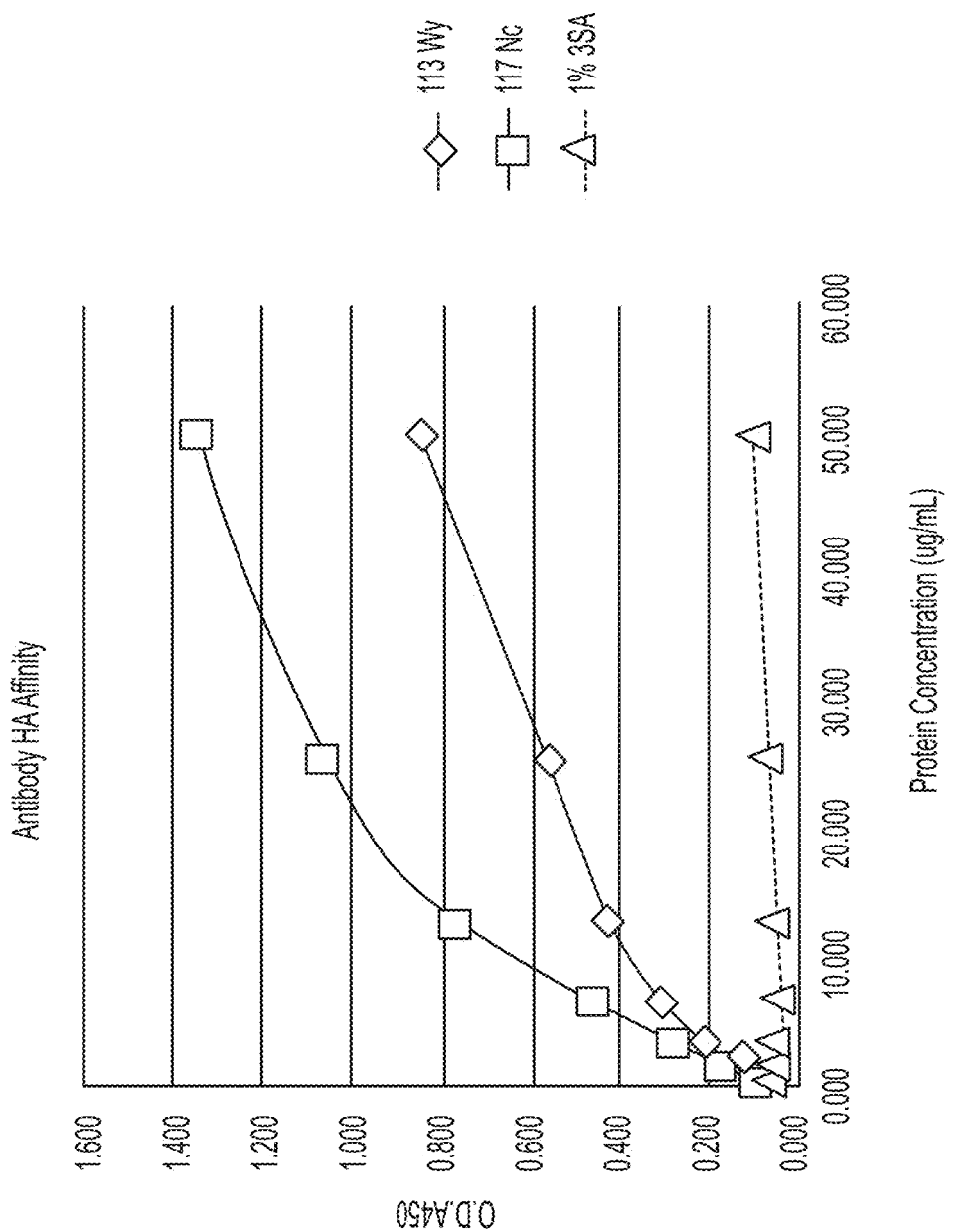
Figure 3A:
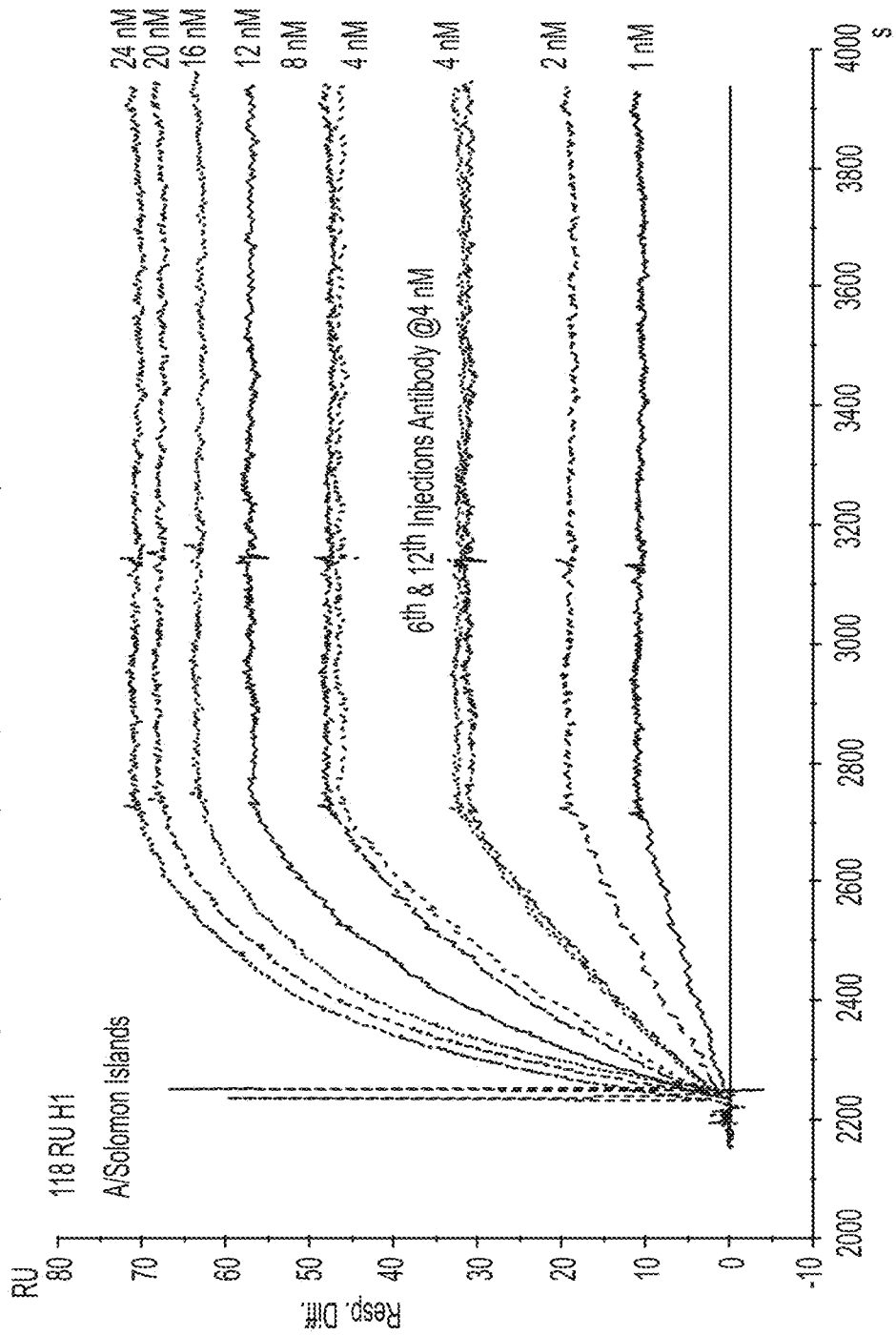
Figure 3B:
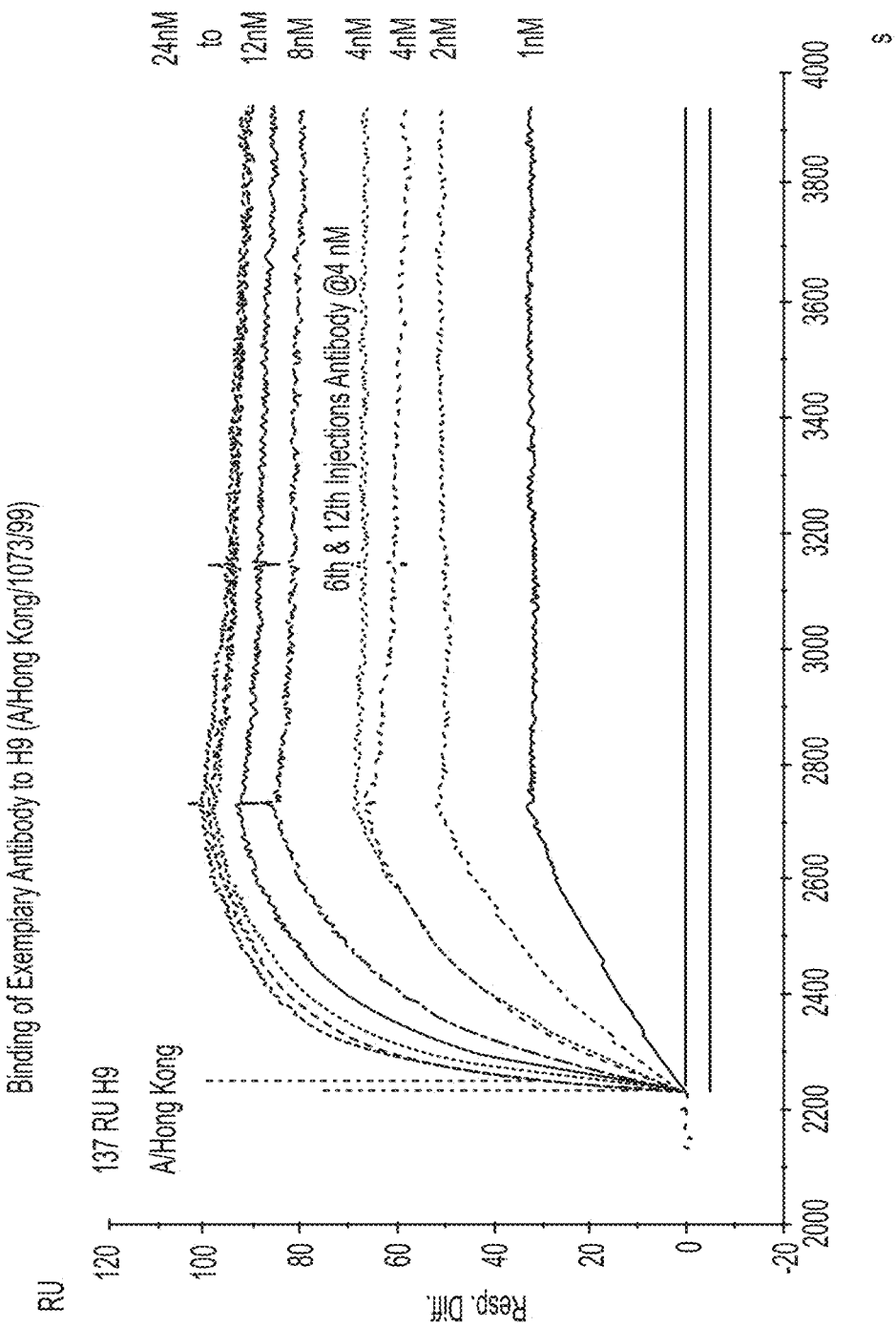
Figure 3D:
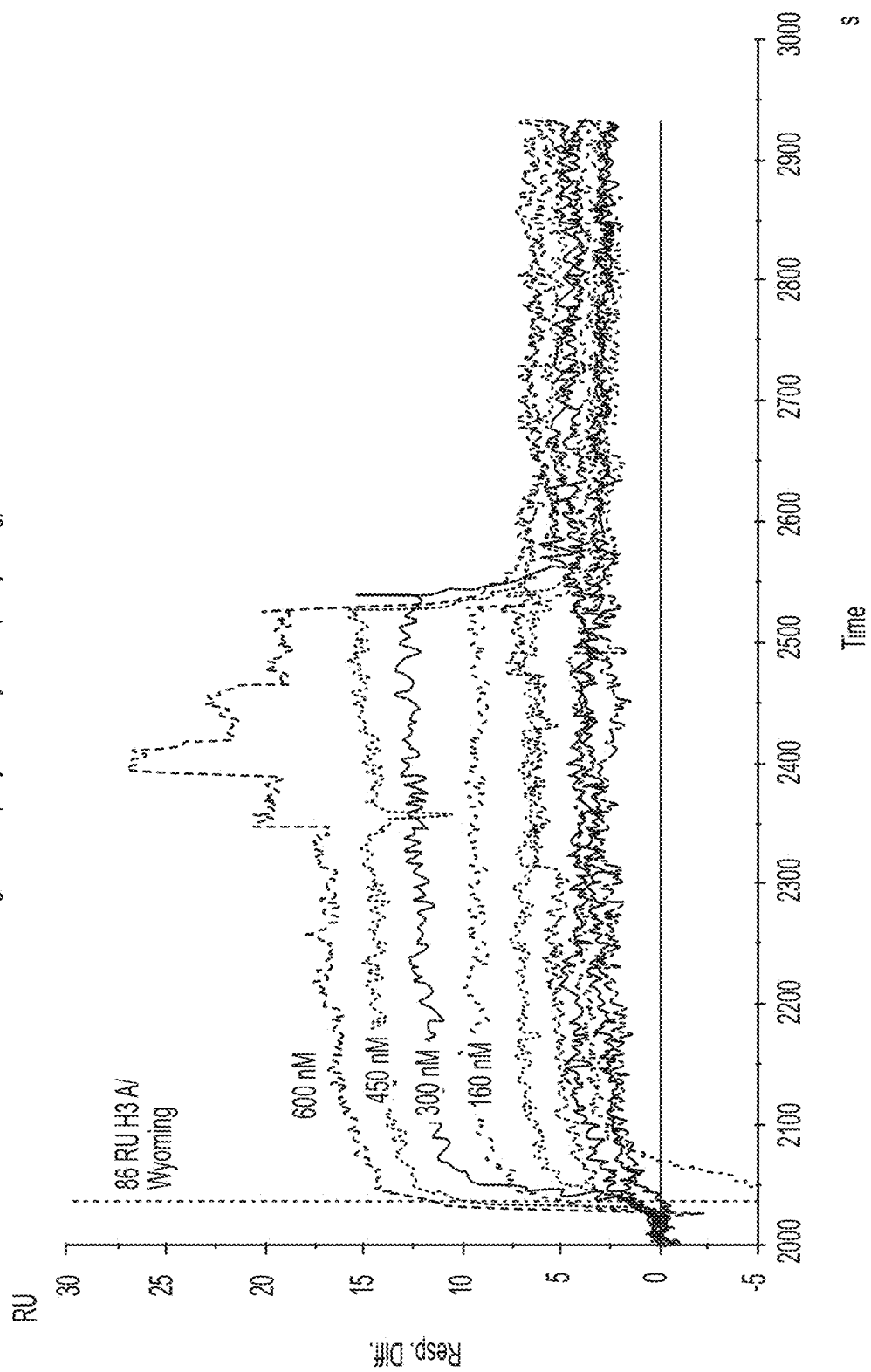
Figure 3E:
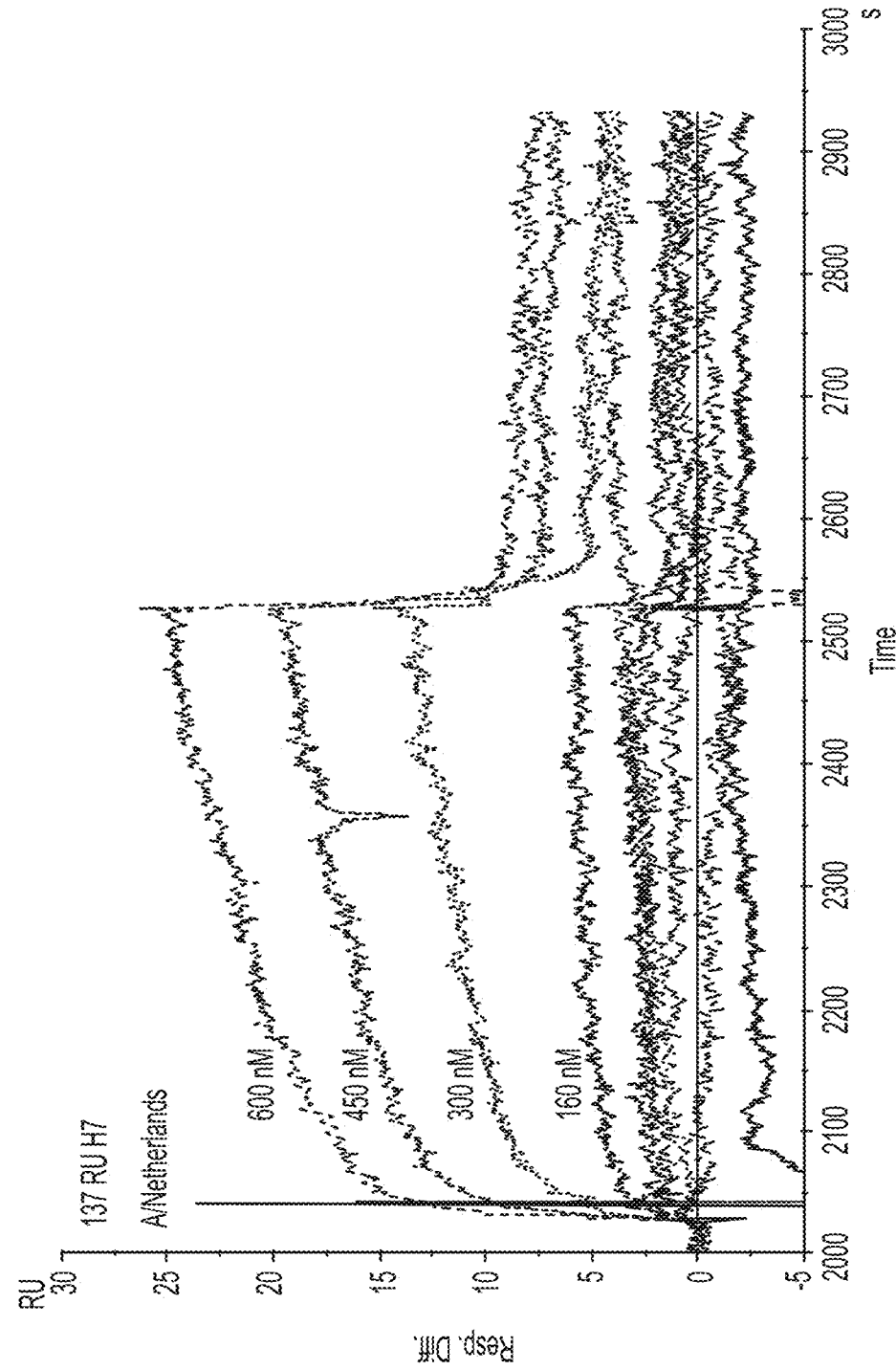
Figure 4:
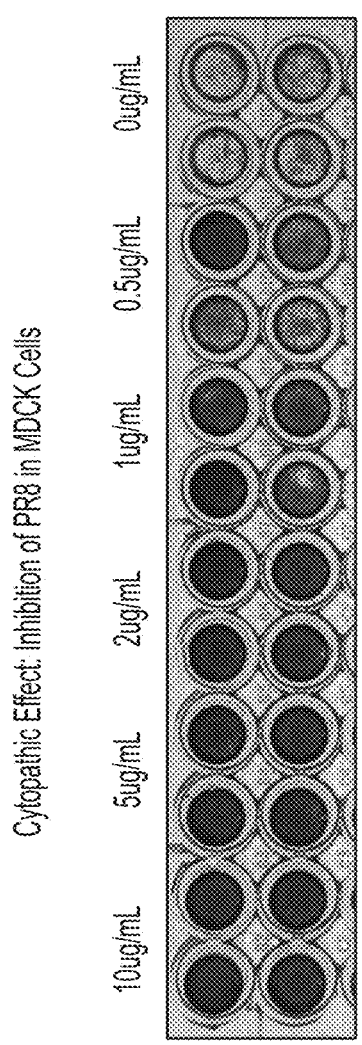
FIG. 4 depicts HA binding affinity and neutralization for an exemplary antibody. The particular antibody inhibits PR8 Virus (H1N1) influenza virus-induced plaque production for 6 different doses.
Figure 5:
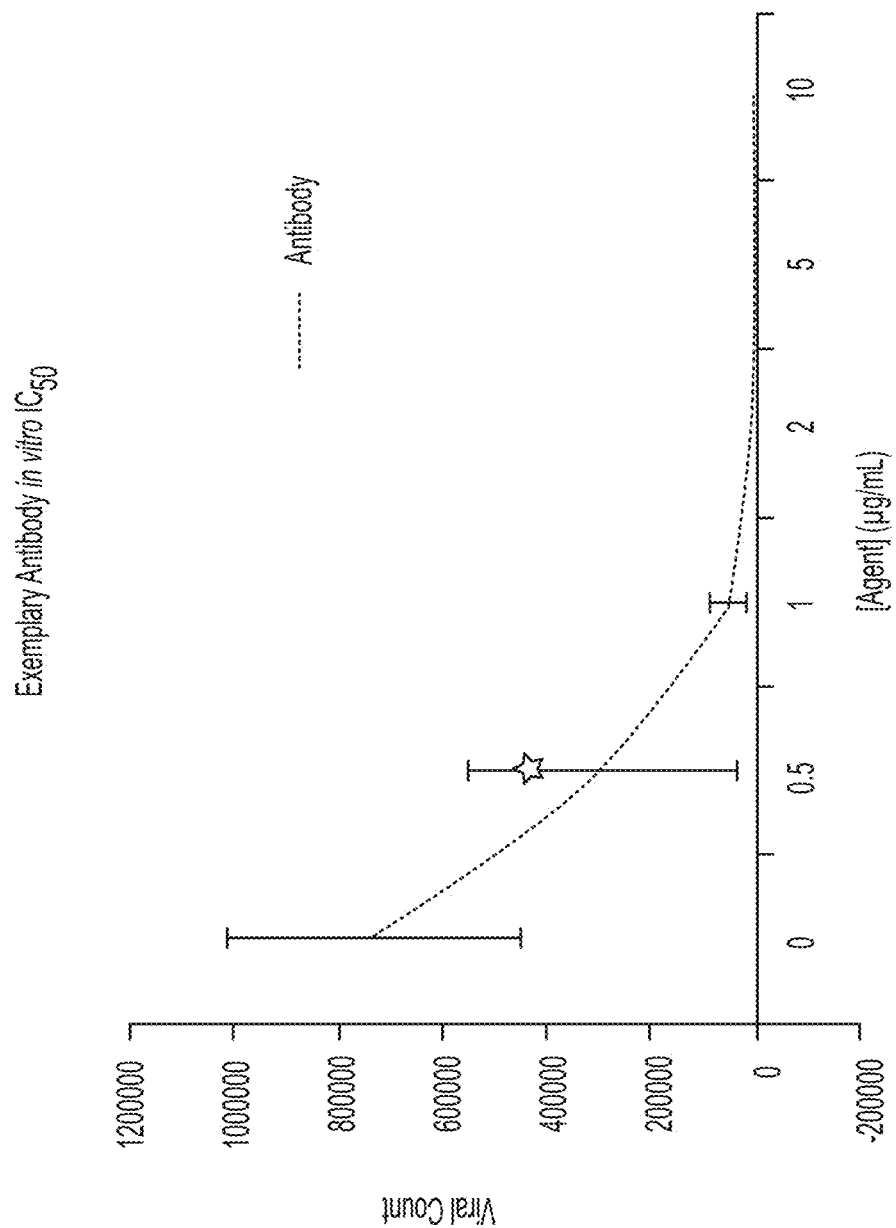
FIG. 5 presents effects of an exemplary antibody pre-incubation with PR8 on infectivity in MDCK cells. After infection, MDCK cells were grown in virus-free media with varying concentration of antibody for 48 hours before viral titer was quantified by real time PCR using primers specific to the virus to calculate an $IC_{50}$ value.

As can be seen in FIG. 2A (bottom panel) and FIG. 2B, our results show that the exemplary antibody binds to various HA polypeptides (H1, H3, H5, H7 and H9).

Example 2

Binding Affinity Between an Exemplary Influenza Antibody and the Targets of the Influenza Antibody The present example shows a calculation of binding affinity, as represented as an equilibrium dissociation constant ($K_D$), between an example influenza antibody and the target of the antibody. In this example, the antibody is an antibody of Example 1 and the targets of the antibody are HA polypeptide from different influenza strains.

Binding affinity between the exemplary antibody and an HA polypeptide is a function of the concentrations of both the antibody and the HA polypeptide. In the present example, the binding affinity is quantitatively described using equilibrium dissociation rate constant ($K_D$). An example of how to measure the dissociation constant is described below.

HA polypeptide coated plates were used to perform ELISA assays with an exemplary antibody as described previously. The measured absorbance at 450 nm was used to calculate the fractional saturation of the receptor. Fractional saturation was plotted as a function of molar concentration of the antibody. Data was fit to the following equation:

$$y = \frac{I_0}{(K_d + I_0)}$$

where y is the fractional saturation, $I_0$ is the concentration of the antibody and $K_D$ is the equilibrium dissociation rate constant.

Using the above referenced calculation, and applying regression analysis, we have observed differential $K_D$ values for HA polypeptides from different Influenza subtypes (FIG. 2A, top panel). In some embodiments, we have observed exemplary antibodies with $K_D$ values in the range of 0.01 to 100 nM for binding of antibodies to different HA polypeptide subtypes. In some embodiments, we have observed exemplary antibodies with $K_D$ values in the range of 0.1 to 500 nM for binding of antibodies to different HA polypeptide subtypes. In some embodiments, we have observed $K_D$ values in the range of 10 to 100 nM for binding of antibodies to HA polypeptides subtypes. In some embodiments, we have observed $K_D$ values in the range of 50 to 100 nM for binding of antibodies to HA polypeptides subtypes.

Example 3

Kinetic Rate Evaluation of an Influenza Antibody

The present example illustrates the ability of an exemplary influenza antibody to reduce virus infectivity in an in vitro binding assays. The present example shows an alternative method for calculating binding affinity, as represented as an association rate constant ($k_a$), dissociation rate constant ($k_d$), and equilibrium dissociation constant $K_D$ between an example influenza antibody and the target of the antibody. In this example, the antibody is an antibody of Example 1 and the targets of the antibody are HA polypeptide from different influenza strains.

Binding affinity between the exemplary antibody and an HA polypeptide is a function of the concentrations of both the antibody and the HA polypeptide. In the present example, binding affinity is quantitatively described using association constant ($k_a$), dissociation constant ($k_d$) and equilibrium constant ($K_D$). An example of how to measure and calculate these constants is described below.

In the experiment, a Biacore™ systems was used to monitor the kinetic rate interaction between the exemplary antibody and various HA polypeptides in real time. The Biacore system works on the principle of Surface Plasmon Resonance (SPR), which is able to accurately measure changes in refractive index at a surface. Briefly, one interactant (the ligand) is immobilized to the surface of a sensor chip. A solution containing potential binding partner(s) is passed over the immobilized surface, and binding is visualized as a change in refractive index at the surface (response units (RU)) over time. Surface Plasmon Resonance allows for immediate visualization of interactions in a label-free manner, lessening the potential impact of labels on the interaction of interest.

The following biotinylated polypeptides; H1 (A/Solomon Islands/03/06), H3 (A/Wyoming/3/2003), H5 (A/Vietnam/1203/2004), H7 (A/Netherlands/219/03) and H9 (A/Hong Kong/1073/99) were each bound to the surface of a separate Biacore sensor chip. An antibody of varying concentration, was passed over the chip for SPR binding analysis. Data was plotted as a function of response difference measured in RU verses time. The various kinetic rate values were calculated using the following equations:

$$\frac{d[AB]}{dt} = k_a \cdot [A] \cdot [B]$$

$$\frac{-d[AB]}{dt} = k_d \cdot [AB]$$

$$K_D = \frac{k_d}{k_a}$$

where d[AB] is RU, where [A] is antibody concentration, [B] is [$R_{max}$–R], $k_a$ is the association constant, $k_d$ is the dissociation constant and $K_D$ is the equilibrium dissociation constant.

Using the above referenced calculation, we have observed differential kinetic binding rates between the antibody and HA polypeptides from different influenza subtypes (FIGS. 3A-E). In some embodiments, we have observed exemplary antibodies with $K_D$ values in the range of 0.01 to 100 nM for binding of antibodies to different HA polypeptide subtypes. In some embodiments, we have observed exemplary antibodies with $K_D$ values in the range of 0.1 to 500 nM for binding of antibodies to different HA polypeptide subtypes. In some embodiments, we have observed $K_D$ values in the range of 10 to 100 nM for binding of antibodies to HA polypeptides subtypes. In some embodiments, we have observed $K_D$ values in the range of 50 to 100 nM for binding of antibodies to HA polypeptides subtypes.

In some embodiments, we have observed exemplary antibodies with kavalues in the range of $0.01\times10^5$ to $0.1\times10^5$ $M^{-1}s^{-1}$ for binding of antibodies to different HA polypeptide subtypes. In some embodiments, we have observed exemplary antibodies with kavalues in the range of $0.1\times10^5$ to $1.0\times10^5$ $M^{-1}s^{-1}$ for binding of antibodies to different HA polypeptide subtypes. In some embodiments, we have observed exemplary antibodies with $k_a$ values in the range of $1.0\times10^5$ to $1.0\times10^6$ $M^{-1}s^{-1}$ for binding of antibodies to different HA polypeptide subtypes.

In some embodiments, we have observed exemplary antibodies with $k_d$ values in the range of $0.01\times10^{-5}$ to $0.1\times10^{-5}$ $s^{-1}$ for binding of antibodies to different HA polypeptide subtypes. In some embodiments, we have observed exemplary antibodies with $k_d$ values in the range of $0.1\times10^{-5}$ to $1.0\times10^{-5}$ $s^{-1}$ for binding of antibodies to different HA polypeptide subtypes. In some embodiments, we have observed exemplary antibodies with $k_d$ values in the range of $1.0\times10^{-5}$ to $10.0\times10^{-6}$ $s^{-1}$ for binding of antibodies to different HA polypeptide subtypes.

Example 4

Antibodies Inhibit Virus Infectivity In Vitro

The present example illustrates the ability of an exemplary influenza antibody to prevent virus infectivity in an in vitro binding assay.

The ability of the exemplary influenza antibody of Example 1 to inhibit influenza infection was evaluated in vitro using MDCK (Madin-Darby Canine Kidney) cells, an epithelial cell line commonly used for the propagation and testing of influenza virus strains. The inhibitory effects of the antibody on infectivity were determined by measuring both viral yield and the extent of influenza-induced cytopathic effects (CPE) on the host cells. Plaque assay and qRT-PCR were employed to quantify viral production. A cell viability assay was used to measure CPE levels. The experiments were set up to allow for the antibody to first bind to its viral target during a one hour pre-incubation period before introduction to the host cells. Infection was carried out in the presence of low levels of trypsin (1 μM). The plaque assay was performed by inoculating confluent monolayer of cells with serial dilutions of test samples and overlaying with a viscous suspension of the polymer Avicel (FMC Biopolymers). Plaques were allowed to develop over a period of 48 hours @ 35° C., formalin fixed, stained with crystal violet and visualized (FIG. 4). The plaque count was used to calculate infectious viral titers in the test samples. The relative number of viable cells following infection was used as a measure of CPE. Sub-confluent cell cultures were exposed to a compound/virus mix (moi=1.0) for a period of one hour @ 35° C. Unbound virus and drug were then removed and replaced with virus growth medium. Cell viability was determined following 48 hours incubation using Promega's CellTiter Blue reagents (resazurin) as the extent of the metabolic conversion of the non-fluorescent resazurin to fluorescent resorufin read (555/585 nm excitation/emission; SpectraMax M2; Molecular Probes).

From these studies, we have found that the exemplary antibody inhibits virus-induced plaque production.

Example 5

$IC_{50}$ Evaluation of an Influenza Antibody

The present example illustrates the ability of an exemplary influenza antibody to prevent virus infectivity in an in vitro binding assays.

The $IC_{50}$s for anti-influenza agents targeting HA have previously been quantified. Studies utilized the H1N1 influenza strain PR8 (A/Puerto Rico/8/34). In brief, confluent MDCK cells were infected with PR8 [4E3 PFU/mL] and pre-incubated for 40 minutes with varying concentrations of anti-influenza agents. After one hour of infection, media was removed and replaced with virus-free, drug-containing media or virus-free, drug-free media depending upon the experiment. After 48 hours of incubation at 37° C., 5% $CO_2$, supernatants were collected. Viral RNA was isolated, and viral titer was quantified by real time PCR using primers specific for the virus M protein.

Initial assessment of $IC_{50}$ values for an exemplary antibody of Example 1, was determined by microneutralization assay followed by quantitative PCR (qPCR). Mixtures of virus (PR8) and influenza targeting antibody at various titers and concentrations, respectively, were pre-incubated for 1 hour at 35° C. before being applied to MDCK cell cultures in a 96-well tissue culture plate (~10,000 cells/well). After an additional 48 hours of incubation, the culture medium was collected from each well for viral yield.

Media from triplicate samples were combined and then subjected to direct quantification of viral yield by qPCR. Viral titers were calculated from the PCR Ct values with the aid of an internal standard curve, and the $IC_{50}$ values were determined by plotting the calculated titers against antibody concentrations (FIG. 5). The results showed 50% inhibition ($IC_{50}$) of PR8 viral particles with 0.5 μg/ml of the antibody from example 1. These results suggest that the antibody of Example 1 is able to inhibit influenza virus infectivity. In some embodiments, we have observed $IC_{50}$ values in the range of 0.01 to 10 μg/ml for inhibiting influenza infectivity for various influenza strains. In some embodiments, we have observed $IC_{50}$ values in the range of 0.1 to 100 μg/ml for inhibiting influenza infectivity for various influenza strains.

Example 6

Influenza Antibody Binds HA Polypeptides In Vivo

The present example illustrates the ability of influenza antibodies to bind HA polypeptides in vivo.

The ability of the exemplary influenza antibody of Example 1 to inhibit influenza infection was evaluated in vivo. More particularly, assays were performed to evaluate whether antibody administered at various concentrations prior to infection, could serve as a prophylaxis in reducing influenza infectivity.

Figure 6:
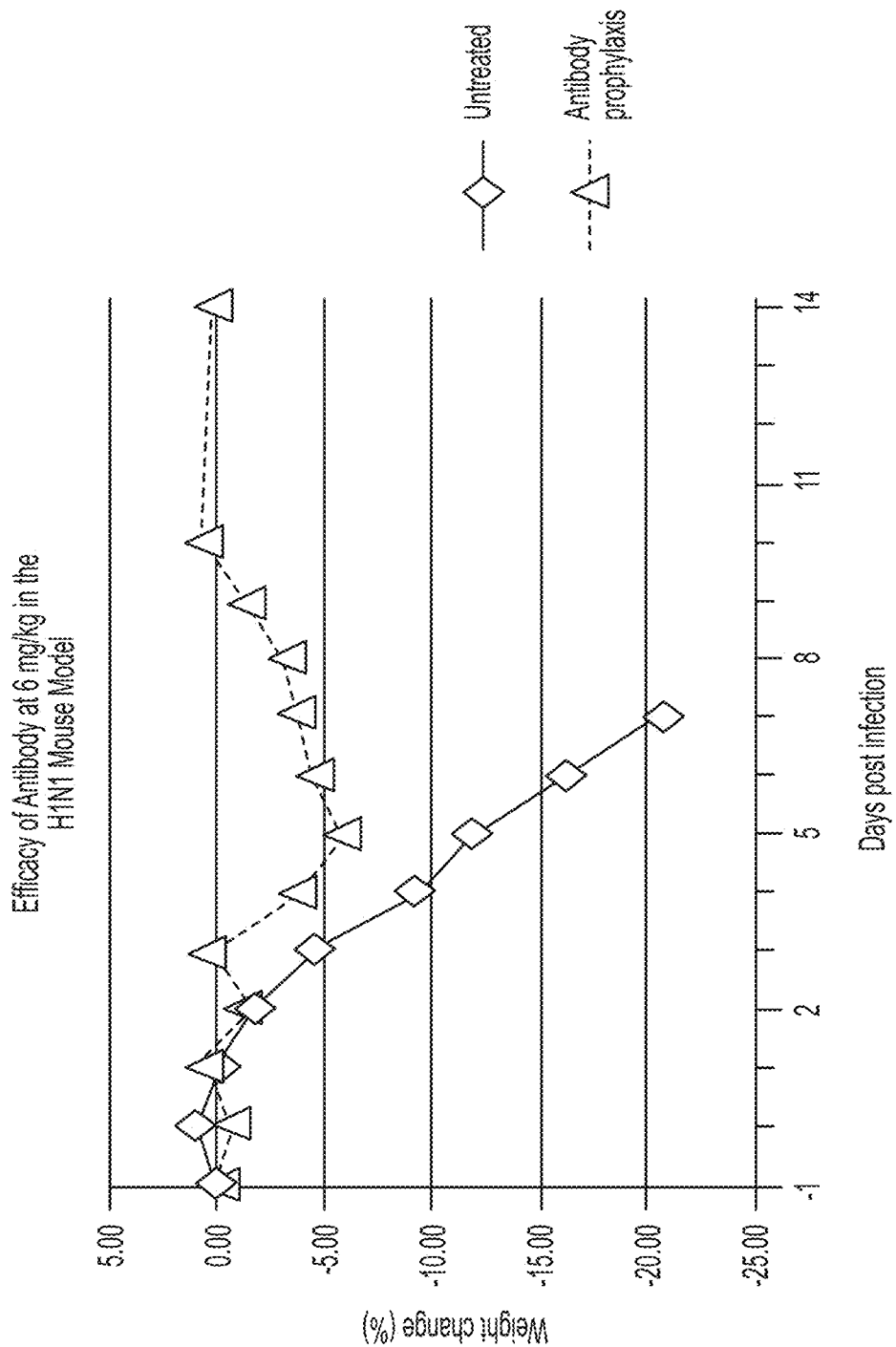
FIG. 6 presents data from mice treated with an exemplary antibody in an H1N1 challenge. In this challenge, mice treated with exemplary antibody have a lower percent of weight loss post infection compared to untreated control.

BALB/c mice (4-6 weeks old) were procured from Charles River Labs. Mice were weighed and divided into four groups of 6 mice each for the experiment. Groups consisted of: Group 1—no treatment control; Group 2—treatment with antiviral drug on days −1, 0 and 1; Group 3—treatment with single dose of 6 mg/kg of antibody; and Group 4–treatment with a single dose of 10 mg/kg of antibody. On the first day prior to infection (day −1) each group was administered with isoflurane, and dosed with control, 75 mg/kg of antiviral drug Ribavirin and influenza antibody (either 6 or 10 mg/kg) and allowed to recover (<2 min). The following day (day 0) each group was re-administered with isoflurane and challenged intranasally with a lethal dose of H1N1 PR8 virus. As indicated above, Group 2 was also administered 75 mg/kg on days 0 and 1 of the experiment. Mice were monitored daily for 14 days for changes in weight loss associated with viral infection, and survival rate recorded daily. Clinical signs of influenza infection in mice include hunched posture, ruffled fur, rapid breathing, loss of appetite, weight loss, and death. FIG. 6 demonstrates that those mice prophylactically treated with antibody demonstrated little to no weight loss, when compared to the control group.

Figure 7:
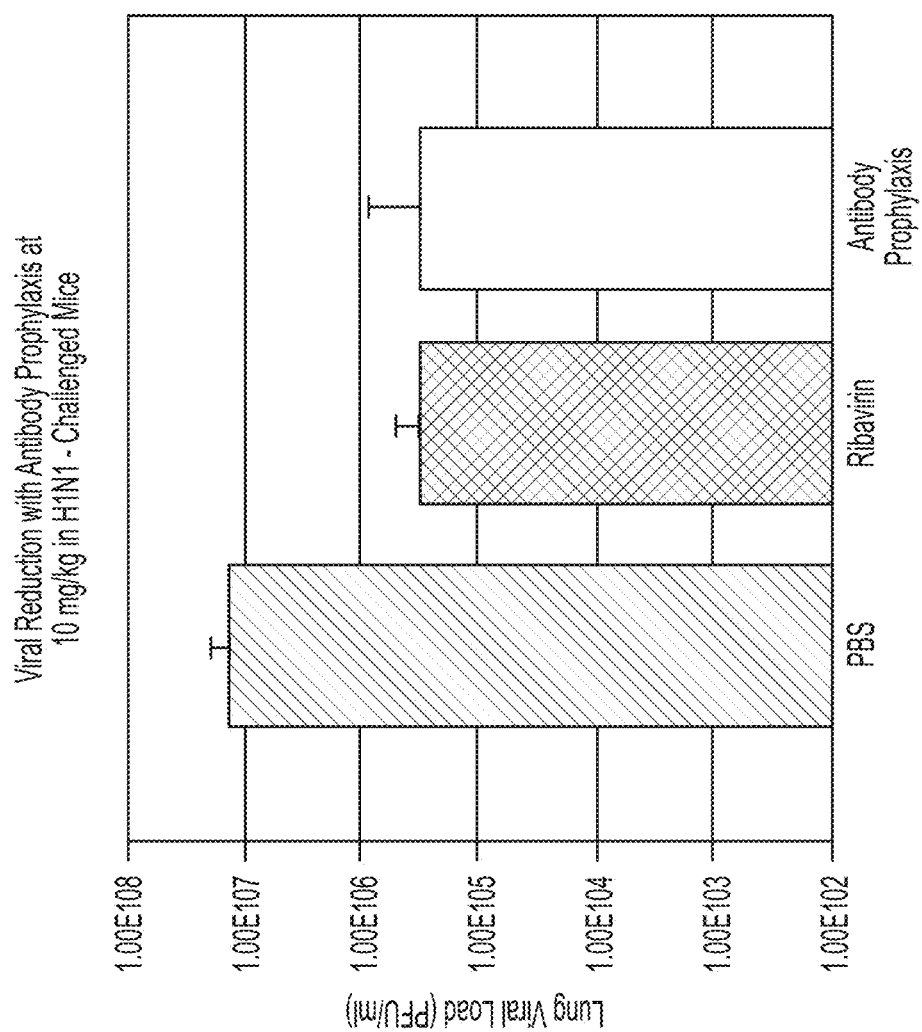
FIG. 7 presents data from a H1N1 challenge in mice. AS can be seen, an exemplary antibody delays the development of H1N1 infection in mice as compared to that observed with a PBS control. The observed decrease in infectivity (i.e., in the rate of onset of symptoms of infection) in the presence of exemplary antibody is comparable to that seen with the antiviral embodiments, an amino acid has the general structure H$_2$N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In addition to weight loss, viral yield was measured in a post-infection bronchio-aveolar lavage assay. Nasal washes were collected on day 3 from three animals from each of groups 1, 2 and 4, and their lungs were harvested prior to sacrifice. Bronchio-aveolar lavage fluid from the three mice were combined and subjected to direct quantification of viral yield by qPCR. Viral RNA was isolated, and viral titer quantified by real time PCR using primers specific for the virus M protein. Viral titers were calculated from the PCR Ct values with the aid of an internal standard curve. The data presented in FIG. 7 suggests that a single prophylactic antibody treatment prior to influenza infection leads to a reduced level of infection (as demonstrated by viral load) similar to that of the antiviral drug Ribavirin.

The results of these studies show, among other things, that provided antibodies can successfully delay and/or prevent onset of H1N1 infection in mice, when administered prior to infection.

Example 7

Evaluation of Influenza Antibodies as a Therapy In Vivo

The present example illustrates the ability of influenza antibodies to bind HA polypeptides in vivo for use as a treatment.

The ability of the exemplary influenza antibody of Example 1 to inhibit influenza infection was evaluated in vivo. Assays were performed to evaluate whether antibody administered at various concentrations post-infection, could serve as treatment therapy in reducing influenza infectivity.

Figure 8:
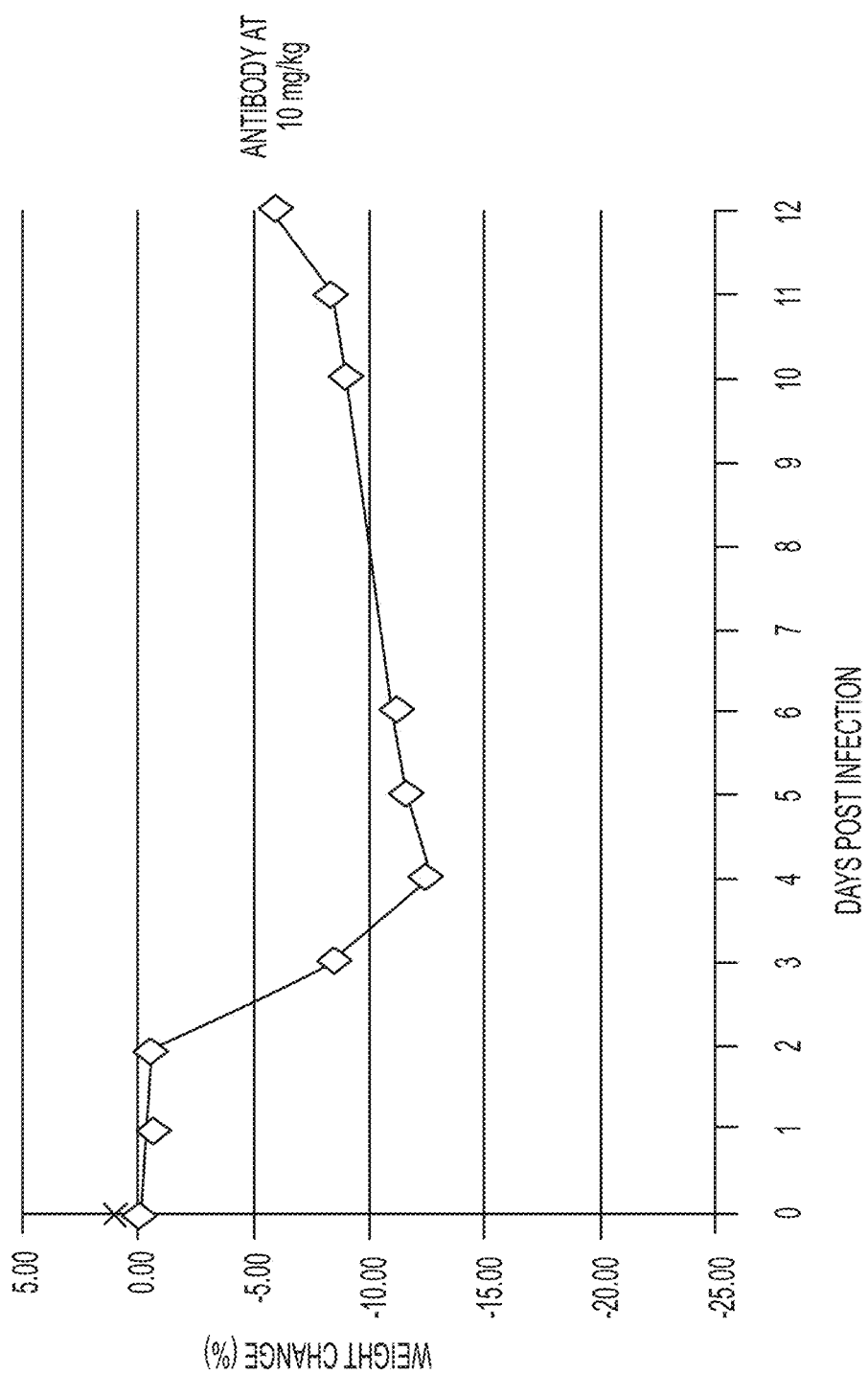

BALB/c mice (4-6 weeks old) were procured from Charles River Labs. Mice were weighed and divided into three groups of 6 mice each for the experiment. Groups consisted of: Group 1—no treatment control; Group 2—treatment with a single dose of 5 mg/kg of antibody; and Group 3—treatment with a single dose of 10 mg/kg of antibody. At the start of the experiment (day 0), each group is administered isoflurane and challenged intranasally with a lethal dose of H1N1 PR8 virus. Two day post-infection (day 2), each group was re-administered isoflurane, and dosed with control, 5 mg/kg of influenza antibody, or 10 mg/kg of influenza antibody and allowed to recover (<2 min). Mice were monitored daily for 14 days for changes in weight loss associated with viral infection, and survival rate recorded daily. Clinical signs of influenza infection in mice include hunched posture, ruffled fur, rapid breathing, loss of appetite, weight loss, and death. FIG. 8 demonstrates that those mice treated with antibody therapy showed reversal of one or more symptoms of infection. For example, a reversal in viral associated weight loss, resulting in an increased survival rate when compared to control. These results indicate that antibody therapy can reverse disease state and symptoms associated with influenza infection.

Example 8

Pharmacokinetic Evaluation of an Antibody In Vivo

The present Example describes pharmacokinetic properties of an influenza antibody in vivo.

Figure 9:
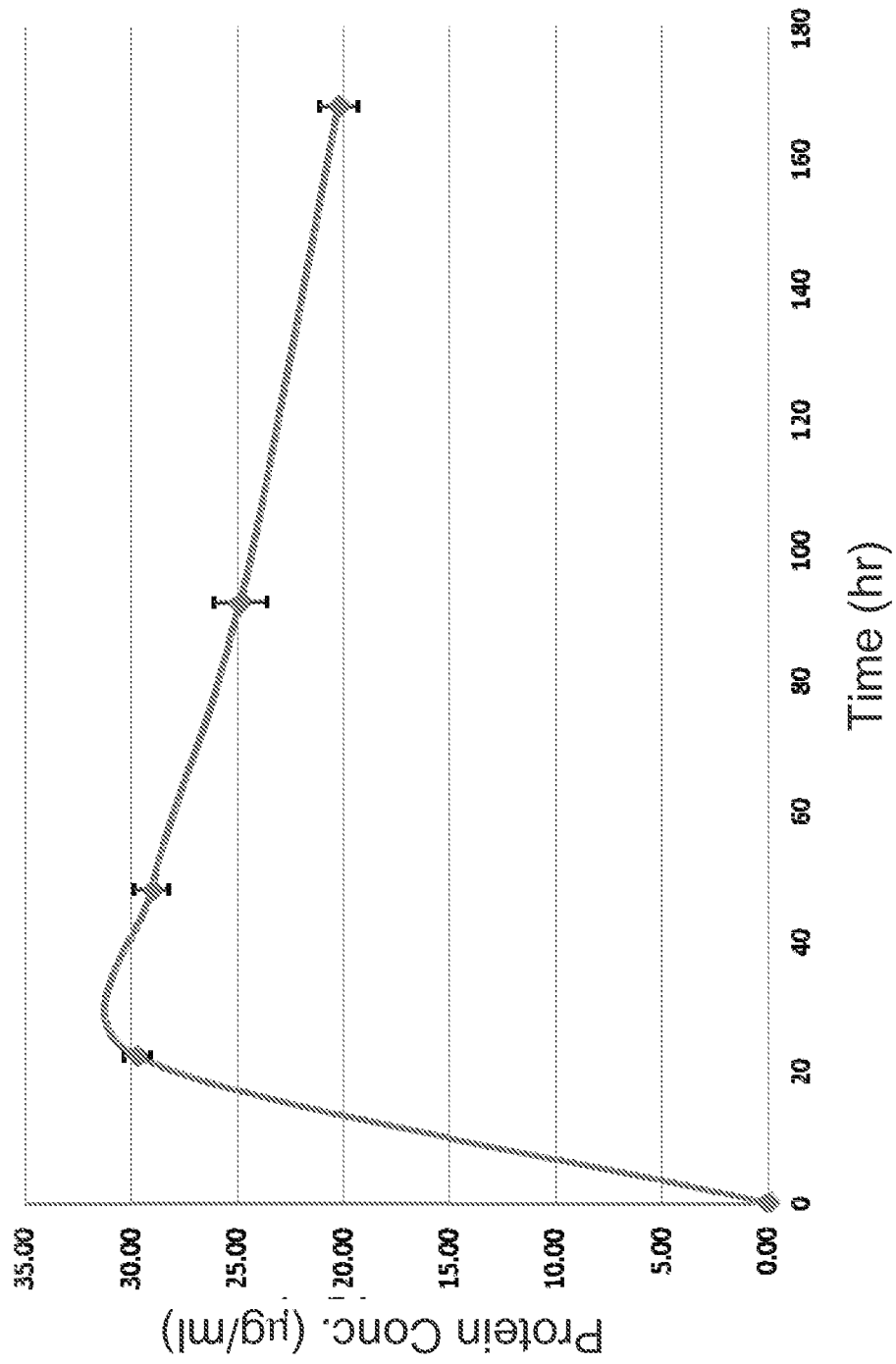

BALB/c mice (4-6 weeks old) were procured from Charles River Labs and placed in a single group of 6 mice for the experiment. Each mouse received a single bolus injection of 5 mg/ml of antibody. Serum samples were collected at predetermined time-points over a 180 hr period. Collected samples were evaluated by ELISA, using methods as described herein. Briefly, maxisorp 96-well plate wells were coated with 0.2 μg of human IgG and left overnight at 4° C. The human IgG coated plates were washed thrice with PBS and blocked with 1% BSA in PB ST. Serum samples collected over the 180 hr. period following antibody injection, were added to the human IgG coated wells and the plate was incubated at RT for 2 hrs. The plate was washed thrice with PBST and the wells were incubated with goat-anti-mouse HRP antibody for 1 hr at RT. Post-incubation the wells were washed with PBST and the bound HRP was measured using TMB substrate. TMB substrate was added to the wells, incubated for 3 minutes, followed by addition of 1 N sulfuric acid. Absorbance was measured at 450 nm. The data in FIG. 9 demonstrates a rapid distribution phase from 0 to 30 hours, with a peak serum concentration at approximately 30 hours. FIG. 9 also demonstrates a gradual elimination phase from 30 to 160 hours, indicating a reduction in serum antibody concentration, which suggests possible clearance or partitioning of the antibody into different compartments of the mouse's body.

Example 9

Binding Agents in Diagnostics

The present example illustrates the ability of exemplary influenza antibodies to provide a rapid way for (a) identifying the presence of influenza virus in a biological sample and (b) characterizing the virus, based on the subtype.

A sandwich ELISA (virus typing ELISA assay) assay is used for the purpose of identifying the presence of influenza virus and characterizing the virus subtype. For the virus typing ELISA assay, 96-well plates will be coated with 2 μg of influenza antibody and incubated overnight at 4° C. The plates would then be extensively washed with PBS and blocked with 1% BSA in PBST for 1 hr. Post blocking, the plates are washed with PBST and stored at 4° C. till further use.

Biological samples suspected of containing influenza virus are diluted in sample buffer (PBS) either directly or post processing. The diluted samples are applied to the influenza antibody-coated wells and incubated for 2 hrs at room temperature (RT) followed by extensive washing. Virus from the sample are thus captured by the influenza antibody and lend itself for further analysis. Subtype specific antibody are applied to different wells for 1 hr at RT. After further washes with PBST, HRP-conjugated secondary antibodies are applied to the wells. Post-incubation, the wells are washed, and treated with TMB substrate and 1 N sulfuric acid. The absorbance at 450 nm is measured using a spectrophotometer. Appropriate negative and positive controls are included.

The results of the virus typing ELISA assay yield information about the presence of influenza virus in a sample and the subtype of the virus.

Example 10

Antibodies for Influenza Virus Glycan Characterization

The present example illustrates the ability of an exemplary influenza antibody as means to enrich and label influenza virus for glycan characterization using a glycan typing assay.

In the glycan typing assay, the influenza antibody is conjugated to Qdot 525 Carboxyl Quantum Dots using EDC chemistry as per manufacturers instruction. The Qdot-influenza antibody complex is added to processed biological samples and stirred well for 2 hrs. The sample is then centrifuged and the Qdot-influenza antibody complex is washed thrice with PBST. This complex is then applied on glycan array (containing umbrella and cone topology glycans). After incubating for 2 hrs at RT, the wells are washed thrice with PBST. The bound fluorescence is measured using SpectraMax M2e spectrophotometer using bottom read mode.

The results of this assay yield information regarding the glycan characterization of influenza viruses.

Example 11

Minimum Inhibitory Activity Assay

A method to determine the minimum inhibitory concentration (MIC) of the influenza antibody against influenza A is used. To be active in this assay, the influenza antibody must bind to the virus and neutralize the virus' ability to form plaques. Briefly, an influenza antibody is serially diluted in two fold increments in PBS to form a concentration gradient across multiple wells. A known number of viral plaque forming units are added to each well and after 1 hour incubation, the mixture is added to an MDCK monolayer to allow viral binding. An Avicel overlay encourages plaque formation and the plaques are visualized by immunostain. The lowest concentration of agent to prevent plaque formation is reported as the MIC. These studies utilize H1N1 strain PR8 (A/Puerto Rico/8/34). Representative influenza antibody activity in the assay versus H1N1 is determined.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method comprising:
   administering to a subject suffering from or susceptible to influenza infection a therapeutically effective amount of a combination therapy, comprising
   an engineered antibody, or antigen-binding fragment thereof, and one or more therapeutic agents, wherein the antibody comprises:
   (a) a heavy chain variable region that shows at least 99% substantial sequence homology with that of heavy chain variable region of SEQ ID NO: 1; and
   (b) a light chain variable region that shows at least 99% substantial sequence homology to one of SEQ ID NOs: 33-43.

2. The method of claim 1, wherein the antibody and one or more other therapeutic agents are administered together.

3. The method of claim 1, wherein the antibody and one or more other therapeutic agents are administered at different times.

4. The method of claim 1, wherein the one or more other therapeutic agents are selected from the group consisting of an anti-influenza vaccine, an anti-viral agent, a pain reliever, an anti-inflammatory agent, an antibiotic, a steroidal agent, an antibody, and sialydase.

5. The method of claim 1, wherein the one or more therapeutic agents comprises an anti-viral agent.

6. The method of claim 5, wherein the anti-viral agent is selected from the group consisting of acyclovir, ribavirin, amantadine, remantidine, zanamivir (Relenza), oseltamivir (Tamiflu), amantadine, rimantadine and combinations thereof.

7. The method of claim 5, wherein the anti-viral agent comprises oseltamivir (Tamiflu).

8. The method of claim 1, wherein the one or more other therapeutic agents comprises an anti-viral vaccine.

9. The method of claim 8, wherein the anti-viral vaccine is an anti-influenza vaccine.

10. The method of claim 1, further comprising administering one or more pharmaceutical agents used to treat the symptoms associated with influenza virus infection.

11. The method of claim 10, wherein the one or more pharmaceutical agents are selected from the group consisting of pain relievers, anti-inflammatories, antibiotics and combinations thereof.

12. The method of claim 11, wherein the one or more pharmaceutical agents are selected from the group consisting of NSAID, Steroid, Glucocorticoid, and combinations thereof.

13. The method of claim 1, wherein the combination therapy further comprises a pharmaceutically acceptable excipient.

14. The method of claim 1, wherein the combination therapy is formulated for administration by a route selected from the group consisting of oral, intravenous, intramuscular, intra-arterial, subcutaneous, intraventricular, transdermal, interdermal, rectal, intravaginal, intraperitoneal, topical, mucosal, nasal, buccal, enteral, sublingual, intratracheal or bronchial.

15. The method of claim 14, wherein the antibody is administered by intratracheal or bronchial instillation.

16. The method of claim 14, wherein the antibody is administered by inhalation.

17. The method of claim 14, wherein the antibody is formulated as an oral spray, a nasal spray, or an aerosol.

18. A method comprising:
administering to a subject suffering from or susceptible to influenza infection an antibody, or antigen-binding fragment thereof, and one or more therapeutic agents, wherein:
the antibody comprises:
   (a) a heavy chain variable region that shows at least 99% substantial sequence homology with that of heavy chain variable region of SEQ ID NO: 1; and
   (b) a light chain variable region that shows at least 99% substantial sequence homology to one of SEQ ID NOs: 33-43.

* * * * *